US007205306B2

(12) United States Patent
Arvanitis et al.

(10) Patent No.: US 7,205,306 B2
(45) Date of Patent: Apr. 17, 2007

(54) SUBSTITUTED PYRAZINONES, PYRIDINES AND PYRIMIDINES AS CORTICOTROPIN RELEASING FACTOR LIGANDS

(75) Inventors: Argyrios G Arvanitis, Kennett Square, PA (US); Paul J Gilligan, Wilmington, DE (US); Richard A Hartz, Kennett Square, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/145,440

(22) Filed: May 14, 2002

(65) Prior Publication Data
US 2003/0171380 A1    Sep. 11, 2003

Related U.S. Application Data

(60) Provisional application No. 60/290,706, filed on May 14, 2001.

(51) Int. Cl.
C07D 401/04    (2006.01)
C07D 403/04    (2006.01)
A61K 31/506    (2006.01)
A61K 31/497    (2006.01)
A61K 31/4439   (2006.01)
A61P 25/22     (2006.01)

(52) U.S. Cl. ............... 514/254.09; 514/256; 514/337; 514/338; 514/339; 544/326; 544/328; 544/405; 544/408; 546/277.4

(58) Field of Classification Search ............... 544/326, 544/328, 405, 408, 406; 546/277.4, 277; 514/254.09, 256, 337, 338, 339
See application file for complete search history.

(56) References Cited

U.S. PATENT DOCUMENTS

| 4,296,114 A   | 10/1981 | Appleton et al. ........... 424/248 |
| 5,223,505 A * | 6/1993  | Hargreaves et al. ........ 514/275  |
| 5,382,593 A * | 1/1995  | Le Baut et al. ............ 514/418 |
| 5,395,817 A * | 3/1995  | Pallos et al. .............. 504/252 |
| 6,245,769 B1  | 6/2001  | Arvanitis                           |

FOREIGN PATENT DOCUMENTS

| DE | 4029648 A  * | 3/1992  |
| WO | WO 94/13676 A1 | 6/1994 |
| WO | WO 95/10506 | 4/1995 |
| WO | WO 97/35539 | 10/1997 |
| WO | WO 97/35846 | 10/1997 |
| WO | WO 97/44308 | 11/1997 |
| WO | WO 9744326 A1 * | 11/1997 |
| WO | WO 98/03510 | 1/1998 |
| WO | WO 98/11075 A1 | 3/1998 |
| WO | WO 99/01439 | 1/1999 |
| WO | WO 99/01454 | 1/1999 |
| WO | WO 99/11643 | 3/1999 |
| WO | WO 99/51608 | 10/1999 |
| WO | WO 00/01675 | 1/2000 |
| WO | WO 00/11003 | 3/2000 |

OTHER PUBLICATIONS

Ojea, Vicente; Muinelo, Isabel; Quintela, Jose M., Tetrahedron, 54(5/6), 927-934 (English) 1998.*
J. Rivier et al., Proc. Nat. Acad. Sci. (USA) 80:4851 (1983).
W. Vale et al., Science 213:1394 (1981).
W. Vale et al., Rec. Prog. Horm. Res. 39:245 (1983).
G.F. Koob, Persp. Behav. Med. 2:39 (1985).
E.B. DeSouza et al., J. Neurosci. 5:3189 (1985).
J.E. Blalock, Physiological Reviews 69:1 (1989).
J.E. Morley, Life Sci. 41:527 (1987).
E.B. DeSouza, Hosp. Practice 23:59 (1988).
C.B. Nemeroff et al., Science 226:1342 (1984).
C.M. Banki et al., Am. J. Psychiatry 144:873 (1987).

(Continued)

Primary Examiner—Venkataraman Balasubramanian
(74) Attorney, Agent, or Firm—Shah R. Makujina; Woodcock Washburn, LLP

(57) ABSTRACT

Compounds provided herein are novel substituted pyrazinones, pyridines and pyrimidines of Formula (I) and (II):

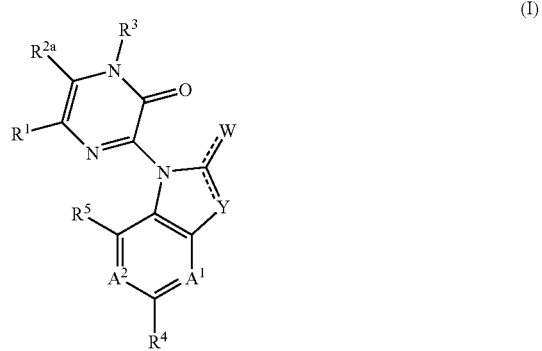

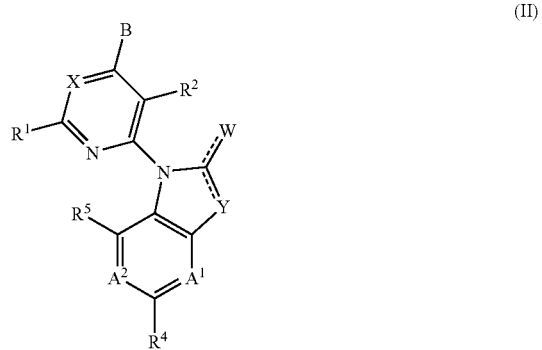

Such compounds are particularly useful as CRF receptor ligands, and hence, in the treatment of various neurologically-related disorders such as affective disorder, anxiety and depression.

16 Claims, No Drawings

OTHER PUBLICATIONS

R.D. France et al., Biol. Psychiatry 28:86 (1988).
M. Arato et al., Biol. Psychiatry 25:355 (1989).
C.B. Nemeroff et al., Arch. Gen. Psychiatry 45:577 (1988).
P.W. Gold et al, Am. J. Psychiatry 141:619 (1984).
F. Holsboer et al., Psychoneuroendocrinology 9:147 (1984).
P.W. Gold et al., New Eng. J. Med. 314:1129 (1986).
R.M. Sapolsky, Arch. Gen. Psychiatry 46:1047 (1989).
Grigoriadis et al., Neuropsychopharmacology 2:53 (1989).
D.R. Britton et al., Life Sci. 31:363 (1982).
C.W. Berridge et al., Regul. Peptides 16:83 (1986).
C.W. Berridge et al., Horm. Behav. 21:393 (1987).
Brain Research Reviews 15:71 (1990).
K.T. Britton et al., Psychopharmacology 86:170 (1985).
K.T. Britton et al., Psychopharmacology 94:306 (1988).
N.R. Swerdlow, Psychopharmacology 88:147 (1986).
G.F. Koob et al., Corticotropln-Releasing Factor: Basic and Clinical Studies of a Neuropeptide p. 221 (1990).
C. Maillot et al., Gastroenterology, 119, 1569-1579 (2000).
J.R. McCarthy et al., Curr. Pharm. Res., 5, 289-315 (1999).
P.J. Gilligan et al., J. Med. Chem, 431641-1660 (2000).
G.P. Chrousos, Int. J. Obesity, 24, Supp 2, S50-S55 (2000).
E. Webster et al., Ann. N.Y. Acad. Sci., 840, 21-32 (1998).
D.J. Newport et al., Curr. Opin. Neurobiology, 10, 211-218 (2000).
G. Mastorakos et al., Ann. N.Y. Acad. Sci., 900, 95-106 (2000).
M.J. Owens et al., Expert Opin. Invest. Drugs, 8, 1849-1858 (1999).
G.F. Koob, Ann. N.Y. Acad. Sci., 909, 170-185 (2000).
Remington's Pharmaceutical Sciences, 17$^{th}$ ed., Mack Pub. Co, Easton, PA, 1985, p. 1418.
R.C. Larock et al., Tetrahedron Let., 44, 5291 (1987).
Y. Tamura et al., Synthesis, 534 (1981).
Y. Tamura et al., Chem. Pharm. Bull, 32, 1995 (1984).
R.F. Heck et al., Acc. Chem. Res., 12, 146 (1979).
J. Vekemans et al., J. Heterocyclic Chem, 20, 919 (1982).
K. Hirota et al., J. Org. Chem, 57, 5268 (1992).
V. Ratovelomanana et al., Tet. Letters, 52, 6001 (1984).
J. Munson et al., Anal. Biochem., 107:220 (1980).
G. Battaglia et al., Synapse, 1:572 (1987).
Hawley's Condensed Chemical Dictionary (13$^{th}$ ed.), J. Wiley & Sons, NY (1997).
Green et al., Protecting Groups in Organic Synthesis, Wiley, NY (1991).
J. March, Advanced Organic Chemistry, Wiley, NY (1992).
The PCT International Search Report dated Sep. 19, 2002 (PCT/US02/15493).

* cited by examiner

SUBSTITUTED PYRAZINONES, PYRIDINES AND PYRIMIDINES AS CORTICOTROPIN RELEASING FACTOR LIGANDS

This application claims benefit of U.S. Provisional Application No. 60/290,706, filed May 14, 2001.

FIELD OF THE INVENTION

This invention relates to compounds which are novel substituted pyrazinones, pyridines and pyrimidines; to pharmaceutical compositions thereof, and to the use of such compounds as CRF receptor ligands in the treatment of various CRF-related disorders.

BACKGROUND OF THE INVENTION

Corticotropin releasing factor (herein referred to as CRF), a 41 amino acid peptide, is the primary physiological regulator of proopiomelanocortin (POMC)—derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebrospinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome post-operative ileus and colonic hypersensitivity associated with psychopathological disturbance and stress [for reviews see E. D. DeSouza, C. B. Nemeroff, Editors; *Corticotropin-Releasing Factor: Basic and Clinical Studies of a Neuropeptide*, E. B. De Souza and C. B. Nemeroff eds., CRC Press p221 (1990) and C. Maillot, M. Million, J. Y. Wei, A. Gauthier, Y. Tache, Gastroenterology, 119, 1569–1579 (2000)].

Over-expression or under-expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress [for reviews see J. R. McCarthy, S. C. Heinrichs and D. E. Grigoriadis, *Cuur. Pharm. Res.,* 5, 289–315 (1999); P. J. Gilligan, D. W. Robertson and R. Zaczek, J. Medicinal Chem., 43, 1641–1660 (2000), G. P. Chrousos, Int. J. Obesity, 24, Suppl. 2, S50-S55 (2000); E. Webster, D. J. Torpy, I. J. Elenkov, G. P. Chrousos, Ann. N.Y. Acad. Sci., 840, 21–32 (1998); D. J. Newport and C. B. Nemeroff, Curr. Opin. Neurobiology, 10, 211–218 (2000); G. Mastorakos and I. Ilias, Ann. N.Y. Acad. Sci., 900, 95–106 (2000); M. J. Owens and C. B. Nemeroff, Expert Opin. Invest. Drugs, 8, 1849–1858 (1999); G. F. Koob, Ann. N.Y. Acad. Sci., 909, 170–185 (2000)].

Lastly, studies have demonstrated that CRF-1 antagonists are may be useful as hair growth stimulators. PCT publication WO2002/19975 discloses cell culture assays for the use of CRF antagonists in stimulating KBM-2 cell production. Thus, CRF antagonists may be useful in treatment of hair loss.

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and WO00/01675. Even with the current development efforts of CRF antagonist compounds, it is desirable to develop additional CRF receptor ligands in the treatment of various CRF-related disorders.

SUMMARY OF THE INVENTION

This invention is a class of novel compounds which are CRF receptor ligands and which can be represented by Formula (I) and (II):

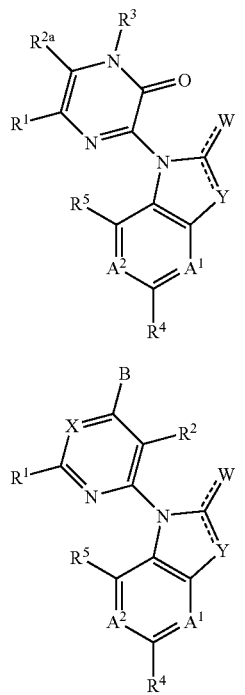

or a pharmaceutically acceptable salt form thereof, wherein:
X is N or $CR^1$;

provided that when X is N, $R^1$ can not be either $—NR^9R^{10}$ or $—NR^9COR^9$;
W is $=O$, $=S$, $—H$ or $(—H, —H)$;
Y is $—C(=O)—$, $—C(R^Y)_2—$, $—C(R^Y)_2CH_2—$, $—OCH_2—$, $—SO_nCH_2—$, $—N=$, $—NR^Y—$, $—O—$, or $—CH=$;
$R^Y$ is independently, at each occurrence, selected from H, methyl, ethyl, and $C_1$–$C_2$ haloalkyl;
B is $R^3$, $NHR^3$, $NR^3R^1$, $OR^3$, or $SO_nR^3$;
$R^1$ is independently, at each occurrence, selected from H, halogen, $—CN$, $C_1$–$C_4$ haloalkyl, $—NR^9R^{10}$, $—NR^9COR^9$, $—COR^{10}$, $—OR^{10}$, SH, $—S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;
wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, $—NR^9R^{10}$, $—NR^9COR^9$, $—COR^{10}$, $—OR^{10}$, SH or $—S(O)_nR^{12}$;
$R^2$ is H, halogen, CN, $C_1$–$C_4$ haloalkyl, $—NR^9R^{10}$, $NR^9COR^9$, $—COR^{10}$, $—OR^{10}$, SH, $—S(O)_nR^{12}$, $C_1$–$C_4$ alkyl, $C_3$–$C_6$ cycloalkyl, or $C_4$–$C_8$ cycloalkylalkyl;
wherein each $C_1$–$C_4$ alkyl, $C_3$–$C_6$ cycloalkyl, or $C_4$–$C_8$ cycloalkylalkyl is optionally substituted with halogen, $—CN$, $C_1$–$C_4$ haloalkyl, $—NR^9R^{10}$, $—NR^9COR^9$, $—COR^{10}$, $—OR^{10}$, SH or $—S(O)_nR^{12}$;
$R^{2a}$ is H, F, Cl, Br, $—CN$, $—OH$, methyl, ethyl, propyl, cyclopropyl, cyclobutyl, methoxy, ethoxy, propoxy, $C_1$–$C_3$ alkoxy, cyclopropyloxy-, $—OCF_3$, $—CF_3$, $—CO_2CH_3$, $—CO_2CH_2CH_3$, $—C(O)CH_3$, $—C(O)CH_2CH_3$, $—CH_2OH$, $—CH_2OCH_3$, $—CH_2OCH_2CH_3$, $—C(O)NH_2$, $—C(O)N(H)$ $CH_3$, $—C(O)N(H)$ $CH_2CH_3$, $—C(O)N(CH_3)_2$, $—C(O)N(CH_3)$ $CH_2CH_3$, $—C(O)N(CH_2CH_3)_2$, $—S(O)_2N(CH_3)_2$, $—S(O)_2N(CH_3)CH_2CH_3$, $—S(O)_2N(CH_2CH_3)_2$, $—S(O)_2CH_3$, $—S(O)_2CH_2CH_3$, $—NH_2$, $—N(H)CH_3$, $—N(H)CH_2CH_3$, $—N(CH_3)_2$, $—N(CH_3)$ $CH_2CH_3$, $—N(CH_2CH_3)_2$, or $—N(H)CF_3$;
$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;
wherein one carbon in any cycloalkyl ring may be replaced with O, S or $NR^9$; and
wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, $—OR^7$, SH, $—S(O)_nR^{11}$, $—COR^6$, $—NHR^6SO_2R^8$, $—OC(O)NR^6R^7$, $—N_3$, $—OC(O)OR^7$, $—CO_2R^8$, $—OC(O)R^6$, $—NR^7COR^6$, $—N(COR^6)_2$, $—NR^7CONR^6R^7$, $—NR^7CO_2R^8$, $—NR^6R^7$, $—CONR^6R^7$, $—CO_2H$, aryl, heteroaryl and heterocyclyl;
alternatively, $R^3$ is $—OR^{3a}$, $—NR^{3a}R^{3b}$, $—NHR^{3a}$, $—SO_nR^{3a}$, $—SO_2NHR^{3a}$, $—SO_2NR^{3a}R^{3b}$, $—COR^{3a}$, $—CONHR^{3a}$, or $—CONR^{3a}R^{3b}$;
$R^{3a}$ and $R^{3b}$ are independently selected from $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl;
wherein one carbon in any cycloalkyl may be replaced with O, S or $NR^9$; and
wherein each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, —SH, —S(O)$_n R^{11}$, —$COR^6$, —$CO_2 R^8$, —OC(O)$R^6$, —$NR^7 COR^6$, —N(COR$^6$)$_2$, —$NR^7 CONR^6 R^7$, —$NR^7 CO_2 R^8$, —$NR^6 R^7$, —NHR$^6 SO_2 R^8$, —OC(O)$NR^6 R^7$, —$N_3$, —OC(O)$OR^7$, —CONR$^6 R^7$, —$CO_2 H$, aryl, heteroaryl and heterocyclyl;

$R^4$ is independently selected in each occurrence from —H, —$OR^{10}$, —$COR^9$, —$CO_2 R^8$, —CONR$^9 R^{10}$, —CN, —$NR^9 R^{10}$, —S(O)$_n R^{12}$, —S(O)$_2 NR^9 R^{10}$, —$NO_2$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2 R^8$, —CONR$^9 R^{10}$, —CN, —$NR^9 R^{10}$, —S(O)$_n R^{12}$, or halogen;

$A^1$ is $CR^5$ or N;

$A^2$ is $CR^5$ or N;

$R^5$ is independently selected at each occurrence from —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6 R^7$, —$NR^6 COR^7$, —$NR^6 CO_2 R^8$, —$COR^6$—$OR^7$, —CONR$^6 R^7$, —CO(NOR$^9$)$R^{11}$, —$CO_2 R^8$, —S(O)$_2 NR^9 R^{10}$, and —S(O)$_n R^{11}$;

wherein $C_1$–$C_{10}$ alkyl, $C_2$–$C_{10}$ alkynyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6 R^7$, —$NR^6 COR^7$, $NR^6 CO_2 R^8$, —$COR^6$—$OR^7$, —CONR$^6 R^7$, —$CO_2 R^8$, —CO(NOR$^9$)$R^7$, and —S(O)$_n R^{11}$;

alternatively, two $R^5$ groups on adjacent atoms can form a 5–7 membered fused ring, partially saturated or unsaturated, optionally containing 1–2 —O— or —SO$_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6 R^7$, $NR^6 COR^7$, $NR^6 CO_2 R^8$, —$COR^6$—$OR^7$—O—CONRNR$^6 R^7$, —$CO_2 R^8$, —CO(NOR$^9$)$R^7$, or —S(O)$_n R^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl($C_1$–$C_4$ alkyl);

alternatively $NR^6 R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6 R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S(O)$_n R^{32}$, —$COR^{32}$, —$CO_2 R^{28}$, —OC(O)$R^{32}$, —$NR^{29} COR^{29}$, —N(COR$^{32}$)$_2$, —$NR^{29} CONR^{29} R^{30}$, —$NR^{29} CO_2 R^{28}$, —$NR^{29} R^{30}$, and —CONR$^{29} R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S(O)$_n R^{32}$, —$COR^{32}$, —$CO_2 R^{28}$, —OC(O)$R^{32}$, —$NR^{29} COR^{29}$, —N(COR$^{32}$)$_2$, —$NR^{29} CONR^{29} R^{30}$, —$NR^{29} CO_2 R^{28}$, —$NR^{29} R^{30}$, and —CONR$^{29} R^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, SH, —S(O)$_n R^{32}$, —$COR^{32}$, —$CO_2 R^{32}$, —OC(O)$R^{32}$, —$NR^{29} COR^{29}$, —N(COR$^{32}$)$_2$, —$NR^{29} CONR^{29} R^{30}$, —$NR^{29} CO_2 R^{32}$, —$NR^{29} R^{30}$, and —CONR$^{29} R^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

DETAILED DESCRIPTION OF THE INVENTION

This invention is a class of novel compounds which are CRF receptor ligands and which can be represented by Formula (I-a) and (II):

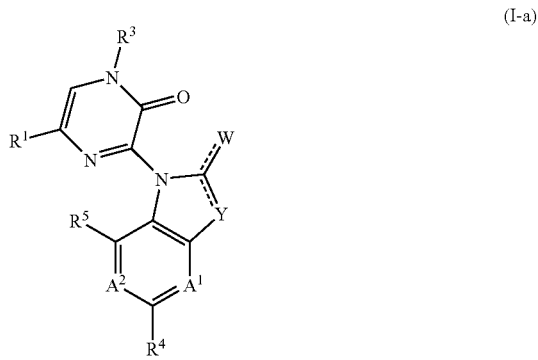

(I-a)

-continued

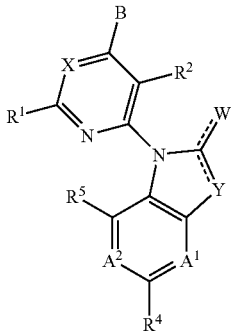
(II)

or a pharmaceutically acceptable salt form thereof, wherein:
X is N or $CR^1$;

provided that when X is N, $R^1$ can not be either $-NR^9R^{10}$ or $-NR^9COR^9$;

W is O, S, H or (—H, —H);

Y is CO, $CH_2$, $CH_2CH_2$, $OCH_2$, $SO_nCH2$, N, NH, $NCH_3$, O, or CH;

B is $R^3$, $NHR^3$, $NR^3R^1$, $OR^3$, or $SO_nR^3$;

$R^1$ is independently, at each occurrence, selected from H, halogen, —CN, $C_1$–$C_4$ haloalkyl, $-NR^9R^1$, $-NR^9COR^9$, $-COR^{10}$, $-OR^{10}$, SH, $-S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;
wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, $-NR^9R^{10}$, $-NR^9COR^9$, $-COR^{10}$, $-OR^{10}$, SH or $-S(O)_nR^{12}$;

$R^2$ is H, halogen, CN, $C_1$–$C_4$ haloalkyl, $-NR^9R^{10}$, $NR^9COR^9$, $-COR^{10}$, $-OR^{10}$, SH, $-S(O)_nR^{12}$, $C_1$–$C_4$ alkyl, $C_3$–$C_6$ cycloalkyl, or $C_4$–$C_8$ cycloalkylalkyl;
wherein each $C_1$–$C_4$ alkyl, $C_3$–$C_6$ cycloalkyl, or $C_4$–$C_8$ cycloalkylalkyl is optionally substituted with halogen, —CN, $C_1$–$C_4$ haloalkyl, $-NR^9R^{10}$, $-NR^9COR^9$, $-COR^{10}$, $-OR^{10}$, SH or $-S(O)_nR^{12}$;

$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;
wherein one carbon in any cycloalkyl ring may be replaced with O, S or $NR^9$; and
wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, $-OR^7$, SH, $-S(O)_nR^{11}$, $-COR^6$, $-NHR^6SO_2R^8$, $-OC(O)NR^6R^7$, $-N_3$, $-OC(O)OR^7$, $-CO_2R^8$, $-OC(O)R^6$, $-NR^7COR^6$. $-N(COR^6)_2$, $-NR^7CONR^6R^7$, $-NR^7CO_2R^8$, $-NR^6R^7$, $-CONR^6R^7$, $-CO_2H$, aryl, heteroaryl and heterocyclyl;
alternatively, $R^3$ is $-OR^{3a}$, $-NR^{3a}R^{3b}$, $-NHR^{3a}$, $-SO_nR^{3a}$, $-SO_2NHR^{3a}$, $-SO_2NR^{3a}R^{3b}$, $-COR^{3a}$, $-CONHR^{3a}$, or $-CONR^{3a}R^{3b}$;

$R^{3a}$ and $R^{3b}$ are independently selected from $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl;

wherein one carbon in any cycloalkyl may be replaced with O, S or $NR^9$; and
wherein each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, $-OR^7$, —SH, $-S(O)_nR^{11}$, $-COR^6$, $-CO_2R^8$, $-OC(O)R^6$, $-NR^7COR^6$, $-N(COR^6)_2$, $-NR^7CONR^6R^7$, $-NR^7CO_2R^8$, $-NR^6R^7$, $-NHR^6SO_2R^8$, $-OC(O)NR^6R^7$, $-N_3$, $-OC(O)OR^7$, $-CONR^6R^7$, $-CO_2H$, aryl, heteroaryl and heterocyclyl;

$R^4$ is independently selected in each occurrence from —H, $-OR^{10}$, $-COR^9$, $-CO_2R^8$, $-CONR^9R^{10}$, —CN, $-NR^9R^{10}$, $-S(O)_nR^{12}$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;
wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with $-OR^{10}$, $-COR^9$, $-CO_2R^8$, $-CONR^9R^{10}$, —CN, $-NR^9R^{10}$, $-S(O)_nR^{12}$, or halogen;

$A^1$ is $CR^5$ or N;
$A^2$ is $CR^5$ or N;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, $-NO_2$, halogen, —CN, $-NR^6R^7$, $-NR^6COR^7$, $-NR^6CO_2R^8$, $-COR^6$–$OR^7$, $-CONR^6R^7$, $-CO(NOR^9)R^{11}$, $-CO_2R^8$, or $-S(O)_nR^{11}$;
wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, $-NO_2$, halogen, —CN, $-NR^6R^7$, $-NR^6COR^7$, $NR^6CO_2R^8$, $-COR^6$—$OR^7$, $-CONR^6R^7$, $-CO_2R^8$, $-CO(NOR^9)R^7$, or $-S(O)_nR^{11}$;

alternatively, two $R^5$ groups on adjacent atoms can form a 5–7 membered fused ring, partially saturated or unsaturated, optionally containing 1–2 —O— or —$SO_n$— or 1–3 N heteroatoms provided the ring does not contain any S—S, O—O, S—O or N—S bonds;
said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, $-NO_2$, halogen, —CN, $-NR^6R^7$, $NR^6COR^7$, $NR^6CO_2R^8$, $-COR^6$—$OR^7$, $-CONR^6R^7$, $-CO_2R^8$, $-CO(NOR^9)R^7$, or $-S(O)_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_nR^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_nR^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, SH, —$S(O)_nR^{32}$, —$COR^{32}$, —$CO_2R^{32}$, —$OC(O)R^{32}$, —$NR^{29}COR^{29}$, —$N(COR^{32})_2$, —$NR^{29}CONR^{29}R^{30}$, —$NR^{29}CO_2R^{32}$, —$NR^{29}R^{30}$, and —$CONR^{29}R^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

Preferred compounds of this invention are compounds of Formula (I-a) and pharmaceutically acceptable salts and pro-drug form thereof, wherein:

W is (—H, —H);

Y is $CH_2$;

$R^1$ is independently, at each occurrence, selected from H, halogen, —CN, $C_1$–$C_4$ haloalkyl, —$NR^9R^{10}$, —$NR^9COR^9$, —$COR^{10}$, —$OR^{11}$, SH, —$S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;

wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, —$NR^9R^{10}$, —$NR^9COR^9$, —$COR^{10}$, —$OR^{10}$, SH or —$S(O)_nR^{12}$;

$R^2$ is H, halogen, CN, $C_1$–$C_4$ haloalkyl, —$NR^9R^{10}$, $NR^9COR^9$, —$COR^{10}$, —$OR^{10}$, SH, —$S(O)_nR^{12}$, $C_1$–$C_4$ alkyl, $C_3$–$C_6$ cycloalkyl, or $C_4$–$C_7$ cycloalkylalkyl;

wherein each $C_1$–$C_4$ alkyl, $C_3$–$C_6$ cycloalkyl, or $C_4$–$C_7$ cycloalkylalkyl is optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;

$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;

wherein one carbon in any cycloalkyl ring may be replaced with O, S or $NR^9$; and wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_nR^{11}$, —$COR^6$, —$NHR^6SO_2R^8$, —$OC(O)NR^6R^7$, —$N_3$, —$OC(O)OR^7$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$CO_2H$, aryl, heteroaryl and heterocyclyl;

alternatively, $R^3$ is —$OR^{3a}$, —$NR^{3a}R^{3b}$, —$NHR^{3a}$, —$SO_nR^{3a}$, —$SO_2NHR^{3a}$, —$SO_2NR^{3a}R^{3b}$, —$COR^{3a}$, —$CONHR^{3a}$, or —$CONR^{3a}R^{3b}$;

$R^{3a}$ and $R^{3b}$ are independently selected from $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl;

wherein one carbon in any cycloalkyl may be replaced with O, S or $NR^9$; and wherein each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, —SH, —$S(O)_nR^{11}$, —$COR^6$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$NHR^6SO_2R^8$, —$OC(O)NR^6R^7$, —$N_3$, —$OC(O)OR^7$, —$CONR^6R^7$, —$CO_2H$, aryl, heteroaryl and heterocyclyl;

$R^4$ is independently selected in each occurrence from —H, —$OR^{10}$, —$COR^9$, —$CO_2R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2R^8$, —$CONR^9R^{10}$, —CN, —$NR^9R^{10}$, —$S(O)_nR^{12}$, or halogen;

$A^1$ is CH;

$A^2$ is CH;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO(NOR^9)R^{11}$, —$CO_2R^8$, or —$S(O)_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

alternatively, two $R^5$ groups on adjacent atoms can form a 5–7 membered fused ring, partially saturated or unsaturated, optionally containing 1–2 —O— or —SO$_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —NO$_2$, halogen, —CN, —NR$^6$R$^7$, NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl ($C_1$–$C_4$ alkyl);

alternatively NR$^6$R$^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —NR$^6$R$^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{30}$, SH, —S(O)$_n$R$^{32}$, —COR$^{32}$, —CO$_2$R$^{32}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{32}$, —NR$^{29}$R$^{30}$, and —CONR$^{29}$R$^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

More preferred compounds of this invention are compounds of Formula (I-a) and pharmaceutically acceptable salts and pro-drug forms thereof, wherein:

W is (—H, —H);

Y is CH$_2$;

$R^1$ is a halogen;

$R^3$ is $C_1$–$C_{10}$ alkyl, $C_3$–$C_{10}$ cycloalkyl, $C_4$–$C_{12}$ cycloalkylalkyl, or $C_2$–$C_{10}$ alkoxyalkyl;

wherein one carbon in any cycloalkyl ring may be replaced with O, S or NR$^9$;

$R^4$ and $R^5$ are independently selected at each occurrence from —OR$^{10}$, halogen, $C_1$–$C_6$ alkyl, and $C_1$–$C_6$ haloalkoxy;

$A^1$ is CH;

$A^2$ is CH;

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl.

Even more preferred compounds of this invention are compounds of Formula (I-a) and pharmaceutically acceptable salts and pro-drug forms thereof, wherein:

W is (—H, —H);

Y is CH$_2$;

$R^1$ is a halogen;

$R^3$ is $C_1$–$C_{10}$ alkyl, $C_3$–$C_8$ cycloalkyl, $C_4$–$C_{12}$ cycloalkylalkyl, or $C_2$–$C_{10}$ alkoxyalkyl;

$R^4$ and $R^5$ are independently selected in each occurrence from —OR$^{10}$, halogen, $C_1$–$C_6$ alkyl, and $C_1$–$C_6$ haloalkoxy;

$A^1$ is CH;

$A^2$ is CH; and $R^{10}$ is independently at each occurrence selected from $C_0$–$C_4$ alkyl.

Specifically preferred compounds of this invention are compounds of Formula (I-a), pharmaceutically acceptable salts and pro-drug forms thereof, which are:

5-Chloro-1-(1-cyclopropylpropyl)-3-(5,7-dichloro-2,3-dihydro-1H-indol-1-yl)-2(1H)-pyrazinone;

5-Chloro-3-(5,7-dichloro-2,3-dihydro-1H-indol-1-yl)-1-[1-(methoxymethyl)propyl]-2(1H)-pyrazinone;

5-Chloro-3-(7-chloro-5-methoxy-2,3-dihydro-1H-indol-1-yl)-1-[1-(methoxymethyl)propyl]-2(1H)-pyrazinone;

5-Chloro-3-(7-chloro-5-methoxy-2,3-dihydro-1H-indol-1-yl)-1-(1-ethyl-3-methoxypropyl)-2(1H)-pyrazinone;

5-Chloro-3-(5-methoxy-7-methyl-2,3-dihydro-1H-indol-1-yl)-1-[1-(methoxymethyl)propyl]-2(1H)-pyrazinone;

5-Chloro-3-(7-bromo-5-methoxy-2,3-dihydro-1H-indol-1-yl)-1-[1-(methoxymethyl)propyl]-2(1H)-pyrazinone; and 5-Chloro-3-(7-bromo-5-methoxy-2,3-dihydro-1H-indol-1-yl)-1-(1-ethyl-3-methoxypropyl)-2(1H)-pyrazinone.

In another embodiment of preferred compounds of the present invention are compounds of Formula (I):

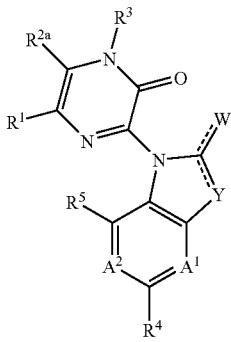

(I)

or a pharmaceutically acceptable salt form thereof, wherein:

W is (—H, —H);

Y is —CH$_2$—, —CH(CH$_3$)—, —C(CH$_3$)$_2$—, —CH$_2$CH$_2$—, or —OCH$_2$—;

R$^1$ is H, halogen, —CN, C$_1$–C$_2$ haloalkyl, —OR$^{10}$, C$_1$–C$_4$ alkyl, C$_2$–C$_4$ alkenyl, C$_2$–C$_4$ alkynyl, C$_3$–C$_4$ cycloalkyl, and C$_4$–C$_6$ cycloalkylalkyl;

wherein each C$_1$–C$_4$ alkyl, C$_2$–C$_4$ alkenyl, or C$_2$–C$_4$ alkynyl, is each optionally substituted with F, Cl, Br, CN, —OH, —CH$_3$, —OCH$_3$, —CF$_3$, or —OCF$_3$;

R$^{2a}$ is H, F, Cl, Br, —CN, —OH, —CH$_3$, —OCH$_3$, —CF$_3$, or —OCF$_3$;

R$^3$ is C$_1$–C$_8$ alkyl, C$_3$–C$_8$ alkenyl, C$_3$–C$_8$ alkynyl, C$_3$–C$_6$ cycloalkyl, C$_4$–C$_{10}$ cycloalkylalkyl, C$_2$–C$_{10}$ alkoxyalkyl, C$_5$–C$_6$ cycloalkenyl, or C$_6$–C$_{10}$ cycloalkenylalkyl;

wherein each C$_1$–C$_8$ alkyl, C$_3$–C$_8$ alkenyl, C$_3$–C$_8$ alkynyl, C$_3$–C$_6$ cycloalkyl, C$_4$–C$_{10}$ cycloalkylalkyl, C$_2$–C$_{10}$ alkoxyalkyl, C$_5$–C$_6$ cycloalkenyl, or C$_6$–C$_{10}$ cycloalkenylalkyl is optionally substituted with 1, 2 or 3 substituents independently selected at each occurrence from methyl, ethyl, cyclopropyl, cyclobutyl, F, Cl, Br, —CF$_3$, cyano, —OR$^7$, —S(O)$_n$R$^{11}$, —COR$^6$, —NHR$^6$SO$_2$R$^8$, —OC(O)NR$^6$R$^7$, —N$_3$, —OC(O)OR$^7$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, and —CO$_2$H;

alternatively, R$^3$ is —S(O)R$^{3a}$, —S(O)$_2$R$^{3a}$, —COR$^{3a}$, —CONHR$^{3a}$, or —CONR$^{3a}$R$^{3b}$;

R$^{3a}$ and R$^{3b}$ are independently selected from C$_1$–C$_8$ alkyl, C$_3$–C$_8$ alkenyl, C$_3$–C$_8$ alkynyl, C$_3$–C$_6$ cycloalkyl, C$_4$–C$_{10}$ cycloalkylalkyl, C$_2$–C$_{10}$ alkoxyalkyl, C$_5$–C$_6$ cycloalkenyl, or C$_6$–C$_{10}$ cycloalkenylalkyl;

wherein each C$_1$–C$_8$ alkyl, C$_3$–C$_8$ alkenyl, C$_3$–C$_8$ alkynyl, C$_3$–C$_6$ cycloalkyl, C$_4$–C$_{10}$ cycloalkylalkyl, C$_2$–C$_{10}$ alkoxyalkyl, C$_5$–C$_6$ cycloalkenyl, or C$_6$–C$_{10}$ cycloalkenylalkyl is optionally substituted with 1, 2 or 3 substituents independently selected at each occurrence from methyl, ethyl, methoxy, ethoxy, methyl-S—, ethyl-S—, cyclopropyl, cyclubutyl, F, Cl, —CF$_3$, and —OCF$_3$;

R$^4$ is —H, —OR$^{10}$, —COR$^9$, —CO$_2$R$^8$, —CONR$^9$R$^{10}$, —CN, —NR$^9$R$^{10}$, —S(O)$_n$R$^{12}$, —S(O)$_2$NR$^9$R$^{10}$, —NO$_2$, halogen, C$_1$–C$_4$ alkyl, C$_1$–C$_4$ haloalkyl, C$_1$–C$_4$ haloalkoxy, C$_3$–C$_6$ cycloalkyl, C$_2$–C$_4$ alkenyl, or C$_2$–C$_4$ alkynyl;

wherein C$_1$–C$_4$ alkyl, C$_1$–C$_4$ haloalkyl, C$_3$–C$_6$ cycloalkyl, C$_2$–C$_4$ alkenyl, or C$_2$–C$_4$ alkynyl, are optionally substituted with —OR$^{10}$, —COR$^9$, —CO$_2$R$^8$, —CONR$^9$R$^{10}$, —CN, —NR$^9$R$^{10}$, —S(O)$_n$R$^{12}$, or halogen;

A$^1$ is CR$^5$;

A$^2$ is CR$^5$;

R$^5$ is independently selected at each occurrence from —H, C$_1$–C$_6$ alkyl, C$_1$–C$_4$ haloalkyl, C$_1$–C$_4$ haloalkoxy, C$_2$–C$_6$ alkenyl, C$_2$–C$_6$ alkynyl, C$_3$–C$_6$ cycloalkyl, C$_4$–C$_{10}$ cycloalkylalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —CO(NOR$^9$)R$^{11}$, —CO$_2$R$^8$, —S(O)$_2$NR$^9$R$^{10}$, and —S(O)$_n$R$^{11}$;

wherein C$_1$–C$_6$ alkyl, C$_2$–C$_6$ alkenyl, C$_2$–C$_6$ alkynyl, C$_3$–C$_6$ cycloalkyl and C$_4$–C$_{10}$ cycloalkylalkyl are optionally substituted with 1 to 3 substituents independently selected at each occurrence from C$_1$–C$_4$ alkyl, C$_2$–C$_4$ alkenyl, C$_2$–C$_4$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, —NR$^6$COR$^7$, NR$^6$CO$_2$R$^8$, —COR$^6$, —OR$^7$, —CONR$^6$R$^7$, —CO$_2$R$^8$, —CO(NOR$^9$)R$^7$, and —S(O)$_n$R$^{11}$;

R$^6$ and R$^7$ are independently at each occurrence H, methyl, ethyl, propyl, or butyl;

R$^8$ is independently at each occurrence methyl, ethyl, propyl, or butyl;

R$^9$ and R$^{10}$ are independently at each occurrence selected from H, methyl, ethyl, propyl, or butyl;

R$^{11}$ is independently at each occurrence H, methyl, ethyl, propyl, butyl, or —NR$^6$R$^7$;

R$^{12}$ is independently at each occurrence methyl, ethyl, propyl, or butyl; and n is 0, 1, or 2.

Preferred compounds of this invention are compounds of Formula (I-b):

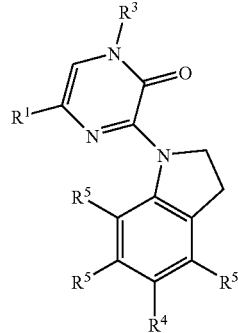

(I-b)

or a pharmaceutically acceptable salt form thereof, wherein:

R$^1$ is H, halogen, —CN, C$_1$–C$_2$ haloalkyl, —OR$^{10}$, or C$_1$–C$_3$ alkyl;

R$^3$ is C$_1$–C$_6$ alkyl, C$_3$–C$_6$ alkenyl, C$_3$–C$_6$ alkynyl, C$_3$–C$_6$ cycloalkyl, C$_4$–C$_7$ cycloalkylalkyl, C$_2$–C$_6$ alkoxyalkyl, C$_5$–C$_6$ cycloalkenyl, or C$_6$–C$_7$ cycloalkenylalkyl;

wherein each C$_1$–C$_6$ alkyl, C$_3$–C$_6$ alkenyl, C$_3$–C$_6$ alkynyl, C$_3$–C$_6$ cycloalkyl, C$_4$–C$_7$ cycloalkylalkyl, C$_2$–C$_6$ alkoxyalkyl, C$_5$–C$_6$ cycloalkenyl, or C$_6$–C$_7$ cycloalkenylalkyl is optionally substituted with 1 or 2 substituents independently selected at each occurrence from methyl, ethyl, methoxy, ethoxy, methyl-S—, ethyl-S—, cyclopropyl, cyclobutyl, F, Cl, —CF$_3$ and —OCF$_3$;

R$^4$ is —H, —OR$^{10}$, —CN, —NR$^9$R$^{10}$, —S(O)$_2$NR$^9$R$^{10}$, —NO$_2$, halogen, C$_1$–C$_4$ alkyl, C$_1$–C$_4$ haloalkyl, C$_1$–C$_4$ haloalkoxy, C$_2$–C$_4$ alkenyl, C$_2$–C$_4$ alkynyl, —SR$^{12}$, —S(O)$_2$R$^{12}$, or —S(O)$_2$R$^{12}$;

R$^5$ is independently at each occurrence —H, C$_1$–C$_4$ alkyl, C$_1$–C$_4$ haloalkyl, C$_1$–C$_4$ haloalkoxy, C$_2$–C$_4$ alkenyl, C$_2$–C$_4$ alkynyl, C$_3$–C$_4$ cycloalkyl, C$_4$–C$_5$ cycloalkylalkyl, —NO₂, halogen, —CN, —NR⁶R⁷, —NR⁶COR⁷, —NR⁶CO₂R⁸, —COR⁶—OR⁷, —CONR⁶R⁷. —S(O)₂NR⁹R¹⁰, —CO₂R⁸, —SCH₃, —SCH₂CH₃, —S(O)R¹¹, or —S(O)₂R¹¹;

R⁶ and R⁷ are independently at each occurrence H, methyl, or ethyl;

R⁸ is independently at each occurrence methyl or ethyl;

R⁹ and R¹⁰ are independently at each occurrence selected from H, methyl, or ethyl;

R¹¹ is independently at each occurrence methyl, ethyl, or —NR⁶R⁷; and

R¹² is independently at each occurrence methyl or ethyl.

More preferred compounds of this invention are compounds of Formula (I-c):

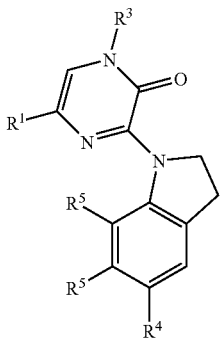

(I-c)

or a pharmaceutically acceptable salt form thereof, wherein:

R¹ is H, F, Cl, Br, —CN, methyl, ethyl, methoxy, or C₁–C₂ haloalkyl;

R³ is C₁–C₆ alkyl optionally substituted with 1 or 2 substituents independently selected at each occurrence from methyl, ethyl, methoxy, ethoxy, methyl-S—, ethyl-S—, cyclopropyl, cyclobutyl, and —CF₃;

R⁴ is —H, F, Cl, Br, —CN, methyl, ethyl, propyl, butyl, methoxy, ethoxy, propoxy, C₁–C₂ haloalkyl, or C₁–C₂ haloalkoxy; and R⁵ is independently at each occurrence —H, F, Cl, Br, —CN, methyl, ethyl, propyl, butyl, methoxy, ethoxy, propoxy, C₁–C₂ haloalkyl, or C₁–C₂ haloalkoxy.

Even more preferred compounds of this invention are compounds of Formula (I-c):

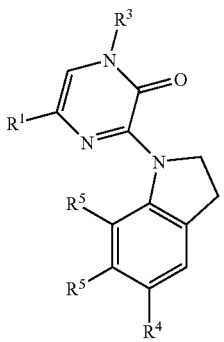

(I-c)

or a pharmaceutically acceptable salt form thereof, wherein:
or a pharmaceutically acceptable salt form thereof, wherein:

R¹ is H, F, Cl, Br, methyl, ethyl, —CN, or —CF₃;

R³ is butyl-, pentyl-, hexyl-, heptyl-, methoxy-ethyl-, methoxy-propyl-, methoxy-butyl-, methoxy-pentyl-, methoxy-hexyl-, methylthio-ethyl-, methylthio-propyl-, methylthio-butyl-, methylthio-pentyl-, methylthio-hexyl-, 1-cyclopropyl-propyl-, 1-cyclopropyl-butyl-, 1-cyclopropyl-pentyl-, 1-cyclobutyl-propyl-, 1-cyclobutyl-butyl-, 1-cyclobutyl-pentyl, 1-cyclopropyl-1-(CF₃)-methyl-, 1-cyclopropyl-2-(CF₃)-ethyl-, 1-cyclopropyl-3-(CF₃)-propyl-, 1-cyclobutyl-1-(CF₃)-methyl-, 1-cyclobutyl-2-(CF₃)-ethyl-, or 1-cyclobutyl-3-(CF₃)-propyl-;

R⁴ is H, methyl-, ethyl-, methoxy-, ethoxy-, isopropoxy-, n-propoxy-, F, Cl, Br, —CF₃, —OCF₃, —OCHF₂, —CN; and R⁵ is independently at each occurrence, —H, methyl, ethyl, methoxy, ethoxy, F, Cl, Br, or —CF₃.

Specifically preferred compounds of this invention are compounds of Formula (I), and pharmaceutically acceptable salts thereof, which are:

5-Chloro-3-(5,7-dichloro-2,3-dihydro-1H-indol-1-yl)-1-(1-ethylpropyl)-2(1H)-pyrazinone;

5-Chloro-3-(5,7-dichloro-2,3-dihydro-1H-indol-1-yl)-1-(1-ethyl-3-methoxypropyl)-2(1H)-pyrazinone;

5-Chloro-1-(1-ethylpropyl)-3-(5-methoxy-7-methyl-2,3-dihydro-1H-indol-1-yl)-2(1H)-pyrazinone;

3-(7-Bromo-5-methoxy-2,3-dihydro-1H-indol-1-yl)-5-chloro-1-(1-ethylpropyl)-2(1H)-pyrazinone;

3-(5,7-Dichloro-2,3-dihydro-1H-indol-1-yl)-1-(1-ethylpropyl)-5-methyl-2(1H)-pyrazinone;

3-(5-Methoxy-7-methyl-2,3-dihydro-1H-indol-1-yl)-1-(1-ethylpropyl)-5-methyl-2(1H)-pyrazinone;

5-Chloro-3-(7-chloro-5-methoxy-2,3-dihydro-1H-indol-1-yl)-1-(1-methylpropyl)-2(1H)-pyrazinone;

-3-(7-Bromo-5-methoxy-2,3-dihydro-1H-indol-1-yl)-5-chloro-1-(1-methylpropyl)-2(1H)-pyrazinone;

5-Chloro-3-(5-methoxy-7-methyl-2,3-dihydro-1H-indol-1-yl)-1-(1-methylpropyl)-2(1H)-pyrazinone;

5-Chloro-3-(5,7-dichloro-2,3-dihydro-1H-indol-1-yl)-1-(1-methylpropyl)-2(1H)-pyrazinone;

5-Bromo-3-(7-bromo-5-methoxy-2,3-dihydro-1H-indol-1-yl)-1-(1-ethylpropyl)-2(1H)-pyrazinone;

5-Bromo-1-(1-ethylpropyl)-3-(5-methoxy-7-methyl-2,3-dihydro-1H-indol-1-yl)-2(1H)-pyrazinone;

5-Bromo-3-(5,7-dichloro-2,3-dihydro-1H-indol-1-yl)-1-(1-ethylpropyl)-2(1H)-pyrazinone;

5-Chloro-3-(7-chloro-5-methoxy-2,3-dihydro-1H-indol-1-yl)-1-[(1R)-1-cyclopropylpropyl]-2(1H)-pyrazinone;

3-(7-Bromo-5-methoxy-2,3-dihydro-1H-indol-1-yl)-5-chloro-1-[(1R)-1-cyclopropylpropyl]-2(1H)-pyrazinone;

5-Chloro-1-[(1R)-1-cyclopropylpropyl]-3-(5-methoxy-7-methyl-2,3-dihydro-1H-indol-1-yl)-2(1H)-pyrazinone;

5-Chloro-1-[(1R)-1-cyclopropylpropyl]-3-(5,7-dichloro-2,3-dihydro-1H-indol-1-yl)-2(1H)-pyrazinone;

5-Chloro-1-[(1R)-1-cyclopropylpropyl]-3-(5,7-dibromo-2,3-dihydro-1H-indol-1-yl)-2(1H)-pyrazinone;

5-Chloro-3-(7-chloro-6-fluoro-5-methoxy-2,3-dihydro-1H-indol-1-yl)-1-[(1R)-1-cyclopropylpropyl]-2(1H)-pyrazinone;

5-Chloro-3-(7-chloro-5-methoxy-2,3-dihydro-1H-indol-1-yl)-1-[(1S)-1-cyclopropylpropyl]-2(1H)-pyrazinone;

3-(7-Bromo-5-methoxy-2,3-dihydro-1H-indol-1-yl)-5-chloro-1-[(1S)-1-cyclopropylpropyl]-2(1H)-pyrazinone;

5-Chloro-1-[(1S)-1-cyclopropylpropyl]-3-(5-methoxy-7-methyl-2,3-dihydro-1H-indol-1-yl)-2(1H)-pyrazinone;

5-Chloro-1-[(1S)-1-cyclopropylpropyl]-3-(5,7-dichloro-2,3-dihydro-1H-indol-1-yl)-2(1H)-pyrazinone;

5-Chloro-1-[(1S)-1-cyclopropylpropyl]-3-(5,7-dibromo-2,3-dihydro-1H-indol-1-yl)-2(1H)-pyrazinone;
5-Chloro-3-(7-chloro-6-fluoro-5-methoxy-2,3-dihydro-1H-indol-1-yl)-1-[(1S)-1-cyclopropylpropyl]-2(1H)-pyrazinone;
5-Chloro-3-(5,7-dichloro-2,3-dihydro-1H-indol-1-yl)-1-[(1R)-2-methoxy-1-methylethyl]-2(1H)-pyrazinone;
5-Chloro-3-(5,7-dibromo-2,3-dihydro-1H-indol-1-yl)-1-[(1R)-2-methoxy-1-methylethyl]-2(1H)-pyrazinone;
5-Chloro-3-(7-chloro-6-fluoro-5-methoxy-2,3-dihydro-1H-indol-1-yl)-1-[1-(methoxymethyl)propyl]-2(1H)-pyrazinone;
3-(7-Bromo-5-methoxy-2,3-dihydro-1H-indol-1-yl)-5-chloro-1-[(1R)-1-(methoxymethyl)propyl]-2(1H)-pyrazinone;
5-Chloro-3-(5,7-dichloro-2,3-dihydro-1H-indol-1-yl)-1-[(1R)-1-(methoxymethyl)propyl]-2(1H)-pyrazinone;
5-Bromo-3-(7-bromo-5-methoxy-2,3-dihydro-1H-indol-1-yl)-1-[(1R)-1-(methoxymethyl)propyl]-2(1H)-pyrazinone;
5-Bromo-3-(5-methoxy-7-methyl-2,3-dihydro-1H-indol-1-yl)-1-[(1R)-1-(methoxymethyl)propyl]-2(1H)-pyrazinone;
5-Bromo-3-(5,7-dichloro-2,3-dihydro-1H-indol-1-yl)-1-[(1R)-1-(methoxymethyl)propyl]-2(1H)-pyrazinone;
5-Bromo-3-(7-chloro-6-fluoro-5-methoxy-2,3-dihydro-1H-indol-1-yl)-1-[(1R)-1-(methoxymethyl)propyl]-2(1H)-pyrazinone;
3-(7-Bromo-5-methoxy-2,3-dihydro-1H-indol-1-yl)-5-chloro-1-[(1S)-1-(methoxymethyl)propyl]-2(1H)-pyrazinone;
5-Chloro-3-(5,7-dichloro-2,3-dihydro-1H-indol-1-yl)-1-[(1S)-1-(methoxymethyl)propyl]-2(1H)-pyrazinone;
5-Bromo-3-(5,7-dichloro-2,3-dihydro-1H-indol-1-yl)-1-[(1S)-1-(methoxymethyl)propyl]-2(1H)-pyrazinone;
5-Chloro-3-(5-methoxy-7-methyl-2,3-dihydro-1H-indol-1-yl)-1-[2-methyl-1-(1-methylethyl)propyl]-2(1H)-pyrazinone;
3-(7-Bromo-5-methoxy-2,3-dihydro-1H-indol-1-yl)-5-chloro-1-[2-(methylthio)ethyl]-2(1H)-pyrazinone;
5-Chloro-3-(5-methoxy-7-methyl-2,3-dihydro-1H-indol-1-yl)-1-[2-(methylthio)ethyl]-2(1H)-pyrazinone;
5-Chloro-3-(5,7-dichloro-2,3-dihydro-1H-indol-1-yl)-1-[2-(methylthio)ethyl]-2(1H)-pyrazinone;
5-Chloro-3-(7-chloro-5-methoxy-2,3-dihydro-1H-indol-1-yl)-1-(1-ethylpropyl)-6-methyl-2(1H)-pyrazinone;
5-Chloro-3-(7-chloro-5-methoxy-2,3-dihydro-1H-indol-1-yl)-1-(1-cyclobutylpropyl)-6-methyl-2(1H)-pyrazinone;
3-(5-Bromo-7-chloro-2,3-dihydro-1H-indol-1-yl)-5-chloro-1-methylpropyl-2(1H)-pyrazinone;
3-(5,7-Dichloro-2,3-dihydro-1H-indol-1-yl)-5-ethyl-1-(1-ethylpropyl)-2(1H)-pyrazinone;
3-(5-Bromo-7-chloro-2,3-dihydro-1H-indol-1-yl)-5-chloro-1-(1-ethylpropyl)-2(1H)-pyrazinone;
6-(5,7-Dichloro-2,3-dihydro-1H-indol-1-yl)-4-(1-ethylpropyl)-4,5-dihydro-5-oxo-2-pyrazinecarbonitrile;
3-(5-Bromo-7-chloro-2,3-dihydro-1H-indol-1-yl)-5-chloro-1-[(1R)-1-cyclopropylpropyl]-2(1H)-pyrazinone;
3-(5-Bromo-7-chloro-2,3-dihydro-1H-indol-1-yl)-5-chloro-1-[(1S)-1-cyclopropylpropyl]-2(1H)-pyrazinone;
5-Chloro-3-(7-chloro-5-methoxy-2,3-dihydro-1H-indol-1-yl)-1-[(1R)-1-(methoxymethyl)propyl]-2(1H)-pyrazinone;
5-Chloro-3-(5-methoxy-7-methyl-2,3-dihydro-1H-indol-1-yl)-1-[(1R)-1-(methoxymethyl)propyl]-2(1H)-pyrazinone;
1-[6-Chloro-4-[(1R)-1-(methoxymethyl)propyl]-3,4-dihydro-3-oxopyrazinyl]-5-methoxy-2,3-dihydro-1H-indole-7-carbonitrile;
5-Bromo-3-(5-bromo-7-chloro-2,3-dihydro-1H-indol-1-yl)-1-[(1R)-1-(methoxymethyl)propyl]-2(1H)-pyrazinone;
3-(5-Bromo-7-chloro-2,3-dihydro-1H-indol-1-yl)-5-chloro-1-[(1S)-1-(methoxymethyl)propyl]-2(1H)-pyrazinone; and
5-Chloro-3-(7-chloro-5-methoxy-2,3-dihydro-1H-indol-1-yl)-1-(1-cyclobutylpropyl)-2(1H)-pyrazinone.

More preferred compounds of this invention are compounds of Formula (I-d):

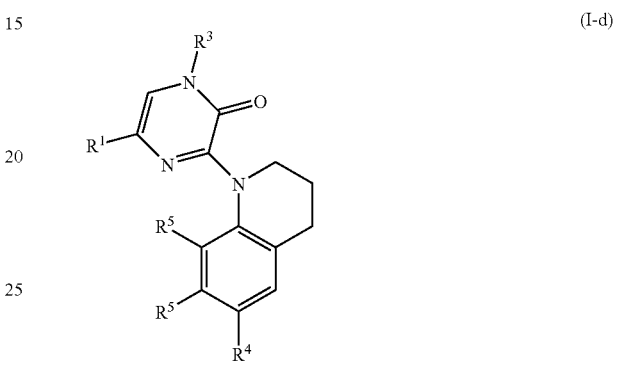

(I-d)

or a pharmaceutically acceptable salt form thereof, wherein:
$R^1$ is H, F, Cl, Br, —CN, methyl, ethyl, methoxy, or $C_1$–$C_2$ haloalkyl;
$R^3$ is $C_1$–$C_6$ alkyl optionally substituted with 1 or 2 substituents independently selected at each occurrence from methyl, ethyl, methoxy, ethoxy, methyl-S—, ethyl-S—, cyclopropyl, cyclobutyl, and —$CF_3$;
$R^4$ is —H, F, Cl, Br, —CN, methyl, ethyl, propyl, butyl, methoxy, ethoxy, propoxy, $C_1$–$C_2$ haloalkyl, or $C_1$–$C_2$ haloalkoxy; and
$R^5$ is independently at each occurrence —H, F, Cl, Br, —CN, methyl, ethyl, propyl, butyl, methoxy, ethoxy, propoxy, $C_1$–$C_2$ haloalkyl, or $C_1$–$C_2$ haloalkoxy.

Even more preferred compounds of this invention are compounds of Formula (I-d):

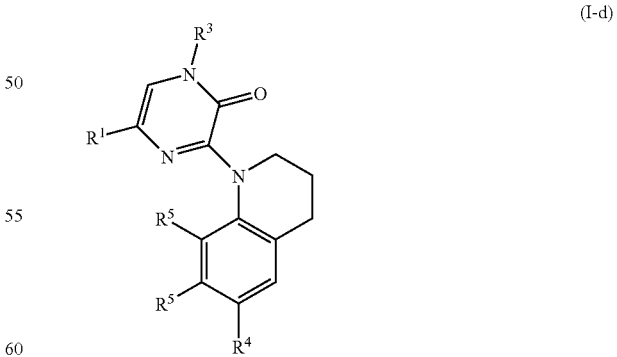

(I-d)

or a pharmaceutically acceptable salt form thereof, wherein:
$R^1$ is H, F, Cl, Br, methyl, ethyl, —CN, or —$CF_3$;
$R^3$ is butyl-, pentyl-, hexyl-, heptyl-, methoxy-ethyl-, methoxy-propyl-, methoxy-butyl-, methoxy-pentyl-, methoxy-hexyl-, methylthio-ethyl-, methylthio-propyl-, methylthio-butyl-, methylthio-pentyl-, methylthio-hexyl-, 1-cyclopropyl-propyl-, 1-cyclopropyl-butyl-, 1-cyclopropyl-pentyl-, 1-cyclobutyl-propyl-, 1-cyclobutyl-butyl-, 1-cyclobutyl-pentyl, 1-cyclopropyl-1-($CF_3$)-methyl-, 1-cyclopropyl-2-($CF_3$)-ethyl-, 1-cyclopropyl-3-($CF_3$)-propyl-, 1-cyclobutyl-1-($CF_3$)-methyl-, 1-cyclobutyl-2-($CF_3$)-ethyl-, or 1-cyclobutyl-3-($CF_3$)-propyl-;

$R^4$ is H, methyl-, ethyl-, methoxy-, ethoxy-, isopropoxy-, n-propoxy-, F, Cl, Br, —$CF_3$. —$OCF_3$, —$OCHF_2$, —CN; and $R^5$ is independently at each occurrence, —H, methyl, ethyl, methoxy, ethoxy, F, Cl, Br, or —$CF_3$.

Specifically preferred compounds of this invention are compounds of Formula (I), and pharmaceutically acceptable salts thereof, which are:

3-(8-Bromo-6-methoxy-1,2,3,4-tetrahydroquinoline)-5-chloro-1-(1-ethylpropyl)-2(1H)-pyrazinone;

3-(8-Bromo-6-methoxy-1,2,3,4-tetrahydroquinoline)-5-chloro-1-[(1R)-1-cyclopropylpropyl]-2(1H)-pyrazinone;

3-(8-Bromo-6-methoxy-1,2,3,4-tetrahydroquinoline)-5-chloro-1-[(1S)-1-cyclopropylpropyl]-2(1H)-pyrazinone;

3-(8-Bromo-6-methoxy-1,2,3,4-tetrahydroquinoline)-5-chloro-1-[(1R)-2-methoxy-1-methylethyl]-2(1H)-pyrazinone;

5-Bromo-3-(8-bromo-6-methoxy-1,2,3,4-tetrahydroquinoline)-1-[(1R)-1-(methoxymethyl)propyl]-2(1H)-pyrazinone; and 3-(8-Bromo-6-methoxy-1,2,3,4-tetrahydroquinoline)-5-chloro-1-[(1S)-1-(methoxymethyl)propyl]-2(1H)-pyrazinone.

More preferred compounds of this invention are compounds of Formula (I-e):

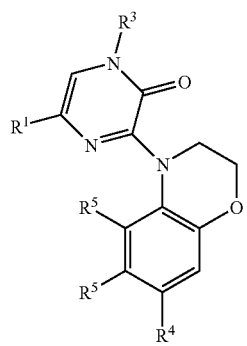

(I-e)

or a pharmaceutically acceptable salt form thereof, wherein:
$R^1$ is H, F, Cl, Br, —CN, methyl, ethyl, methoxy, or $C_1$–$C_2$ haloalkyl;

$R^3$ is $C_1$–$C_6$ alkyl optionally substituted with 1 or 2 substituents independently selected at each occurrence from methyl, ethyl, methoxy, ethoxy, methyl-S—, ethyl-S—, cyclopropyl, cyclobutyl, and —$CF_3$;

$R^4$ is —H, F, Cl, Br, —CN, methyl, ethyl, propyl, butyl, methoxy, ethoxy, propoxy, $C_1$–$C_2$ haloalkyl, or $C_1$–$C_2$ haloalkoxy; and $R^5$ is independently at each occurrence —H, F, Cl, Br, —CN, methyl, ethyl, propyl, butyl, methoxy, ethoxy, propoxy, $C_1$–$C_2$ haloalkyl, or $C_1$–$C_2$ haloalkoxy.

Even more preferred compounds of this invention are compounds of Formula (I-e):

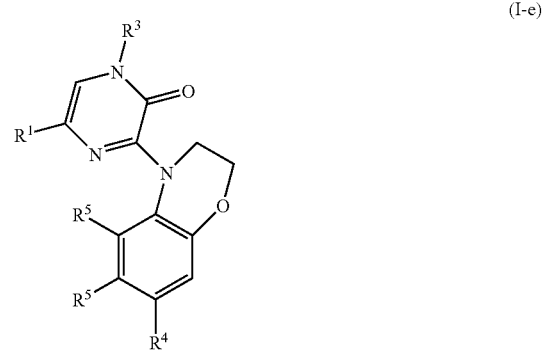

(I-e)

or a pharmaceutically acceptable salt form thereof, wherein:
$R^1$ is H, F, Cl, Br, methyl, ethyl, —CN, or —$CF_3$;

$R^3$ is butyl-, pentyl-, hexyl-, heptyl-, methoxy-ethyl-, methoxy-propyl-, methoxy-butyl-, methoxy-pentyl-, methoxy-hexyl-, methylthio-ethyl-, methylthio-propyl-, methylthio-butyl-, methylthio-pentyl-, methylthio-hexyl-, 1-cyclopropyl-propyl-, 1-cyclopropyl-butyl-, 1-cyclopropyl-pentyl-, 1-cyclobutyl-propyl-, 1-cyclobutyl-butyl-, 1-cyclobutyl-pentyl, 1-cyclopropyl-1-($CF_3$)-methyl-, 1-cyclopropyl-2-($CF_3$)-ethyl-, 1-cyclopropyl-3-($CF_3$)-propyl-, 1-cyclobutyl-1-($CF_3$)-methyl-, 1-cyclobutyl-2-($CF_3$)-ethyl-, or 1-cyclobutyl-3-($CF_3$)-propyl-;

$R^4$ is H, methyl-, ethyl-, methoxy-, ethoxy-, isopropoxy-, n-propoxy-, F, Cl, Br, —$CF_3$, —$OCF_3$, —$OCHF_2$, —CN; and $R^5$ is independently at each occurrence, —H, methyl, ethyl, methoxy, ethoxy, F, Cl, Br, or —$CF_3$.

Specifically preferred compounds of this invention are compounds of Formula (I), and pharmaceutically acceptable salts thereof, which are:

3-(5-Bromo-7-methoxy-2,3-dihydro-4H-1,4-benzoxazin-4-yl)-5-chloro-1-[(1R)-1-cyclopropylpropyl]-2(1H)-pyrazinone;

3-(5-Bromo-7-methoxy-2,3-dihydro-4H-1,4-benzoxazin-4-yl)-5-chloro-1-(1-cyclobutylpropyl)-2(1H)-pyrazinone;

3-(5-Bromo-7-methoxy-2,3-dihydro-4H-1,4-benzoxazin-4-yl)-5-chloro-1-(1-cyclobutylpropyl)-2(1H)-pyrazinone;

3-(5-Bromo-7-methoxy-2,3-dihydro-4H-1,4-benzoxazin-4-yl)-5-chloro-1-[(1S)-1-cyclopropylpropyl]-2(1H)-pyrazinone;

3-(5-Bromo-7-methoxy-2,3-dihydro-4H-1,4-benzoxazin-4-yl)-5-chloro-1-[(1R)-(1-methoxymethyl)propyl]-2(1H)-pyrazinone;

3-(5-Bromo-7-methoxy-2,3-dihydro-4H-1,4-benzoxazin-4-yl)-5-chloro-1-[(1S)-(1-methoxymethyl)propyl]-2(1H)-pyrazinone;

3-(5-Bromo-7-methoxy-2,3-dihydro-4H-1,4-benzoxazin-4-yl)-5-chloro-1-[(1S)-2-methoxy-1-methylethyl]-2(1H)-pyrazinone;

5-chloro-1-(1-cyclobutylpropyl)-3-(7-methoxy-2,3-dihydro-4H-1,4-benzoxazin-4-yl)-2(1H)-pyrazinone;

5-chloro-1-[(1R)-1-cyclopropylpropyl]-3-(7-methoxy-2,3-dihydro-4H-1,4-benzoxazin-4-yl)-2(1H)-pyrazinone; and 3-(5-Bromo-7-methoxy-2,3-dihydro-4H-1,4-benzoxazin-4-yl)-5-chloro-1-[(1R)-1-(methoxymethyl)propyl]-2(1H)-pyrazinone.

A second embodiment of preferred compounds of this invention are compounds of Formula (II):

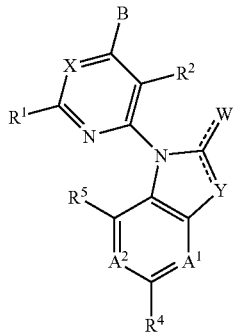

(II)

or a pharmaceutically acceptable salt or pro-drug form thereof, wherein:

X is N;
W is (—H, —H);
Y is $CH_2$;
B is $NHR^3$;
$R^1$ is independently, at each occurrence, selected from H, halogen, —CN, $C_1$–$C_4$ haloalkyl, —$NR^9R^{10}$, —$NR^9COR^9$, —$COR^{10}$, —$OR^{10}$, SH, —$S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;

wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, —$NR^9R^{10}$, —$NR^9COR^9$, —$COR^{10}$, —$OR^{10}$, SH or —$S(O)_nR^{12}$;

$R^2$ is H, halogen, CN, $C_1$–$C_4$ haloalkyl, —$COR^{10}$, —$OR^{10}$, SH, —$S(O)_nR^{12}$, $C_1$–$C_4$ alkyl, $C_3$–$C_6$ cycloalkyl, or $C_4$–$C_7$ cycloalkylalkyl;

wherein each $C_1$–$C_4$ alkyl, $C_3$–$C_6$ cycloalkyl, or $C_4$–$C_7$ cycloalkylalkyl is optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;

$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;

wherein one carbon in any cycloalkyl ring may be replaced with O, S or $NR^9$; and wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_nR^{11}$, —$COR^6$, —$NHR^6SO_2R^8$, —$OC(O)NR^6R^7$, —$N_3$, —$OC(O)OR^7$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$CO_2H$, aryl, heteroaryl and heterocyclyl;

$R^4$ is independently selected in each occurrence from —H, —$OR^{10}$, —$COR^9$, —$CO_2R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2R^8$, —$CONR^9R^{10}$, —CN, —$NR^9R^{10}$, —$S(O)_nR^{12}$, or halogen;

$A^1$ are CH;
$A^2$ are CH;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO(NOR^9)R^{11}$, —$CO_2R^8$, or —$S(O)_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

alternatively, two $R^5$ groups on adjacent atoms can form a 5–7 membered fused ring, partially saturated or unsaturated, optionally containing 1–2 —O— or —$SO_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl ($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_nR^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S $—(O)_nR^{32}$, $—COR^{32}$, $—CO_2R^{28}$, $—OC(O)R^{32}$, $—NR^{29}COR^{29}$, $—N(COR^{32})_2$, $—NR^{29}CONR^{29}R^{30}$, $—NR^{29}CO_2R^{28}$, $—NR^{29}R^{30}$, and $—CONR^{29}R^{30}$;

heterocyclyl is saturated or partially saturated heteroaryl, optionally substituted with 1 to 3 substituents independently selected at each occurrence from $C_1–C_6$ alkyl, $C_3–C_6$ cycloalkyl, $C_4–C_7$ cycloalkylalkyl, $C_2–C_6$ alkenyl, $C_2–C_6$ alkynyl, halogen, $C_1–C_4$ haloalkyl, cyano, $—OR^{30}$, SH, $—S(O)_nR^{32}$, $—COR^{32}$, $—CO_2R^{32}$, $—OC(O)R^{32}$, $—NR^{29}COR^{29}$, $—N(COR^{32})_2$, $—NR^{29}CONR^{29}R^{30}$, $—NR^{29}CO_2R^{32}$, $—NR^{29}R^{30}$, and $—CONR^{29}R^{30}$;

$R^{28}$ is independently at each occurrence $C_1–C_4$ alkyl, $C_1–C_4$ haloalkyl, $C_3–C_6$ cycloalkyl, $C_4–C_{12}$ cycloalkylalkyl, phenyl, or phenyl($C_1–C_4$ alkyl)-;

$R^{29}$ and $R^{30}$ are independently at each occurrence selected from H, $C_1–C_4$ alkyl, $C_1–C_4$ haloalkyl, $C_3–C_6$ alkenyl, $C_3–C_6$ alkynyl, $C_3–C_6$ cycloalkyl, $C_2–C_6$ alkoxyalkyl, and $C_4–C_7$ cycloalkylalkyl;

$R^{32}$ is independently at each occurrence $C_1–C_4$ alkyl, $C_1–C_4$ haloalkyl, $C_3–C_6$ alkenyl, $C_3–C_6$ alkynyl, $C_3–C_6$ cycloalkyl, or $C_4–C_7$ cycloalkylalkyl; and n is 0, 1, or 2.

More preferred compounds of the second embodiment of this invention are compounds of Formula (II) and pharmaceutically acceptable salts and pro-drug forms thereof, wherein:
X is N;
W is (—H, —H);
Y is $CH_2$;
B is $NHR^3$;
$R^1$ is $C_1–C_6$ alkyl;
$R^2$ is H, halogen, CN, or $—COR^{10}$;
$R^4$ and $R^5$ are independently selected in each occurrence $—OR^{10}$, halogen, or $C_1–C_6$ haloalkoxy;
$A^1$ and $A^2$ are CH; and
$R^{10}$ is H.

Specifically preferred compounds of the second embodiment of this invention are compounds of Formula (II), pharmaceutically acceptable salts and pro-drug forms thereof, which are:

4-(5,7-dichloro-2,3-dihydro-1H-indol-1-yl)-6-(1-ethylpropylamino)-2-methylpyrimidine;
5-chloro-4-(5,7-dichloro-2,3-dihydro-1H-indol-1-yl)-6-(1-ethylpropylamino)-2-methylpyrimidine;
5-bromo-4-(5,7-dichloro-2,3-dihydro-1H-indol-1-yl)-6-(1-ethylpropylamino)-2-methylpyrimidine;
4-(5,7-dichloro-2,3-dihydro-1H-indol-1-yl)-6-(1-ethylpropylamino)-5-iodo-2-methylpyrimidine;
5-cyano-4-(5,7-dichloro-2,3-dihydro-1H-indol-1-yl)-6-(1-ethylpropylamino)-2-methylpyrimidine;
4-(5,7-dichloro-2,3-dihydro-1H-indol-1-yl)-6-(1-ethylpropylamino)-5-formyl-2-methylpyrimidine;
4-(5,7-dichloro-2,3-dihydro-1H-indol-1-yl)-6-(1-ethylpropylamino)-5-hydroxymethyl-2-methylpyrimidine;
4-(7-chloro-5-methoxy-2,3-dihydro-1H-indol-1-yl)-6-(1-ethylpropylamino)-2-methylpyrimidine;
4-(7-chloro-5-methoxy-2,3-dihydro-1H-indol-1-yl)-5-cyano-6-(1-ethylpropylamino)-2-methylpyrimidine;
4-(7-chloro-5-methoxy-2,3-dihydro-1H-indol-1-yl)-6-(1-ethylpropylamino)-5-formyl-2-methylpyrimidine;
4-(7-chloro-5-methoxy-2,3-dihydro-1H-indol-1-yl)-6-[1-(1-ethyl-3-methoxy)propylamino]-2-methylpyrimidine;
4-(7-chloro-5-methoxy-2,3-dihydro-1H-indol-1-yl)-6-[1-(1-ethyl-3-methoxy)propylamino]-5-iodo-2-methylpyrimidine;
4-(7-chloro-5-methoxy-2,3-dihydro-1H-indol-1-yl)-5-cyano-6-[1-(1-ethyl-3-methoxy)propylamino]-2-methylpyrimidine;
4-(7-chloro-5-methoxy-2,3-dihydro-1H-indol-1-yl)-6-[1-(1-methoxymethyl)propylamino]-2-methylpyrimidine;
4-(7-chloro-5-methoxy-2,3-dihydro-1H-indol-1-yl)-5-iodo-6-[1-(1-methoxymethyl)propylamino]-2-methylpyrimidine;
4-(7-chloro-5-methoxy-2,3-dihydro-1H-indol-1-yl)-5-cyano-6-[1-(1-methoxymethyl)propylamino]-2-methylpyrimidine;
4-(7-chloro-5-methoxy-2,3-dihydro-1H-indol-1-yl)-5-formyl-6-[1-(1-methoxymethyl)propylamino]-2-methylpyrimidine;
4-(7-chloro-5-methoxy-2,3-dihydro-1H-indol-1-yl)-6-(1-methylbutylamino)-2-methylpyrimidine;
4-(7-chloro-5-methoxy-2,3-dihydro-1H-indol-1-yl)-6-(1-methylpropylamino)-2-methylpyrimidine; and
4-(7-chloro-5-methoxy-2,3-dihydro-1H-indol-1-yl)-6-[1-(1-cyclobutyl)ethylamino]-2-methylpyrimidine.

A third embodiment of preferred compounds of this invention are compounds of Formula (II) and pharmaceutically acceptable salts and pro-drug forms thereof, wherein:
X is $CR^1$;
W is (—H, —H);
Y is $CH_2$;
B is $NHR^3$;
$R^1$ is independently, at each occurrence, selected from H, halogen, —CN, $C_1–C_4$ haloalkyl, $—NR^9R^{10}$, $—NR^9COR^9$, $—COR^{10}$, $—OR^{10}$, SH, $—S(O)_nR^{12}$, $C_1–C_6$ alkyl, $C_2–C_6$ alkenyl, $C_2–C_6$ alkynyl, $C_3–C_6$ cycloalkyl, and $C_4–C_8$ cycloalkylalkyl;
wherein each $C_1–C_6$ alkyl, $C_2–C_6$ alkenyl, $C_2–C_6$ alkynyl, $C_3–C_6$ cycloalkyl, or $C_4–C_8$ cycloalkylalkyl is each optionally substituted with halogen, CN, $C_1–C_4$ haloalkyl, $—NR^9R^{11}$, $—NR^9COR^9$, $—COR^{10}$, $—OR^{10}$, SH or $—S(O)_nR^{12}$;
$R^2$ is H, halogen, CN, $C_1–C_4$ haloalkyl, $—COR^{10}$, $—OR^{10}$, SH, $—S(O)_nR^{12}$, $C_1–C_4$ alkyl, $C_3–C_6$ cycloalkyl, or $C_4–C_7$ cycloalkylalkyl;
wherein each $C_1–C_4$ alkyl, $C_3–C_6$ cycloalkyl, or $C_4–C_7$ cycloalkylalkyl is optionally substituted with halogen, —CN, $C_1–C_4$ haloalkyl, $—NR^9R^{10}$, $—NR^9COR^9$, $—COR^{10}$, $—OR^{10}$, SH or $—S(O)_nR^{12}$;
$R^3$ is $C_1–C_{10}$ alkyl, $C_3–C_{10}$ alkenyl, $C_3–C_{10}$ alkynyl, $C_3–C_8$ cycloalkyl, $C_4–C_{12}$ cycloalkylalkyl, $C_2–C_{10}$ alkoxyalkyl, $C_5–C_{10}$ cycloalkenyl, or $C_6–C_{10}$ cycloalkenylalkyl;
wherein one carbon in any cycloalkyl ring may be replaced with O, S or $NR^9$; and
wherein each $C_1–C_{10}$ alkyl, $C_3–C_{10}$ alkenyl, $C_3–C_8$ alkynyl, $C_3–C_8$ cycloalkyl, $C_4–C_{12}$ cycloalkylalkyl, $C_2–C_{10}$ alkoxyalkyl, $C_5–C_{10}$ cycloalkenyl, or $C_6–C_{10}$ cycloalkenylalkyl is optionally substituted with 1, 2 or 3 substituents independently selected at each occurrence from $C_1–C_6$ alkyl, $C_2–C_6$ alkenyl, $C_2–C_{10}$ alkynyl, $C_3–C_6$ cycloalkyl, halogen, $C_1–C_4$ haloalkyl, cyano, $—OR^7$, SH, $—S(O)_nR^{11}$, $—COR^6$, $—NHR^6SO_2R^8$, $—OC(O)NR^6R^7$, $—N_3$, $—OC(O)OR^7$, $—CO_2R^8$, $—OC(O)R^6$, $—NR^7COR^6$, $—N(COR^6)_2$, $—NR^7CONR^6R^7$, $—NR^7CO_2R^8$, $—NR^6R^7$, $—CONR^6R^7$, $—CO_2H$, aryl, heteroaryl and heterocyclyl;
$R^4$ is independently selected in each occurrence from —H, $—OR^{10}$, $—COR^9$, $—CO_2R^8$, $—CONR^9R^{10}$, —CN, $—NR^9R^{10}$, $—S(O)_nR^{12}$, halogen, $C_1–C_6$ alkyl, $C_1–C_4$ haloalkyl, $C_1–C_6$ haloalkoxy, $C_3–C_6$ cycloalkyl, $C_2–C_6$ alkenyl, $C_2–C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2R^8$, —$CONR^9R^{10}$, —CN, —$NR^9R^{10}$, —$S(O)_nR^{12}$, or halogen;

$A^1$ are CH;

$A^2$ are CH;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO(NOR^9)R^{11}$, —$CO_2R^8$, or —$S(O)_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

alternatively, two $R^5$ groups on adjacent atoms can form a 5–7 membered fused ring, partially saturated or unsaturated, optionally containing 1–2 —O— or —$SO_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$-$Cl_{12}$ bis(alkoxy) alkyl, aryl, aryl($C_1$–$C_4$ alkyl)-, heteroaryl or heteroaryl ($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_nR^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_nR^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, SH, —$S(O)_nR^{32}$, —$COR^{32}$, —$CO_2R^{32}$, —$OC(O)R^{32}$, —$NR^{29}COR^{29}$, —$N(COR^{32})_2$, —$NR^{29}CONR^{29}R^{30}$, —$NR^{29}CO_2R^{32}$, —$NR^{29}R^{30}$, and —$CONR^{29}R^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

In a fourth embodiment the present invention provides for a pharmaceutical composition comprising a compound of Formula (I), (I-a), (I-b), or (I-c) and a pharmaceutically acceptable carrier.

Also provided herein is a pharmaceutical composition comprising a compound of Formula (II) and a pharmaceutically acceptable carrier.

In a fifth embodiment the present invention provides for a method of treating a mammal afflicted with affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis or hypoglycemia which method comprises administering to the mammal a therapeutically effective dose of a pharmaceutical composition provided herein.

In a preferred embodiment the present invention provides for a method of treating a mammal afflicted with anxiety or depression.

In a more preferred embodiment the present invention provides for a method of treating a mammal afflicted with anxiety.

In a more preferred embodiment the present invention provides for a method of treating a mammal afflicted with depression.

In a fifth embodiment, the present invention provides a compound of Formula (I), (I-a), (I-b), (I-c) or (II) for use in therapy.

In a preferred embodiment the present invention provides a compound of Formula (I), (I-a), (I-b), (I-c) or (II) for use in therapy of anxiety or depression.

In a sixth embodiment, the present invention provides for the use of a compound of Formula (I), (I-a), (I-b), (I-c) or (II) for the manufacture of a medicament for the treatment of anxiety or depression.

DEFINITIONS

Many compounds of this invention have one or more assymetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms or a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e. =O), then 2 hydrogens on the atom are replaced. Unsubstituted atoms bear all of the hydrogen atoms dictated by their valency. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

When any variable (e.g. $R^5$) may optionally be substituted with more than one substituent (e.g. 1 to 3), the selection of substituent, at each occurrence, is independent of every other occurrence. Thus, for example, if variable $R^5$ is optionally substituted with 1 to 3 defined substituents, then said variable $R^5$ may be substituted with 0, 1, 2 or 3 defined substituents and those defined substituents are independently selected from the defined Markush group of available substituents. Also, combinations of substituents and/or variables are permissible only if such combinations result in stable compounds.

Similarly, when a group of substituents (e.g. alkyl, alkenyl, alkynyl, cycloalkyl, and cycloalkylalkyl) may optionally be substituted with more than one substituent (e.g. 1 to 3), then each substituent of the group, as specified, may optionally be substituted as defined. Thus, for example, as used herein: $C_1$–$C_6$ alkyl, $C_2$–$C_6$ alkenyl, $C_2$–$C_6$ alkynyl, $C_3$–$C_6$ cycloalkyl, and/or $C_4$–$C_7$ cycloalkylalkyl may optionally be substituted with 1 to 3 defined substituents, is intended to mean $C_1$–$C_6$ alkyl may optionally be substituted as defined, $C_2$–$C_6$ alkenyl may optionally be substituted as defined, $C_2$–$C_6$ alkynyl may optionally be substituted as defined, and so on. Combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. "Alkoxyalkyl" represents an alkoxy group, as defined herein, attached through an alkyl group, as defined above, with the indicated number of carbon atoms. For example, "$C_2$–$C_6$ alkoxyalkyl" includes ($C_1$–$C_5$ alkoxy)methyl, ($C_1$–$C_4$ alkoxy)ethyl, ($C_1$–$C_3$ alkoxy)propyl, ($C_1$–$C_2$ alkoxy)butyl, and ($C_1$ alkoxy)pentyl. For example, "$C_2$–$C_6$ alkoxyalkyl" includes methoxymethyl, methoxyethyl, methoxypropyl, methoxybutyl, methoxypentyl, ethoxymethyl, ethoxyethyl, ethoxypropyl, ethoxybutyl, propoxymethyl, propoxyethyl, and the like.

"Halo" or "halogen" as used herein refers to fluoro, chloro, bromo, and iodo. Unless otherwise specified, preferred halo is fluoro, chloro, and bromo.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like.

"Cycloalkyl" is intended to include saturated ring groups, having the specified number of carbon atoms. For example, "$C_3$–$C_6$ cycloalkyl" denotes cyclopropyl, cyclobutyl, cyclopentyl, or cyclohexyl. "Cycloalkylalkyl" represents a cycloalkyl group, as defined herein, attached through an alkyl group, as defined above, with the indicated number of carbon atoms. For example, "$C_4$–$C_8$ cycloalkylalkyl" includes, but is not limited to, ($C_3$–$C_6$ cycloalkyl)methyl, ($C_3$–$C_6$ cycloalkyl)ethyl, ($C_3$–$C_5$ cycloalkyl)propyl, and ($C_3$–$C_4$ cycloalkyl)butyl. For example, "$C_4$–$C_8$ cycloalkylalkyl" includes, but is not limited to, cyclopropylmethyl, cyclopropylethyl, cyclopropylpropyl, cyclopropylbutyl, cyclopropylpentyl, cyclobutylmethyl, cyclobutylethyl, cyclobutylpropyl, cyclopentylmethyl, cyclopentylethyl, cyclopentylpropyl, cyclohexylmethyl, and the like.

"Cycloalkenyl" is intended to include partially unsaturated ring groups, having the specified number of carbon atoms. For example, "$C_5$–$C_{10}$ cycloalkenyl" includes, but is not limited to, cyclopentenyl, cyclohexenyl, cyclohexa-1,3-dienyl, cycloheptenyl, and the like. "Cycloalkenylalkyl" represents a cycloalkenyl group, as defined herein, attached through an alkyl group, as defined above, with the indicated number of carbon atoms.

As used herein, the term "aryl" or "$C_6$–$C_{10}$ aryl" is intended to mean either the 6-carbon benzene ring or the condensed 6-carbon rings of other aromatic derivatives containing the specified number of carbon atoms (see, e.g., *Hawley's Condensed Chemical Dictionary* (13 ed.), R. J. Lewis, ed., J. Wiley & Sons, Inc., New York (1997)). Aryl groups include, without limitation, phenyl, napthyl, indanyl and indenyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)$ H, CN, $NO_2$, $OCF_3$, $C(=O)CH_3$, $CO_2H$, or $CO_2CH_3$.

As used herein, the term "heterocycle" or "heterocyclyl" is intended to mean a stable 5- to 7-membered monocyclic ring or 7- to 14-membered bicyclic ring system which is saturated or partially saturated (partially unsaturated), and which consists of carbon atoms and 1, 2, 3 or 4 heteroatoms independently selected from the group consisting of N, O and S. Bicyclic heterocycles is intended to include saturated or partially saturated monocyclic heterocyclyl rings fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle is greater than 1, then these S and O heteroatoms are not adjacent to one another; i.e. there are no S—S, S—O, or O—O bonds in the heterocycle. It is preferred that the total number of S and O atoms in the heterocycle is not more than 1.

As used herein, the term "heteroaryl" is intended to mean a stable 5- to 6-membered monocyclic ring or 9- to 10-membered bicyclic ring system which is fully unsaturated (aromatic), unless otherwise specified in the claims, and which consists of carbon atoms and 1, 2, 3 or 4 heteroatoms independently selected from the group consisting of N, O and S. The nitrogen and sulfur heteroatoms may optionally be oxidized. The heteroaryl may be attached to its pendant group at any heteroatom or carbon atom which results in a stable structure. The heteroaryl rings described herein may be substituted on carbon or on a nitrogen atom if the resulting compound is stable. If specifically noted, a nitrogen in the heteroaryl may optionally be quaternized. It is preferred that when the total number of S and O atoms in the heteroaryl is greater than 1, then these S and O heteroatoms are not adjacent to one another; i.e. there are no S—S, S—O, or O—O bonds in the heteroaryl. It is preferred that the total number of S and O atoms in the heteroaryl is not more than 1.

Examples of heterocycles (heterocyclyls) and heteroaryls include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heteroaryls include, without limitation: pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, and indazolyl.

As used herein, compounds of Formula (I-a), (I) or (II) contain a bicyclic group of formula:

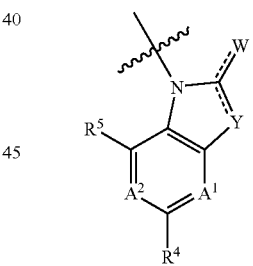

wherein W, as defined in the claims may be =O, =S, —H or (H,H); and Y, as defined in the claims can be —C(=O)—, —$CH_2$—, —$CH_2CH_2$—, —$OCH_2$—, —$SO_nCH_2$—, —N=, —$NR_Y$—, —O—, or —CH=. It is understood by one skilled in the art that the dashed line in the bicyclic group can not form two double bonds. For example, when W is =O or =S (forming a C=O or C=S bond with the bicyclic ring) then Y is not —N= or —CH=. When W is —H (forming a C—H bond with the bicyclic ring) then Y is —N=or —CH=. Lastly, when W is (H,H), then W forms two C—H bonds with the bicyclic group, i.e. a —$CH_2$— moiety, and Y is not —N=or —CH=. It is intended that combinations of substituents and/or variables are permissible only if such combinations result in stable compounds.

Examples wherein W is (H,H), include, but are not limited to:

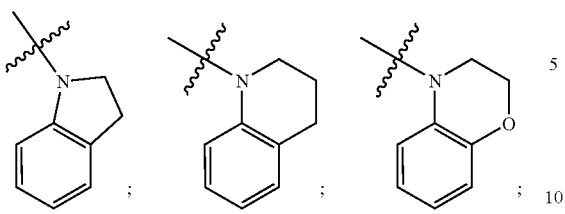

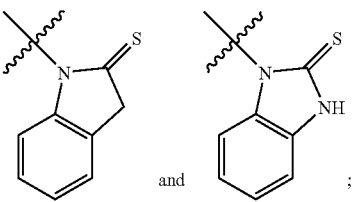

each subtituted by $R^y$, $R^4$ and $R^5$, respectively.

Examples wherein W is —H, include, but are not limited to:

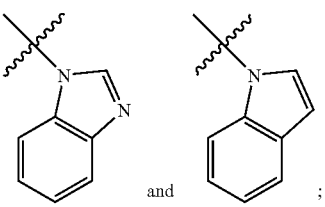

each subtituted by $R^4$ and $R^5$, respectively.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

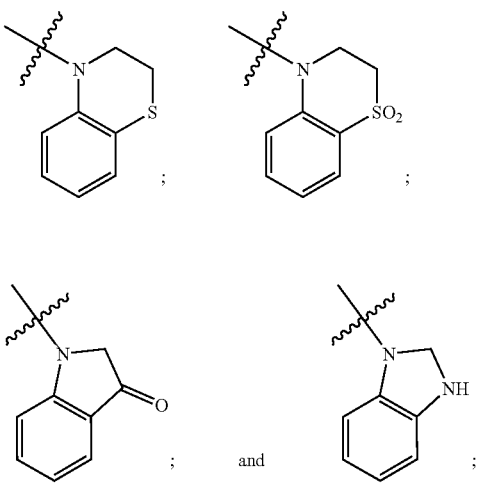

each subtituted by $R^y$, $R^4$ and $R^5$, respectively.

Examples wherein W is (H,H), and $A^1$ and/or $A^2$ are N include, but are not limited to:

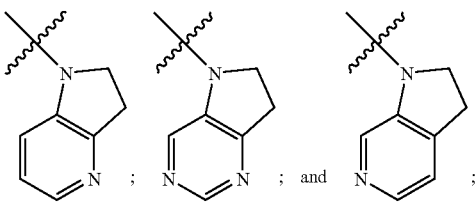

each subtituted by $R^y$, $R^4$ and $R^5$, respectively.

Examples wherein W is C=O, include, but are not limited to:

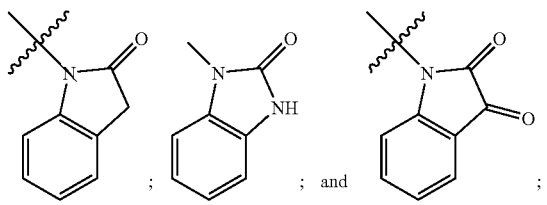

each subtituted by $R^y$, $R^4$ and $R^5$, respectively.

Examples wherein W is C=S, include, but are not limited to:

Pharmaceutically acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are considered to be any covalently bonded carriers which release the active parent drug of Formula (I-a) and (II) in vivo when such prodrug is administered to a mammalian subject. Prodrugs of the compounds of Formula (I-a) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the compounds of Formula (I-a) and (II), and the like.

The term "therapeutically effective amount" of a compound of this invention means an amount effective to antagonize abnormal level of CRF or treat the symptoms of affective disorder, anxiety or depression in a host.

Compounds provided herein can be prepared, for example and without limitation, by the following synthetic schemes outlined below (Schemes 1–3):

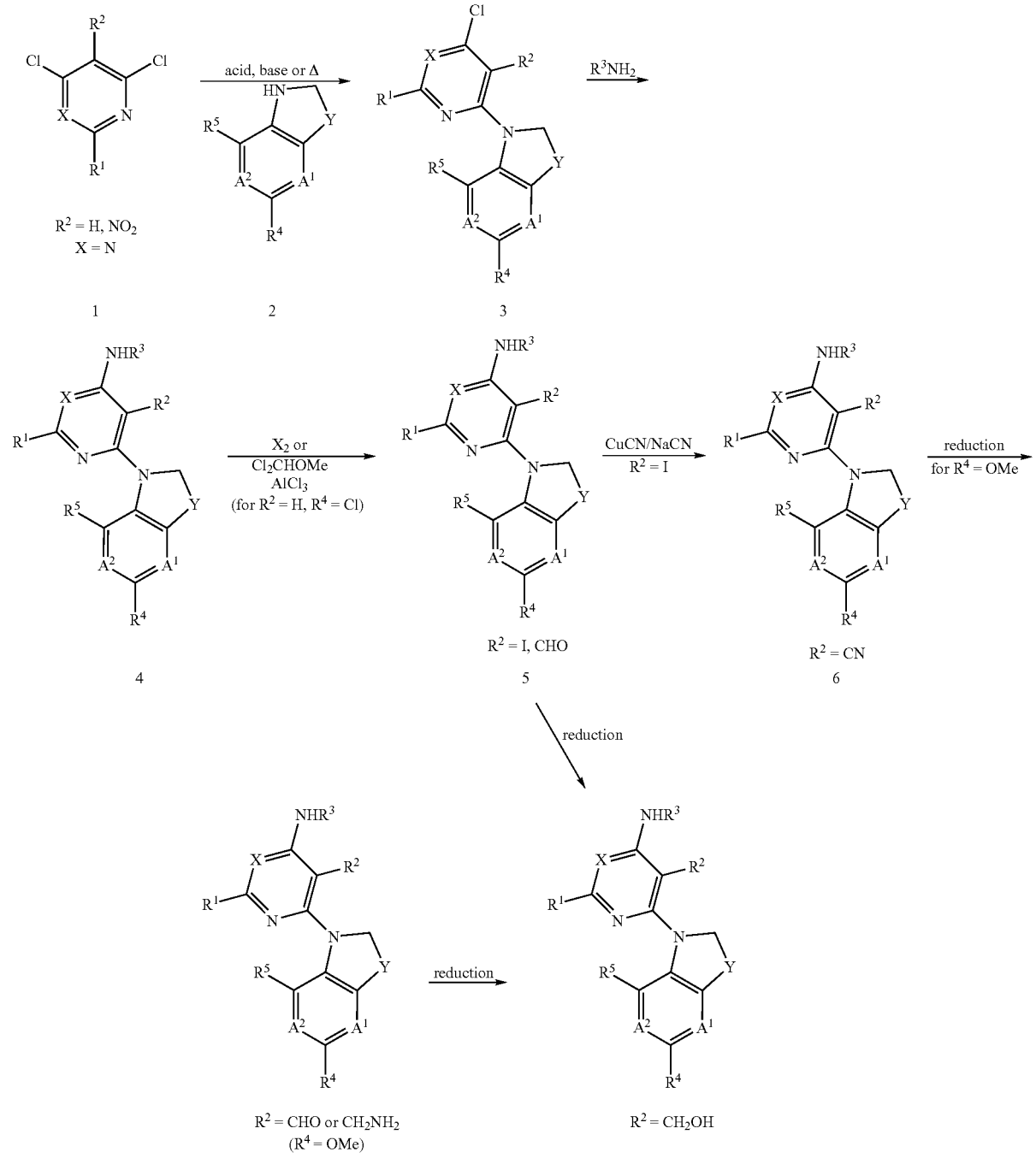

A 4,6-dicloropyrimidine 1 was coupled with a heterocyclic amine 2 to give the corresponding adduct 3, under thermal conditions, by action of a base such as sodium hydride, sodium potassium, or lithium hexamethyldisilazide, sodium or potassium metal, lithium diisopropylamide or a related base in a solvent such as THF, dimethoxyethane, ether, DMF, or DMSO; or an acid such as HCl or p-toluensulfonic acid. A primary or secondary amine was added to 3 to give the aminopyrimidine 4. The 5-unsubstituted pyrimidine analogs ($R^2$=H) could be halogenated on the 5-position to give compounds of compound 5 ($R^2$=halogen) by the action of a halogenating agent such as $Cl_2$, $Br_2$, $I_2$, N-chloro, N— bromo or N-iodosuccinimide. The 5-iodopyrimidines of compound 5 ($R^2$=I) were further transformed to the corresponding 5-cyano derivative of compound 6 ($R^2$=CN) by the action of CuCN or CuCN/NaCN. The cyano group could be reduced to give 5-formyl or 5-aminomethyl derivatives of compound 7 ($R^2$=CHO, $R^4$=OMe).

The 5-pyrimidine position of compounds of compound 4 ($R^2$=H, $R^4$=Cl) could be formylated directly by the action of dichloromethylmethyl ether in the presence of a Lewis acid such as an $AlCl_3$, $TiCl_4$, $SnCl_4$, etc. to give compounds of compound 5 ($R^2$=CHO, $R^3$=Cl). The 5-formylpyrimidines of compounds 5 and 7 were further transformed to the corresponding 5-hydroxymethyl derivatives by the action of a reducing agent such as $NaBH_4$.

Compounds of Formula (II) may be synthesized as described in Scheme 2.

Coupling a suitably substituted aniline having an ortho —Br, —I, or —$OSO_2CF_3$ group with a pyrimidine of compound 1 under base, acid or thermal catalysis gave the coupled product of compound 9. The central nitrogen of 9 was reacted with a cinnamomyl halide in the presence of an amine base such as triethyl amine or pyridine in an aprotic solvent to give 10.

This compound in turn may be subjected to a palladium-catalyzed ring closure (see: Larock, R. C et. al. *Tetrahedron Let.*, 1987, 44, 5291) to give compounds of compound 11, which when subjected to hydrolysis conditions afforded compounds of Formula (II) (W=O, Y=$CH_2$).

Alternatively the same analogs can be synthesized from intermediate of compound 12 as described by Tamura, Y. et. al. *Synthesis*, 1981, 534, to give 13, which upon desulfuration (see Tamura Y. et. al. *Chem. Pharm. Bull.* 1984, 32, 1995) can give compounds of Formula (II).

Scheme 2

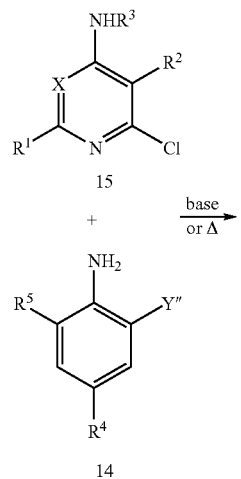

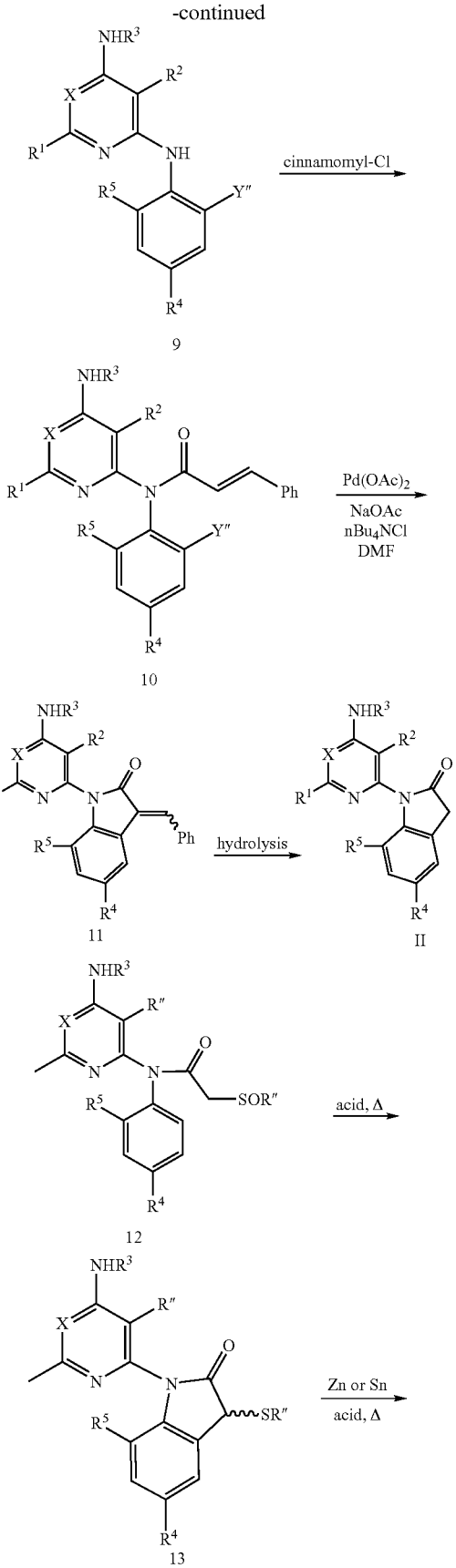

-continued

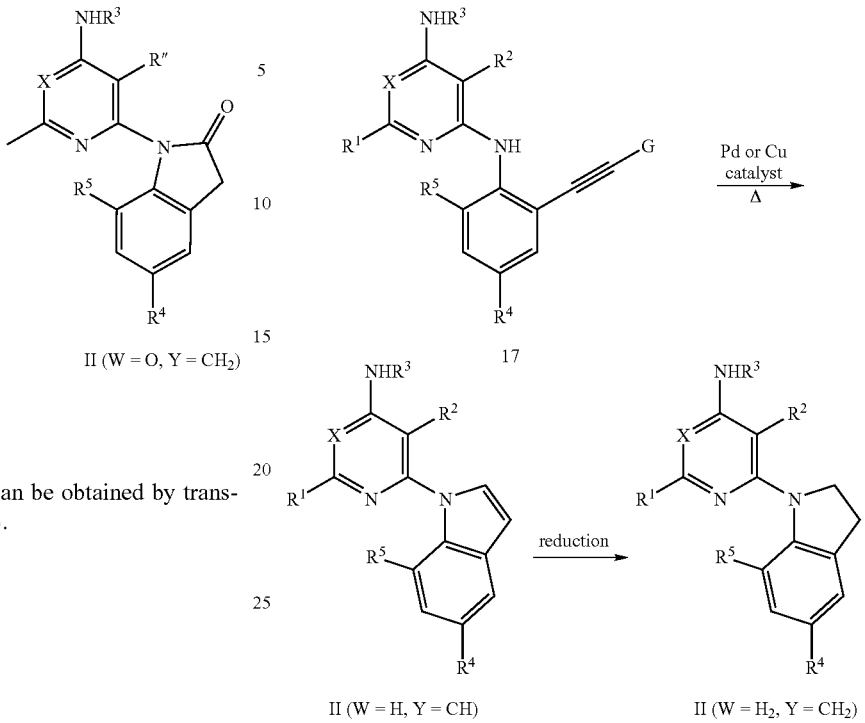

Analogs with the Formula (II) can be obtained by transformations described on Scheme 3.

Scheme 3

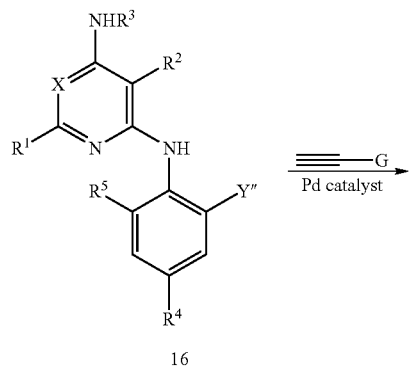

Reaction of compounds of compound 16 with a suitably substituted acetylene using a suitable palladium catalyst such as, but not limited to $Pd(PPh_3)_2Cl_2$, $Pd(PPh_3)_2Br_2$, $Pd(PPh_3)_4$ etc. (see: Heck, R. F. et. al. *Acc. Chem. Res.*, 1979, 12, 146) may provide the corresponding acetylenic aryls of compound 17. Depending on the original substitution on the acetylene, compounds of compound 17 can be converted to the 2-alkylindole analogs (Formula (II) in which W=H, Y=CH), or the indolinones (Formula II in which W=H, Y=CH).

The pyrazinones of this invention can be prepared by one of the general Schemes 4–10 outlined herein.

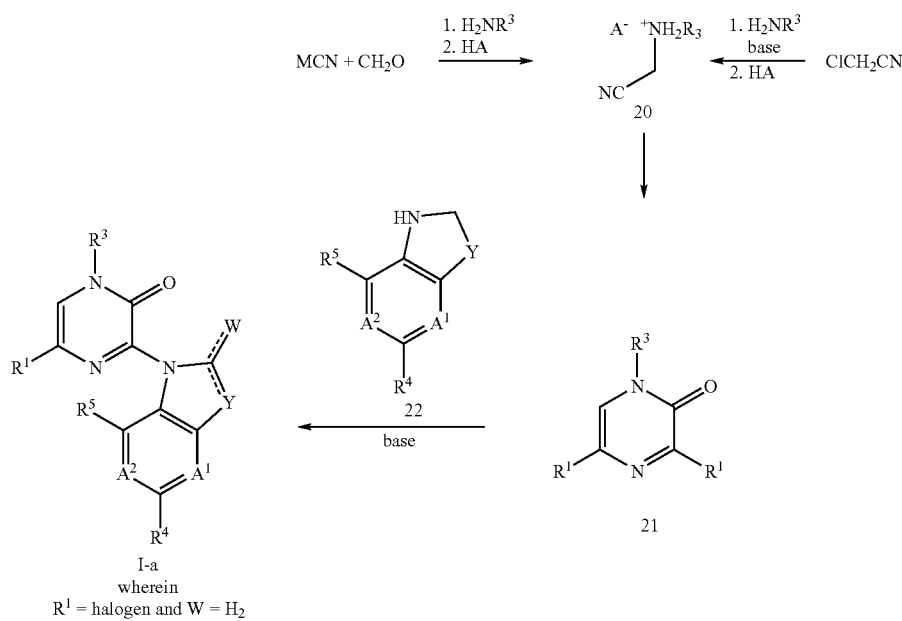

Compounds of the Formula (I-a) wherein $R^1$=halogen can be prepared as shown in Scheme 4. Reaction of a cyanide salt with formaldehyde and the appropriate substituted amine afforded the corresponding aminoacetonitrile which was purified as the hydrochloride salt of compound 20. Alternatively the same compounds of compound 20 can be synthesized by reaction of the amine $H_2NR^3$ with a haloacetonitrile, such as chloroacetonitrile, in the presence of a base such as a tertiary amine or an inorganic base such as $K_2CO_3$ in an organic solvent and isolated as a salt of an inorganic acid by treatment with that acid. Amine salt of compound 20 was treated with an oxalyl halide, $R^1COCOR^1$, such as oxalyl chloride or bromide to afford the dihalo compound 21, as described in Vekemans, J.; Pollers-Wieers, C.; Hoornaert, G. *J. Heterocyclic Chem.* 20, 919, (1982). Compound 21 can be coupled with a secondary amine of compound 22 in the presence of a strong base such as NaH, $KN(SiMe_3)_2$, $LiN(SiMe_3)_2$ or $NaN(SiMe_3)_2$ in an aprotic organic solvent, or under acid catalysis to give compounds of Formula (I-a).

presence of a palladium catalyst, such as $Pd(PPh_3)_2Cl_2$, to give compounds of compound 24. Condensation of compounds of compound 24 with a secondary amine of compound 22 under thermal, base, or acid catalyzed conditions gives compounds of Formula (I-a). Alternatively intermediates of compound 24 may be oxidized to the corresponding sulfones with an oxidant such as $KMnO_4$ and then condensed with the secondary amines of compound 22 to give (I-a). The use of appropriately substituted aluminum alkyls, or simple transformations of those substituted alkyls can give access to compounds of Formula (I-a), where $R^1$ is a substituted alkyl; see Ratovelomanana, V.; Linstrumelle, G.; *Tet. Letters* 52, 6001 (1984) and references cited therein. Alternatively, compounds of Formula (I-a) wherein $R^1$=alkyl or substituted alkyl can be directly synthesized from compounds of Formula (I-a) wherein $R^1$=halogen as shown in Scheme 6 using the same synthetic methods described for the conversion of 23 to 24 shown in Scheme 5.

Scheme 5

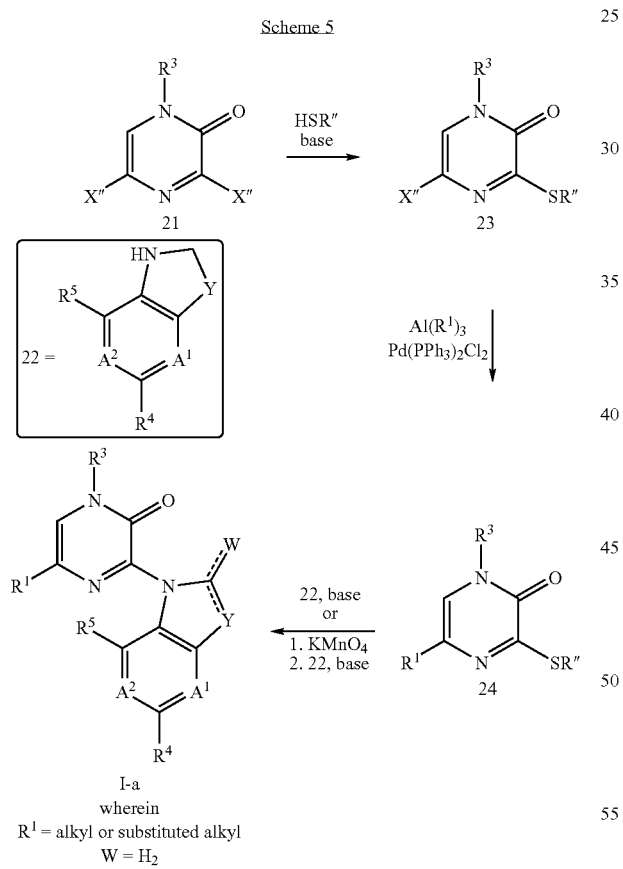

Scheme 6

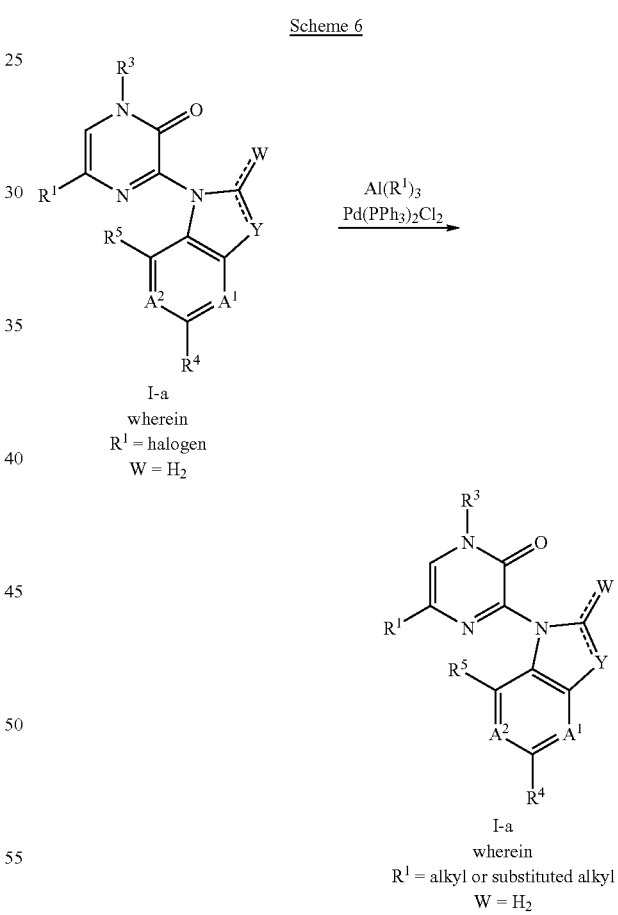

Compounds of the Formula (I-a) wherein $R^1$=alkyl or substituted alkyl can be prepared according to Scheme 5. Reaction of the intermediate of compound 21 in Scheme 4, wherein $R^1$=X"=halogen in Scheme 5, with an alkyl or aryl thiol, HSR", in the presence of base such as NaH affords the adduct of compound 23, which may then be treated with a trialkylaluminum as described in Hirota, K.; Kitade, Y.; Kanbe, Y.; Maki, Y.; *J. Org. Chem.* 57, 5268, (1992), in the In Scheme 7, reaction of an aminoacetonitrile salt 20, described in Scheme 4, with an oxalyl halide ester 30 gives the corresponding amide 31, which in turn can be converted to the corresponding imidate salt 32. This can be cyclized under treatment with a base, such as $K_2CO_3$ or $Et_3N$ to the pyrazinedione of compound 33. This can be converted to the corresponding halide 36, using a halogenating agent such as $POX"_3$, oxalyl halide or $SOX"_2$. Alternatively, 33 can be converted to the corresponding mesylate, tosylate or triflate, by treatment with the corresponding mesyl, tosyl, or triflic anhydride. Subsequently, 36 can be coupled with a secondary amine of compound 22 to give the corresponding adduct of compound 37, under the conditions described in Scheme 4.

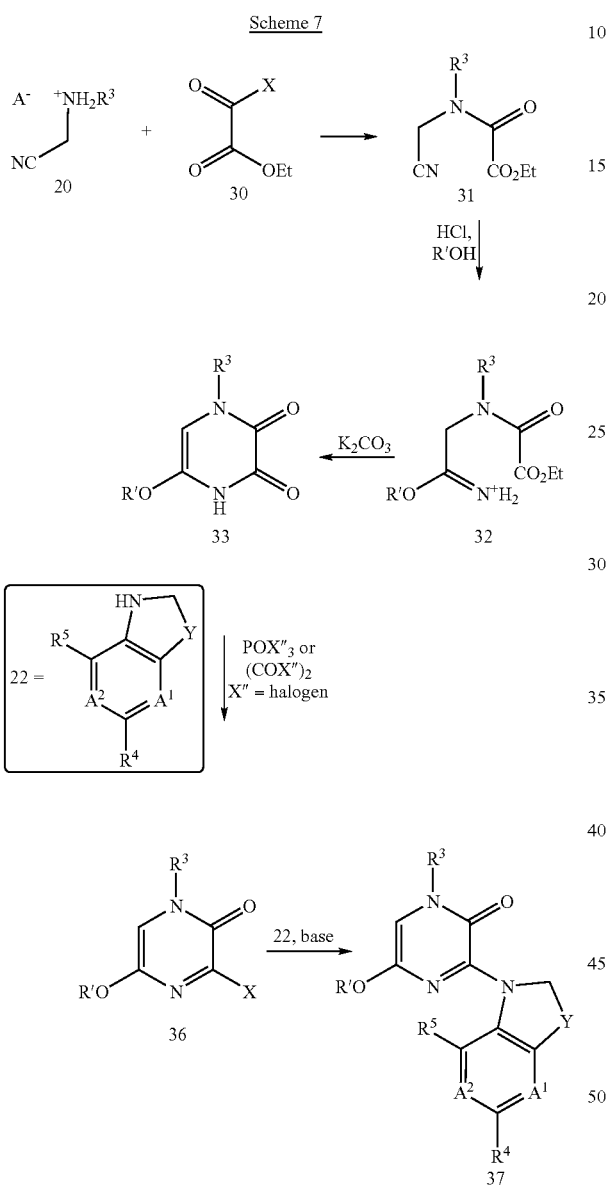

Scheme 7

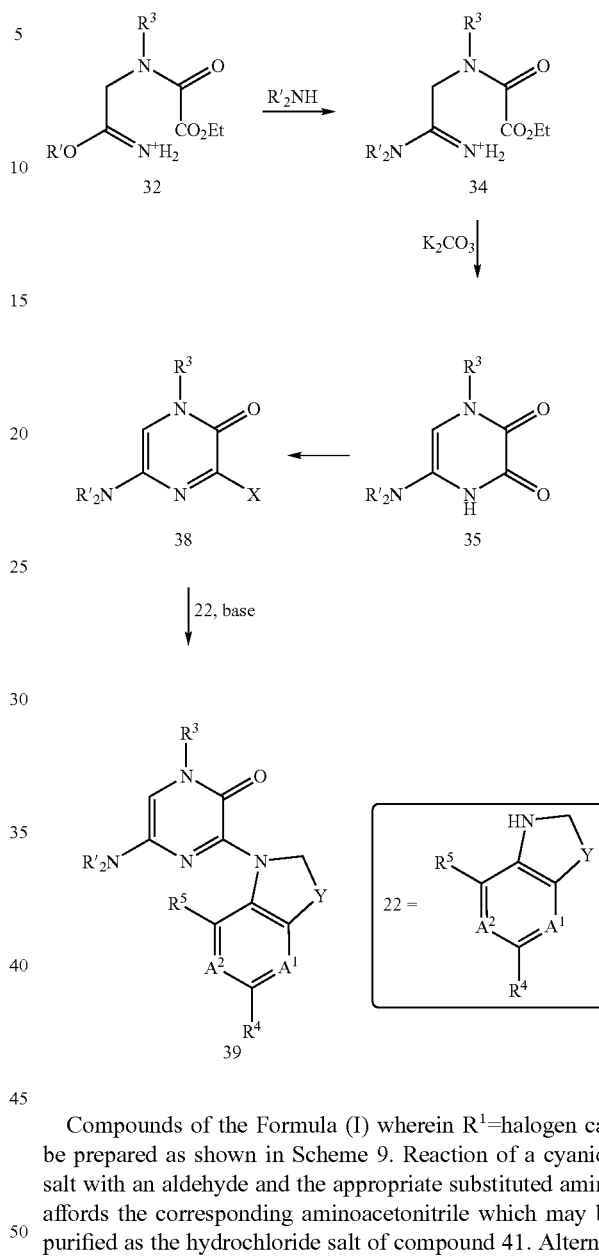

Scheme 8

Compounds of Formula (I-a) wherein $R^1$=COR$^{10}$ or CO$^2$R$^{10}$ can be synthesized from compounds of formula 23 by coupling with the appropriate vinyl aluminum or boron reagent in the presence of a palladium catalyst, such as Pd(PPh$_3$)$_2$Cl$_2$, and further transformations of the vinyl group, using methods known to one skilled in the art.

Compounds of Formula (I-a) wherein $R^1$=substituted N can be introduced on compounds of formula 32 by reaction with an amine to form the corresponding amidate 34 according to Scheme 8. Subsequently, 34 can be cyclized, halogenated, and substituted with the appropriate secondary amine 22 as described in Scheme 7 above.

Compounds of the Formula (I) wherein $R^1$=halogen can be prepared as shown in Scheme 9. Reaction of a cyanide salt with an aldehyde and the appropriate substituted amine affords the corresponding aminoacetonitrile which may be purified as the hydrochloride salt of compound 41. Alternatively the same compound 41 can be synthesized by reaction of the amine H$_2$NR$^3$ with an appropriately substituted haloacetonitrile, such as 2-bromopropionitrile, in the presence of a base such as a tertiary amine or an inorganic base such as K$_2$CO$_3$ in an organic solvent and may be isolated as a salt of an inorganic acid by treatment with that acid. Amine salt of compound 41 was treated with an oxalyl halide, R$^1$COCOR$^1$, such as oxalyl chloride or bromide to afford the dihalo compound 42, as described in Vekemans, J.; Pollers-Wieers, C.; Hoornaert, G. *J. Heterocyclic Chem.* 20, 919, (1982). Compounds of compound 42 can be coupled with a secondary amine of compound 22 thermally, in the presence of a strong base such as NaH, KN(SiMe$_3$)$_2$, LiN(SiMe$_3$)$_2$ or NaN(SiMe$_3$)$_2$ in an aprotic organic solvent, or under acid catalysis to give compounds of Formula (I).

Scheme 9

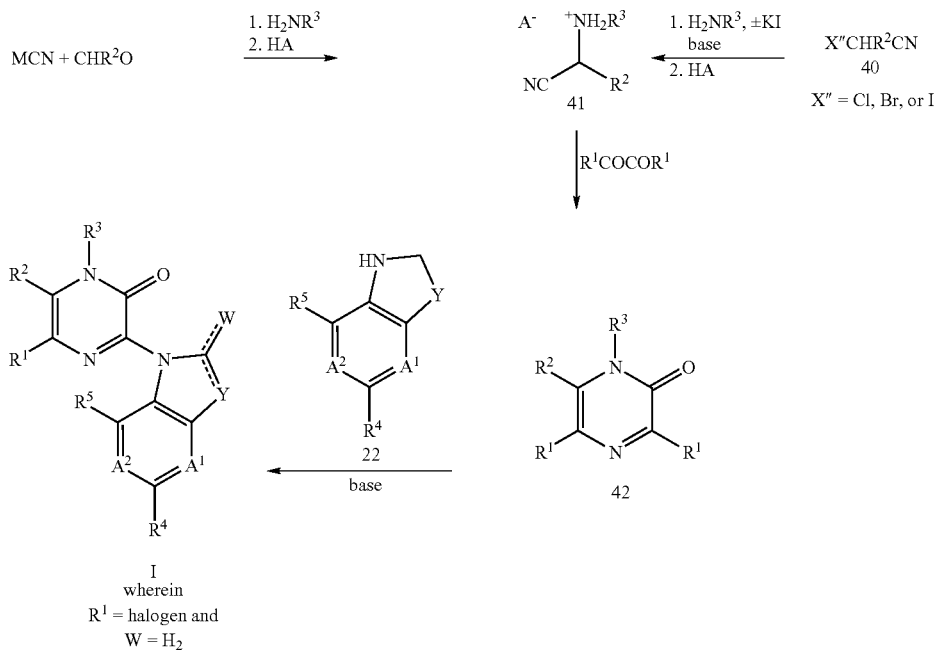

The compounds of Formula (I-a) and (I) where $R^1$, $R^2$ or $R^3$ is a functional group not compatible with the procedures of Schemes 4–9 may be prepared from precursors where the interfering functionality of $R^1$, $R^2$ or $R^3$ is protected using methods known to one skilled in the art (see T. W. Green and P. G. M. Wuts, *Protecting Groups in Organic Synthesis*, Wiley, New York, 1991); or from precursors bearing $R^1$, $R^2$ or $R^3$ groups amenable to later conversion into the desired functionality using standard methods (see J. March, *Advanced Organic Chemistry*, Wiley, New York, 1992).

Alternatively, compounds of Formula (I) wherein $R^1$=halogen can be prepared as shown in Scheme 10. Reaction of an aminoacetonitrile salt 20, described in Scheme 4, with an oxalyl halide ester 30, gives the corresponding amide 31, which can be converted to the corresponding imidate salt 32 in the presence of an acid such as HCl and an alcohol where R' is a protecting group which can be removed later in the synthesis using conditions which will not destroy the structural integrity of the molecule. Examples of protecting groups which might be used include, but are not limited to, methyl, allyl, benzyl, p-methoxybenzyl and methoxymethyl. The imidate salt 32 can be cyclized under treatment with a base, such as $K_2CO_3$ or $Et_3N$ to the pyrazinedione of Formula 33. R' can then be removed using conditions appropriate for the choice of the protecting group known to one skilled in the art (see T. W. Greene and P. G. M. Wuts, *Protecting Groups in Organic Synthesis*, Wiley, New York, 1991). Intermediate 43 can be brominated using conditions such as $Br_2$/HOAc or NBS to give compounds of Formula 44. The bromide in compounds of Formula 44 may or may not be displaced. If it is desired to refunctionalize this group, it can be treated with other halides using reagents such as NaF, KF, LiF, NaCl, KCl, LiCl, NaI, KI or LiI. Alternatively, the bromide can be displaced with other nucleophiles such as —$OR^a$ where $R^a$=$C_1$–$C_3$ alkyl, —$NR^aR^b$ where $R^a$ and $R^b$ are independently H or $C_1$–$C_3$ alkyl or —$SR^a$ where $R^a$=$C_1$–$C_3$ alkyl. If the bromide is displaced with —$SR^a$, the resulting sulfide may be oxidized to either the sulfoxide or sulfone. In addition the bromide may be displaced with $H_2S$. The resulting thiol may be subsequently oxidized to form a sulfonic acid which may also be converted to the sulfonamide using conditions known to one skilled in the art of synthetic organic chemistry. The bromide may also be converted to a nitrile by treatment with various reagents such as, but not limited to KCN, NaCN and $ZnCN/PdL_4$. The resulting product 45 may be treated with a halogenating reagent, such as but not limited to $POCl_3$, $POBr_3$, $(COCl)_2$, $(COBr)_2$, $SOCl_2$ or $SOBr_2$ to form compounds of Formula 42 as described in Scheme 7. Subsequently, 42 may be coupled with a secondary amine of Formula 22 to give the corresponding adduct of Formula I under conditions described in Scheme 4. $R^1$ of Formula I may subsequently be converted to an alkyl group using conditions described in Schemes 5 or 6 provided that $R^{2a}$ is a group other than bromide or iodide.

Scheme 10

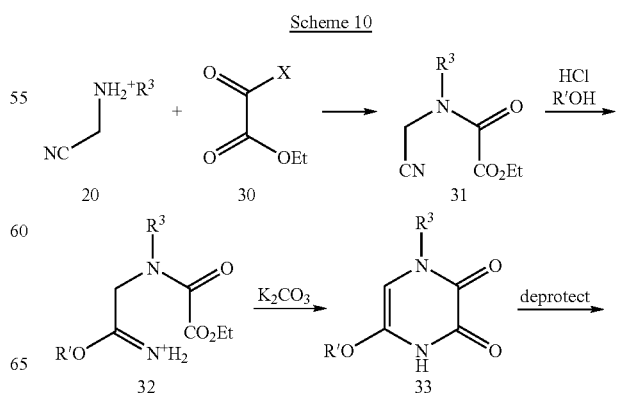

-continued

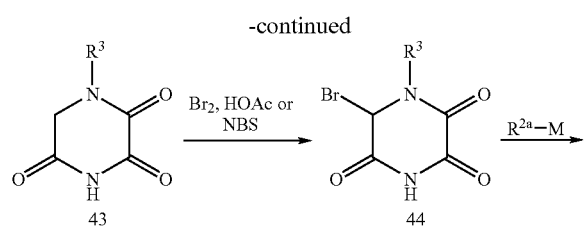

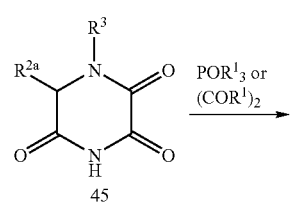

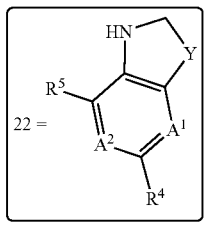

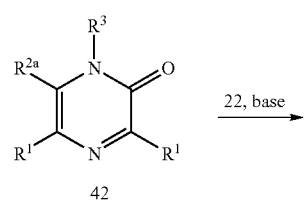

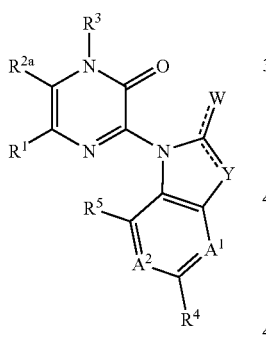

I
wherein
R¹ = halogen or alkyl and
W = H₂

Intermediates wherein compound 22 is indoline or substituted indoline are well known in the art and/or synthesized by methods well known to one skilled in the art. For example, U.S. Pat. No. 6,245,769, issued Jun. 12, 2001, herein incorporated by reference, discloses examples of substituted indolines and the syntheses thereof.

Intermediates of compound 22 where Y=—OCH₂— can be prepared as illustrated in Scheme 11. An appropriate starting material such as 4-fluoro-2-nitrophenol can be treated with nucleophiles such as, but not limited to an alkali metal alkoxide such as sodium, potassium or lithium methoxide, sodium or potassium cyanide, alkylsufides, halide salts or alkali metal hydroxides in an organic solvent to give product 47. Reduction of the nitro group of 47 can be achieved with reagents such as, but not limited to H₂/Pd/C, SnCl₂.2H₂O or iron catalysts (preferably H₂/Pd/C) in an organic solvent appropriate for the chosen reaction conditions to give aminophenol 48. The resultant product 48 can be treated with a base such as, but not limited to alkali metal carbonates, alkali metal alkoxides or alkali metal hexamethyldisilazide bases (preferably K₂CO₃) and dibromoethane in an organic solvent such as acetone, acetonitrile, tetrahydrofuran, dioxane or DMF to form compounds of formula 49. These products can be treated with halogenating reagents such as, but not limited to pyridinium tribromide, N-bromosuccinimide, bromine, N-chlorosuccinimide, iodine, or iodine monobromide to give the corresponding halogenated products of formula 22. If desired, the halogen group at R⁵ may be refunctionalized by treatment with reagents such as but not limited to ZnCN/PdL₄ to form an aryl cyanide or ROH and Pd(OAc)₂/L or Ni(COD)₂/L to form an aryl ether. R⁵ may also be converted to an alkyl group by protection of the aniline nitrogen with a Boc group, treatment of the Boc protected product with n-BuLi or similar bases followed by addition of an alkylating agent such as methyl iodide and removal of the Boc group to form compounds of formula 22.

Scheme II

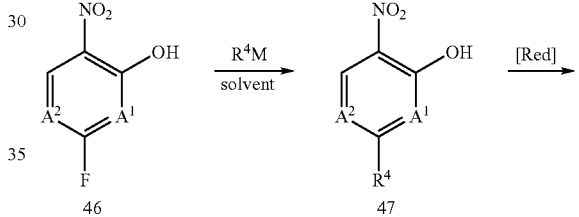

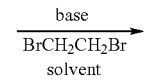

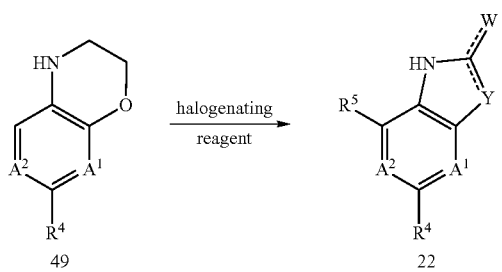

wherein
W = H₂, Y = —OCH₂—

Various analogs synthesized using Schemes 1–11 are listed in the Tables below; as well as compounds envisioned by the invention.

TABLE 1

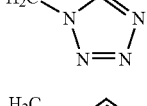

| Ex.# | X | R³ | R² | R⁴ | R⁵ | Mp °C. |
|---|---|---|---|---|---|---|
| 1 | N | CHEt₂ | H | Cl | Cl | 116–117 |
| 2 | N | CHEt₂ | Cl | Cl | Cl | 132–134 |
| 3 | N | CHEt₂ | Br | Cl | Cl | 136–138 |
| 4 | N | CHEt₂ | I | Cl | Cl | |
| 5 | N | CHEt₂ | CN | Cl | Cl | 163–165 |
| 6 | N | CHEt₂ | CHO | Cl | Cl | 182–184 |
| 7 | N | CHEt₂ | CH₂OH | Cl | Cl | 150–152 |
| 8 | N | CHEt₂ | CH₂OMe | Cl | Cl | |
| 9 | N | CHEt₂ | COMe | Cl | Cl | |
| 10 | N | CHEt₂ | CHNOMe | Cl | Cl | |
| 11 | N | CHEt₂ | OMe | Cl | Cl | |
| 12 | N | CHEt₂ | SMe | Cl | Cl | |
| 13 | N | CHEt₂ | SOMe | Cl | Cl | |
| 14 | N | CHEt₂ | SO₂Me | Cl | Cl | |
| 15 | N | CHEt₂ | CO₂Me | Cl | Cl | |
| 16 | N | CHEt₂ | CONHMe | Cl | Cl | |
| 17 | N | CHEt₂ | CONMe₂ | Cl | Cl | |
| 17a | N | CHEt₂ | NO₂ | Cl | Cl | |
| 17b | N | CHEt₂ | 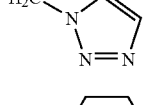 | Cl | Cl | |
| 17c | N | CHEt₂ | 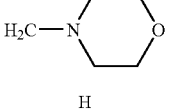 | Cl | Cl | |
| 17d | N | CHEt₂ | H₂C-N(morpholine) | Cl | Cl | |
| 18 | N | CHEt(CH₂OMe) | H | Cl | Cl | |
| 19 | N | CHEt(CH₂OMe) | Cl | Cl | Cl | |
| 20 | N | CHEt(CH₂OMe) | Br | Cl | Cl | |
| 21 | N | CHEt(CH₂OMe) | I | Cl | Cl | |
| 22 | N | CHEt(CH₂OMe) | CN | Cl | Cl | |
| 23 | N | CHEt(CH₂OMe) | CHO | Cl | Cl | |
| 24 | N | CHEt(CH₂OMe) | CH₂OH | Cl | Cl | |
| 25 | N | CHEt(CH₂OMe) | CH₂OMe | Cl | Cl | |
| 26 | N | CHEt(CH₂OMe) | OMe | Cl | Cl | |
| 27 | N | CHEt(CH₂OMe) | COMe | Cl | Cl | |
| 28 | N | CHEt(CH₂OMe) | CHNOMe | Cl | Cl | |
| 29 | N | CHEt(CH₂OMe) | SMe | Cl | Cl | |
| 30 | N | CHEt(CH₂OMe) | SOMe | Cl | Cl | |
| 31 | N | CHEt(CH₂OMe) | SO₂Me | Cl | Cl | |
| 32 | N | CHEt(CH₂OMe) | CO₂Me | Cl | Cl | |
| 33 | N | CHEt(CH₂OMe) | CONHMe | Cl | Cl | |
| 34 | N | CHEt(CH₂OMe) | CONMe₂ | Cl | Cl | |
| 35 | N | CHEt(C₂H₄OMe) | H | Cl | Cl | |
| 36 | N | CHEt(C₂H₄Ome) | COMe | Cl | Cl | |
| 37 | N | CHEt(C₂H₄Ome) | CHNOMe | Cl | Cl | |
| 38 | N | CHEt(C₂H₄Ome) | Cl | Cl | Cl | |
| 39 | N | CHEt(C₂H₄Ome) | Br | Cl | Cl | |
| 40 | N | CHEt(C₂H₄Ome) | I | Cl | Cl | |
| 41 | N | CHEt(C₂H₄Ome) | CN | Cl | Cl | |
| 42 | N | CHEt(C₂H₄Ome) | CHO | Cl | Cl | |
| 43 | N | CHEt(C₂H₄Ome) | CH₂OH | Cl | Cl | |
| 44 | N | CHEt(C₂H₄OMe) | CH₂OMe | Cl | Cl | |
| 45 | N | CHEt(C₂H₄OMe) | C(Me)NOMe | Cl | Cl | |
| 46 | N | CHEt(C₂H₄OMe) | OMe | Cl | Cl | |
| 47 | N | CHEt(C₂H₄OMe) | SMe | Cl | Cl | |
| 48 | N | CHEt(C₂H₄OMe) | SOMe | Cl | Cl | |
| 49 | N | CHEt(C₂H₄OMe) | SO₂Me | Cl | Cl | |
| 50 | N | CHEt(C₂H₄OMe) | CO₂Me | Cl | Cl | |
| 51 | N | CHEt(C₂H₄OMe) | CONHMe | Cl | Cl | |
| 52 | N | CHEt(C₂H₄OMe) | CONMe₂ | Cl | Cl | |
| 53 | N | CHEt₂ | H | OMe | Cl | |
| 54 | N | CHEt₂ | COMe | OMe | Cl | |
| 55 | N | CHEt₂ | CHNOMe | OMe | Cl | |
| 56 | N | CHEt₂ | Cl | OMe | Cl | |
| 57 | N | CHEt₂ | Br | OMe | Cl | |
| 58 | N | CHEt₂ | I | OMe | Cl | |
| 59 | N | CHEt₂ | CN | OMe | Cl | 189–190 |
| 60 | N | CHEt₂ | CHO | OMe | Cl | 178–179 |
| 61 | N | CHEt₂ | CH₂OH | OMe | Cl | |
| 62 | N | CHEt₂ | CH₂OMe | OMe | Cl | |
| 63 | N | CHEt₂ | OMe | OMe | Cl | |
| 64 | N | CHEt₂ | SMe | OMe | Cl | |
| 65 | N | CHEt₂ | SOMe | OMe | Cl | |
| 66 | N | CHEt₂ | SO₂Me | OMe | Cl | |
| 67 | N | CHEt₂ | CO₂Me | OMe | Cl | |
| 68 | N | CHEt₂ | CONHMe | OMe | Cl | |
| 69 | N | CHEt₂ | CONMe₂ | OMe | Cl | |
| 70 | N | CHEt(CH₂OMe) | H | OMe | Cl | |
| 71 | N | CHEt(CH₂OMe) | COMe | OMe | Cl | |
| 72 | N | CHEt(CH₂OMe) | Cl | OMe | Cl | |
| 73 | N | CHEt(CH₂OMe) | Br | OMe | Cl | |
| 74 | N | CHEt(CH₂OMe) | I | OMe | Cl | 150–152 |
| 75 | N | CHEt(CH₂OMe) | CN | OMe | Cl | 182–183 |
| 76 | N | CHEt(CH₂OMe) | CHO | OMe | Cl | 150–153 |
| 77 | N | CHEt(CH₂OMe) | CH₂OH | OMe | Cl | 148–150 |
| 78 | N | CHEt(CH₂OMe) | CH₂OMe | OMe | Cl | |
| 79 | N | CHEt(CH₂OMe) | OMe | OMe | Cl | |
| 80 | N | CHEt(CH₂OMe) | SMe | OMe | Cl | |
| 81 | N | CHEt(CH₂OMe) | SOMe | OMe | Cl | |
| 82 | N | CHEt(CH₂OMe) | SO₂Me | OMe | Cl | |
| 83 | N | CHEt(CH₂OMe) | CO₂Me | OMe | Cl | |
| 84 | N | CHEt(CH₂OMe) | CONHMe | OMe | Cl | |
| 85 | N | CHEt(CH₂OMe) | CONMe₂ | OMe | Cl | |
| 86 | N | CHEt(C₂H₄OMe) | H | OMe | Cl | |
| 87 | N | CHEt(C₂H₄OMe) | COMe | OMe | Cl | |
| 88 | N | CHEt(C₂H₄OMe) | CHNOMe | OMe | Cl | |
| 89 | N | CHEt(C₂H₄OMe) | Cl | OMe | Cl | |

TABLE 1-continued

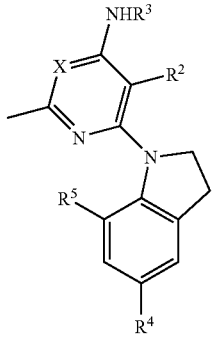

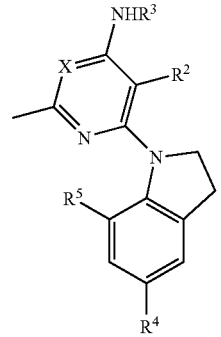

| Ex.# | X | R$^3$ | R$^2$ | R$^4$ | R$^5$ | Mp °C. | Ex.# | X | R$^3$ | R$^2$ | R$^4$ | R$^5$ | Mp °C. |
|---|---|---|---|---|---|---|---|---|---|---|---|---|---|
| 90 | N | CHEt(C$_2$H$_4$OMe) | Br | OMe | Cl |  | 139 | N | CHEt(C$_2$H$_4$OMe) | CHNOMe | Me | Cl |  |
| 91 | N | CHEt(C$_2$H$_4$OMe) | I | OMe | Cl | 127–129 | 140 | N | CHEt(C$_2$H$_4$OMe) | Cl | Me | Cl |  |
| 92 | N | CHEt(C$_2$H$_4$OMe) | CN | OMe | Cl | 137–139 | 141 | N | CHEt(C$_2$H$_4$OMe) | Br | Me | Cl |  |
| 93 | N | CHEt(C$_2$H$_4$OMe) | CHO | OMe | Cl | 125–128 | 142 | N | CHEt(C$_2$H$_4$OMe) | I | Me | Cl | 99–100 |
| 94 | N | CHEt(C$_2$H$_4$OMe) | CH$_2$OH | OMe | Cl | 110–113 | 143 | N | CHEt(C$_2$H$_4$OMe) | CN | Me | Cl | A-morphous |
| 95 | N | CHEt(C$_2$H$_4$OMe) | CH$_2$OMe | OMe | Cl |  | 144 | N | CHEt(C$_2$H$_4$OMe) | CHO | Me | Cl | A-morphous |
| 96 | N | CHEt(C$_2$H$_4$OMe) | OMe | OMe | Cl |  |  |  |  |  |  |  |  |
| 97 | N | CHEt(C$_2$H$_4$OMe) | SMe | OMe | Cl |  | 145 | N | CHEt(C$_2$H$_4$OMe) | CH$_2$OH | Me | Cl |  |
| 98 | N | CHEt(C$_2$H$_4$OMe) | SOMe | OMe | Cl |  | 146 | N | CHEt(C$_2$H$_4$OMe) | C(Me)NOMe | Me | Cl |  |
| 99 | N | CHEt(C$_2$H$_4$OMe) | SO$_2$Me | OMe | Cl |  | 147 | N | CHEt(C$_2$H$_4$OMe) | CH$_2$OMe | Me | Cl |  |
| 100 | N | CHEt(C$_2$H$_4$OMe) | CO$_2$Me | OMe | Cl |  | 148 | N | CHEt(C$_2$H$_4$OMe) | OMe | Me | Cl |  |
| 101 | N | CHEt(C$_2$H$_4$OMe) | CONHMe | OMe | Cl |  | 149 | N | CHEt(C$_2$H$_4$OMe) | SMe | Me | Cl |  |
| 102 | N | CHEt(C$_2$H$_4$OMe) | CONMe$_2$ | OMe | Cl |  | 150 | N | CHEt(C$_2$H$_4$OMe) | SOMe | Me | Cl |  |
| 103 | N | CHEt$_2$ | H | Me | Cl |  | 151 | N | CHEt(C$_2$H$_4$OMe) | SO$_2$Me | Me | Cl |  |
| 104 | N | CHEt$_2$ | COMe | Me | Cl |  | 152 | N | CHEt(C$_2$H$_4$OMe) | CO$_2$Me | Me | Cl |  |
| 105 | N | CHEt$_2$ | CHNOMe | Me | Cl |  | 153 | N | CHEt(C$_2$H$_4$OMe) | CONHMe | Me | Cl |  |
| 106 | N | CHEt$_2$ | Cl | Me | Cl |  | 154 | N | CHEt(C$_2$H$_4$OMe) | CONMe$_2$ | Me | Cl |  |
| 107 | N | CHEt$_2$ | Br | Me | Cl |  | 155 | CH | CHEt$_2$ | H | Cl | Cl |  |
| 108 | N | CHEt$_2$ | I | Me | Cl | 115–116 | 156 | CH | CHEt$_2$ | COMe | Cl | Cl |  |
| 109 | N | CHEt$_2$ | CN | Me | Cl | 155–157 | 157 | CH | CHEt$_2$ | CHNOMe | Cl | Cl |  |
| 110 | N | CHEt$_2$ | CHO | Me | Cl | 155–156 | 158 | CH | CHEt$_2$ | Cl | Cl | Cl |  |
|  |  |  |  |  |  |  | 159 | CH | CHEt$_2$ | Br | Cl | Cl |  |
| 111 | N | CHEt$_2$ | CH$_2$OH | Me | Cl |  | 160 | CH | CHEt$_2$ | I | Cl | Cl |  |
|  |  |  |  |  |  |  | 161 | CH | CHEt$_2$ | CN | Cl | Cl |  |
| 112 | N | CHEt$_2$ | CH$_2$OMe | Me | Cl |  | 162 | CH | CHEt$_2$ | CHO | Cl | Cl |  |
| 113 | N | CHEt$_2$ | OMe | Me | Cl |  | 163 | CH | CHEt$_2$ | CH$_2$OH | Cl | Cl |  |
| 114 | N | CHEt$_2$ | SMe | Me | Cl |  | 164 | CH | CHEt$_2$ | CH$_2$OMe | Cl | Cl |  |
| 115 | N | CHEt$_2$ | SOMe | Me | Cl |  | 165 | CH | CHEt$_2$ | OMe | Cl | Cl |  |
| 116 | N | CHEt$_2$ | SO$_2$Me | Me | Cl |  | 166 | CH | CHEt$_2$ | SNe | Cl | Cl |  |
| 117 | N | CHEt$_2$ | CO$_2$Me | Me | Cl |  | 167 | CH | CHEt$_2$ | SOMe | Cl | Cl |  |
| 118 | N | CHEt$_2$ | CONHMe | Me | Cl |  | 168 | CH | CHEt$_2$ | SO$_2$Me | Cl | Cl |  |
| 119 | N | CHEt$_2$ | CONMe$_2$ | Me | Cl |  | 169 | CH | CHEt$_2$ | CO$_2$Me | Cl | Cl |  |
| 120 | N | CHEt(CH$_2$OMe) | H | Me | Cl |  | 170 | CH | CHEt$_2$ | CONHMe | Cl | Cl |  |
| 121 | N | CHEt(CH$_2$OMe) | COMe | Me | Cl |  | 171 | CH | CHEt$_2$ | CONMe$_2$ | Cl | Cl |  |
| 122 | N | CHEt(CH$_2$OMe) | CHNOMe | Me | Cl |  | 172 | CH | CHEt(CH$_2$OMe) | H | Cl | Cl |  |
| 123 | N | CHEt(CH$_2$OMe) | Cl | Me | Cl |  | 173 | CH | CHEt(CH$_2$OMe) | COMe | Cl | Cl |  |
| 124 | N | CHEt(CH$_2$OMe) | Br | Me | Cl |  | 174 | CH | CHEt(CH$_2$OMe) | CHNOMe | Cl | Cl |  |
| 125 | N | CHEt(CH$_2$OMe) | I | Me | Cl | 135–138 | 175 | CH | CHEt(CH$_2$OMe) | Cl | Cl | Cl |  |
|  |  |  |  |  |  |  | 176 | CH | CHEt(CH$_2$OMe) | Br | Cl | Cl |  |
| 126 | N | CHEt(CH$_2$OMe) | CN | Me | Cl | 135–138 | 177 | CH | CHEt(CH$_2$OMe) | I | Cl | Cl |  |
|  |  |  |  |  |  |  | 178 | CH | CHEt(CH$_2$OMe) | CN | Cl | Cl |  |
| 127 | N | CHEt(CH$_2$OMe) | CHO | Me | Cl | 134–136 | 179 | CH | CHEt(CH$_2$OMe) | CHO | Cl | Cl |  |
| 128 | N | CHEt(CH$_2$OMe) | CH$_2$OH | Me | Cl |  | 180 | CH | CHEt(CH$_2$OMe) | CH$_2$OH | Cl | Cl |  |
| 129 | N | CHEt(CH$_2$OMe) | CH$_2$OMe | Me | Cl |  | 181 | CH | CHEt(CH$_2$OMe) | CH$_2$OMe | Cl | Cl |  |
| 130 | N | CHEt(CH$_2$OMe) | OMe | Me | Cl |  | 182 | CH | CHEt(CH$_2$OMe) | OMe | Cl | Cl |  |
| 131 | N | CHEt(CH$_2$OMe) | SMe | Me | Cl |  | 183 | CH | CHEt(CH$_2$OMe) | SMe | Cl | Cl |  |
| 132 | N | CHEt(CH$_2$OMe) | SOMe | Me | Cl |  | 184 | CH | CHEt(CH$_2$OMe) | SOMe | Cl | Cl |  |
| 133 | N | CHEt(CH$_2$OMe) | SO$_2$Me | Me | Cl |  | 185 | CH | CHEt(CH$_2$OMe) | SO$_2$Me | Cl | Cl |  |
| 134 | N | CHEt(CH$_2$OMe) | CO$_2$Me | Me | Cl |  | 186 | CH | CHEt(CH$_2$OMe) | CO$_2$Me | Cl | Cl |  |
| 135 | N | CHEt(CH$_2$OMe) | CONHMe | Me | Cl |  | 187 | CH | CHEt(CH$_2$OMe) | CONHMe | Cl | Cl |  |
| 136 | N | CHEt(CH$_2$OMe) | CONMe$_2$ | Me | Cl |  | 188 | CH | CHEt(CH$_2$OMe) | CONMe$_2$ | Cl | Cl |  |
| 137 | N | CHEt(C$_2$H$_4$OMe) | H | Me | Cl |  | 189 | CH | CHEt(C$_2$H$_4$OMe) | H | Cl | Cl |  |
|  |  |  |  |  |  |  | 190 | CH | CHEt(C$_2$H$_4$OMe) | COMe | Cl | Cl |  |
| 138 | N | CHEt(C$_2$H$_4$OMe) | COMe | Me | Cl |  | 191 | CH | CHEt(C$_2$H$_4$OMe) | CHNOMe | Cl | Cl |  |
|  |  |  |  |  |  |  | 192 | CH | CHEt(C$_2$H$_4$OMe) | Cl | Cl | Cl |  |

TABLE 1-continued

| Ex.# | X | R³ | R² | R⁴ | R⁵ | Mp °C. |
|---|---|---|---|---|---|---|
| 193 | CH | CHEt(C₂H₄OMe) | Br | Cl | Cl | |
| 194 | CH | CHEt(C₂H₄OMe) | I | Cl | Cl | |
| 195 | CH | CHEt(C₂H₄OMe) | CN | Cl | Cl | |
| 196 | CH | CHEt(C₂H₄OMe) | CHO | Cl | Cl | |
| 197 | CH | CHEt(C₂H₄OMe) | CH₂OH | Cl | Cl | |
| 198 | CH | CHEt(C₂H₄OMe) | C(Me)NOMe | Cl | Cl | |
| 199 | CH | CHEt(C₂H₄OMe) | CH₂OMe | Cl | Cl | |
| 200 | CH | CHEt(C₂H₄OMe) | OMe | Cl | Cl | |
| 201 | CH | CHEt(C₂H₄OMe) | SMe | Cl | Cl | |
| 202 | CH | CHEt(C₂H₄OMe) | SOMe | Cl | Cl | |
| 203 | CH | CHEt(C₂H₄OMe) | SO₂Me | Cl | Cl | |
| 204 | CH | CHEt(C₂H₄OMe) | CO₂Me | Cl | Cl | |
| 205 | CH | CHEt(C₂H₄OMe) | CONHMe | Cl | Cl | |
| 206 | CH | CHEt(C₂H₄OMe) | CONMe₂ | Cl | Cl | |
| 207 | CH | CHEt(CH₂OMe) | COMe | OMe | Cl | |
| 208 | CH | CHEt(CH₂OMe) | CHNOMe | OMe | Cl | |
| 209 | CH | CHEt(CH₂OMe) | Cl | OMe | Cl | |
| 210 | CH | CHEt(CH₂OMe) | Br | OMe | Cl | |
| 211 | CH | CHEt(CH₂OMe) | I | OMe | Cl | |
| 212 | CH | CHEt(CH₂OMe) | CN | OMe | Cl | |
| 213 | CH | CHEt(CH₂OMe) | CHO | OMe | Cl | |
| 214 | CH | CHEt(CH₂OMe) | CH₂OH | OMe | Cl | |
| 215 | CH | CHEt(CH₂OMe) | CH₂OMe | OMe | Cl | |
| 216 | CH | CHEt(CH₂OMe) | OMe | OMe | Cl | |
| 217 | CH | CHEt(CH₂OMe) | SMe | OMe | Cl | |
| 218 | CH | CHEt(CH₂OMe) | SOMe | OMe | Cl | |
| 219 | CH | CHEt(CH₂OMe) | SO₂Me | OMe | Cl | |
| 220 | CH | CHEt(CH₂OMe) | CO₂Me | OMe | Cl | |
| 221 | CH | CHEt(CH₂OMe) | CONHMe | OMe | Cl | |
| 222 | CH | CHEt(CH₂OMe) | CONMe₂ | OMe | Cl | |
| 223 | CH | CHEt(C₂H₄OMe) | H | OMe | Cl | |
| 224 | CH | CHEt(C₂H₄OMe) | COMe | OMe | Cl | |
| 225 | CH | CHEt(C₂H₄OMe) | CHNOMe | OMe | Cl | |
| 226 | CH | CHEt(C₂H₄OMe) | Cl | OMe | Cl | |
| 227 | CH | CHEt(C₂H₄OMe) | Br | OMe | Cl | |
| 228 | CH | CHEt(C₂H₄OMe) | I | OMe | Cl | |
| 229 | CH | CHEt(C₂H₄OMe) | CN | OMe | Cl | |
| 230 | CH | CHEt(C₂H₄OMe) | CHO | OMe | Cl | |
| 231 | CH | CHEt(C₂H₄OMe) | CH₂OH | OMe | Cl | |
| 232 | CH | CHEt(C₂H₄OMe) | CH₂OMe | OMe | Cl | |
| 233 | CH | CHEt(C₂H₄OMe) | OMe | OMe | Cl | |
| 234 | CH | CHEt(C₂H₄OMe) | SMe | OMe | Cl | |
| 235 | CH | CHEt(C₂H₄OMe) | SOMe | OMe | Cl | |
| 236 | CH | CHEt(C₂H₄OMe) | SO₂Me | OMe | Cl | |
| 237 | CH | CHEt(C₂H₄OMe) | CO₂Me | OMe | Cl | |
| 238 | CH | CHEt(C₂H₄OMe) | CONHMe | OMe | Cl | |
| 239 | CH | CHEt(C₂H₄OMe) | CONMe₂ | OMe | Cl | |
| 240 | CH | CHEt₂ | H | OMe | Cl | |
| 241 | CH | CHEt₂ | COMe | OMe | Cl | |
| 242 | CH | CHEt₂ | CHNOMe | OMe | Cl | |
| 243 | CH | CHEt₂ | Cl | OMe | Cl | |
| 244 | CH | CHEt₂ | Br | OMe | Cl | |
| 245 | CH | CHEt₂ | I | OMe | Cl | |
| 246 | CH | CHEt₂ | CN | OMe | Cl | |
| 247 | CH | CHEt₂ | CHO | OMe | Cl | |
| 248 | CH | CHEt₂ | CH₂OH | OMe | Cl | |
| 249 | CH | CHEt₂ | CH₂OMe | OMe | Cl | |
| 250 | CH | CHEt₂ | OMe | OMe | Cl | |
| 251 | CH | CHEt₂ | SMe | OMe | Cl | |
| 252 | CH | CHEt₂ | SOMe | OMe | Cl | |
| 253 | CH | CHEt₂ | SO₂Me | OMe | Cl | |
| 254 | CH | CHEt₂ | CO₂Me | OMe | Cl | |
| 255 | CH | CHEt₂ | CONHMe | OMe | Cl | |
| 256 | CH | CHEt₂ | CONMe₂ | OMe | Cl | |
| 256a | CH | CHEt₂ | NO₂ | OMe | Cl | |
| 256b | CH | CHEt₂ | NCO₂CH₂CH(CH₃)₂ | OMe | Cl | |
| 256c | CH | CHEt₂ | NO₂CH₃ | OMe | Cl | |
| 257 | CH | CHEt₂ | H | Me | Cl | |
| 258 | CH | CHEt₂ | COMe | Me | Cl | |
| 259 | CH | CHEt₂ | CHNOMe | Me | Cl | |
| 260 | CH | CHEt₂ | Cl | Me | Cl | |
| 261 | CH | CHEt₂ | Br | Me | Cl | |
| 262 | CH | CHEt₂ | I | Me | Cl | |
| 263 | CH | CHEt₂ | CN | Me | Cl | |
| 264 | CH | CHEt₂ | CHO | Me | Cl | |
| 265 | CH | CHEt₂ | CH₂OH | Me | Cl | |
| 266 | CH | CHEt₂ | CH₂OMe | Me | Cl | |
| 267 | CH | CHEt₂ | OMe | Me | Cl | |
| 268 | CH | CHEt₂ | SMe | Me | Cl | |
| 269 | CH | CHEt₂ | SOMe | Me | Cl | |
| 270 | CH | CHEt₂ | SO₂Me | Me | Cl | |
| 271 | CH | CHEt₂ | CO₂Me | Me | Cl | |
| 272 | CH | CHEt₂ | CONHMe | Me | Cl | |
| 273 | CH | CHEt₂ | CONMe₂ | Me | Cl | |
| 274 | CH | CHEt(CH₂OMe) | H | Me | Cl | |
| 275 | CH | CHEt(CH₂OMe) | COMe | Me | Cl | |
| 276 | CH | CHEt(CH₂OMe) | CHNOMe | Me | Cl | |
| 277 | CH | CHEt(CH₂OMe) | Cl | Me | Cl | |
| 278 | CH | CHEt(CH₂OMe) | Br | Me | Cl | |
| 279 | CH | CHEt(CH₂OMe) | I | Me | Cl | |
| 280 | CH | CHEt(CH₂OMe) | CN | Me | Cl | |
| 281 | CH | CHEt(CH₂OMe) | CHO | Me | Cl | |
| 282 | CH | CHEt(CH₂OMe) | CH₂OH | Me | Cl | |
| 283 | CH | CHEt(CH₂OMe) | CH₂OMe | Me | Cl | |
| 284 | CH | CHEt(CH₂OMe) | OMe | Me | Cl | |
| 285 | CH | CHEt(CH₂OMe) | SMe | Me | Cl | |
| 286 | CH | CHEt(CH₂OMe) | SOMe | Me | Cl | |
| 287 | CH | CHEt(CH₂OMe) | SO₂Me | Me | Cl | |
| 288 | CH | CHEt(CH₂OMe) | CO₂Me | Me | Cl | |
| 289 | CH | CHEt(CH₂OMe) | CONHMe | Me | Cl | |
| 290 | CH | CHEt(CH₂OMe) | CONMe₂ | Me | Cl | |
| 291 | CH | CHEt(C₂H₄OMe) | H | Me | Cl | |
| 292 | CH | CHEt(C₂H₄OMe) | COMe | Me | Cl | |
| 293 | CH | CHEt(C₂H₄OMe) | CHNOMe | Me | Cl | |
| 294 | CH | CHEt(C₂H₄OMe) | Cl | Me | Cl | |
| 295 | CH | CHEt(C₂H₄OMe) | Br | Me | Cl | |
| 296 | CH | CHEt(C₂H₄OMe) | I | Me | Cl | |
| 297 | CH | CHEt(C₂H₄OMe) | CN | Me | Cl | |
| 298 | CH | CHEt(C₂H₄OMe) | CHO | Me | Cl | |
| 299 | CH | CHEt(C₂H₄OMe) | CH₂OH | Me | Cl | |
| 300 | CH | CHEt(C₂H₄OMe) | C(Me)NOMe | Me | Cl | |
| 301 | CH | CHEt(C₂H₄OMe) | CH₂OMe | Me | Cl | |
| 302 | CH | CHEt(C₂H₄OMe) | OMe | Me | Cl | |
| 303 | CH | CHEt(C₂H₄OMe) | SMe | Me | Cl | |
| 304 | CH | CHEt(C₂H₄OMe) | SOMe | Me | Cl | |
| 305 | CH | CHEt(C₂H₄OMe) | SO₂Me | Me | Cl | |
| 306 | CH | CHEt(C₂H₄OMe) | CO₂Me | Me | Cl | |
| 307 | CH | CHEt(C₂H₄OMe) | CONHMe | Me | Cl | |

TABLE 1-continued

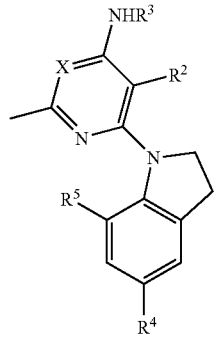

| Ex.# | X | R³ | R² | R⁴ | R⁵ | Mp °C. |
|---|---|---|---|---|---|---|
| 308 | CH | CHEt(C₂H₄OMe) | CONMe₂ | Me | Cl | |
| 309 | N | CH(nPr)Me | H | OMe | Cl | |
| 310 | N | CH(Et)Me | H | OMe | Cl | |
| 311 | N | CH(cBu)Me | H | OMe | Cl | |

TABLE 2

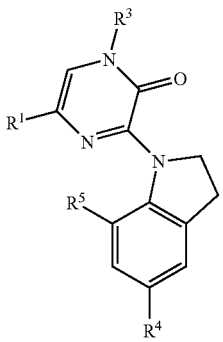

| Ex.# | R¹ | R³ | R⁴ | R⁵ | Mass Spec (M + H) Melting point °C. |
|---|---|---|---|---|---|
| 401 | Cl | CHEt₂ | Cl | Cl | 386 168–170° C. |
| 402 | Cl | CH(cPr)Et | Cl | Cl | 398 |
| 403 | Cl | CH(cPr)Me | Cl | Cl | |
| 404 | Cl | CH(Et)CH₂OMe | Cl | Cl | 402 |
| 405 | Cl | CH(cPr)CH₂OMe | Cl | Cl | |
| 406 | Cl | CH(cBu)CH₂OMe | Cl | Cl | |
| 407 | Cl | CH(nPr)CH₂OMe | Cl | Cl | |
| 408 | Cl | CH(cPr)C₂H₄OMe | Cl | Cl | |
| 409 | Cl | CH(cBu)C₂H₄OMe | Cl | Cl | |
| 410 | Cl | CH(Et)C₂H₄OMe | Cl | Cl | 416 95–97° C. |
| 411 | Cl | CHEt₂ | OMe | Cl | |
| 412 | Cl | CH(cPr)Et | OMe | Cl | |
| 413 | Cl | CH(Et)CH₂OMe | OMe | Cl | 398 |
| 414 | Cl | CH(cPr)Me | OMe | Cl | |
| 415 | Cl | CH(cPr)CH₂OMe | OMe | Cl | |
| 416 | Cl | CH(cBu)CH₂OMe | OMe | Cl | |
| 417 | Cl | CH(nPr)CH₂OMe | OMe | Cl | |
| 418 | Cl | CH(cPr)C₂H₄OMe | OMe | Cl | |
| 419 | Cl | CH(cBu)C₂H₄OMe | OMe | Cl | |
| 420 | Cl | CH(Et)C₂H₄OMe | OMe | Cl | 412 |
| 421 | Cl | CHEt₂ | Me | Cl | |
| 422 | Cl | CH(cPr)Et | Me | Cl | |
| 423 | Cl | CH(Et)CH₂OMe | Me | Cl | |
| 424 | Cl | CH(cPr)Me | Me | Cl | |
| 425 | Cl | CH(cPr)CH₂OMe | Me | Cl | |
| 426 | Cl | CH(cBu)CH₂OMe | Me | Cl | |
| 427 | Cl | CH(nPr)CH₂OMe | Me | Cl | |
| 428 | Cl | CH(cPr)C₂H₄OMe | Me | Cl | |

TABLE 2-continued

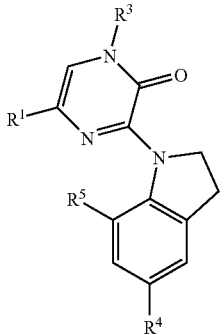

| Ex.# | R¹ | R³ | R⁴ | R⁵ | Mass Spec (M + H) Melting point °C. |
|---|---|---|---|---|---|
| 429 | Cl | CH(cBu)C₂H₄OMe | Me | Cl | |
| 430 | Cl | CH(Et)C₂H₄OMe | Me | Cl | |
| 431 | Cl | CHEt₂ | OMe | Me | 362 164–165° C. |
| 432 | Cl | CH(cPr)Et | OMe | Me | |
| 433 | Cl | CH(Et)CH₂OMe | OMe | Me | 378 |
| 434 | Cl | CH(cPr)Me | OMe | Me | |
| 435 | Cl | CH(cPr)CH₂OMe | OMe | Me | |
| 436 | Cl | CH(cBu)CH₂OMe | OMe | Me | |
| 437 | Cl | CH(nPr)CH₂OMe | OMe | Me | |
| 438 | Cl | CH(cPr)C₂H₄OMe | OMe | Me | |
| 439 | Cl | CH(cBu)C₂H₄OMe | OMe | Me | |
| 440 | Cl | CH(Et)C₂H₄OMe | OMe | Me | 392 |
| 441 | Cl | CHEt₂ | OMe | Br | 426 130–132° C. |
| 442 | Cl | CH(cPr)Et | OMe | Br | |
| 443 | Cl | CH(Et)CH₂OMe | OMe | Br | 442 |
| 444 | Cl | CH(cPr)Me | OMe | Br | |
| 445 | Cl | CH(cPr)CH₂OMe | OMe | Br | |
| 446 | Cl | CH(cBu)CH₂OMe | OMe | Br | |
| 447 | Cl | CH(nPr)CH₂OMe | OMe | Br | |
| 448 | Cl | CH(cPr)C₂H₄OMe | OMe | Br | |
| 449 | Cl | CH(cBu)C₂H₄OMe | OMe | Br | |
| 450 | Cl | CH(Et)C₂H₄OMe | OMe | Br | 454 |
| 451 | Me | CHEt₂ | Cl | Cl | 366 137–139° C. |
| 452 | Me | CH(cPr)Et | Cl | Cl | |
| 453 | Me | CH(Et)CH₂OMe | Cl | Cl | |
| 454 | Me | CH(cPr)Me | Cl | Cl | |
| 455 | Me | CH(cPr)CH₂OMe | Cl | Cl | |
| 456 | Me | CH(cBu)CH₂OMe | Cl | Cl | |
| 457 | Me | CH(nPr)CH₂OMe | Cl | Cl | |
| 458 | Me | CH(cPr)C₂H₄OMe | Cl | Cl | |
| 459 | Me | CH(cBu)C₂H₄OMe | Cl | Cl | |
| 460 | Me | CH(Et)C₂H₄OMe | Cl | Cl | |
| 461 | Me | CHEt₂ | OMe | Cl | |
| 462 | Me | CH(Et)CH₂OMe | OMe | Cl | |
| 463 | Me | CH(cPr)Et | OMe | Cl | |
| 464 | Me | CH(cPr)Me | OMe | Cl | |
| 465 | Me | CH(cPr)CH₂OMe | OMe | Cl | |
| 466 | Me | CH(cBu)CH₂OMe | OMe | Cl | |
| 467 | Me | CH(nPr)CH₂OMe | OMe | Cl | |
| 468 | Me | CH(cPr)C₂H₄OMe | OMe | Cl | |
| 469 | Me | CH(cBu)C₂H₄OMe | OMe | Cl | |
| 470 | Me | CH(Et)C₂H₄OMe | OMe | Cl | |
| 471 | Me | CHEt₂ | Me | Cl | |
| 472 | Me | CH(Et)CH₂OMe | Me | Cl | |
| 473 | Me | CH(cPr)Et | Me | Cl | |
| 474 | Me | CH(cPr)Me | Me | Cl | |
| 475 | Me | CH(cPr)CH₂OMe | Me | Cl | |
| 476 | Me | CH(cBu)CH₂OMe | Me | Cl | |
| 477 | Me | CH(nPr)CH₂OMe | Me | Cl | |
| 478 | Me | CH(cPr)C₂H₄OMe | Me | Cl | |
| 479 | Me | CH(cBu)C₂H₄OMe | Me | Cl | |
| 480 | Me | CH(Et)C₂H₄OMe | Me | Cl | |
| 481 | Me | CHEt₂ | OMe | Me | 342 138–140° C. |
| 482 | Me | CH(cPr)Et | OMe | Me | |
| 483 | Me | CH(Et)CH₂OMe | OMe | Me | |

TABLE 2-continued

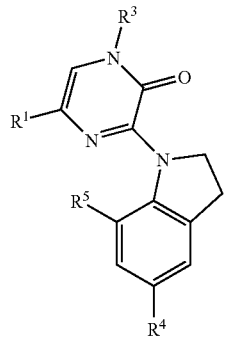

| Ex.# | R¹ | R³ | R⁴ | R⁵ | Mass Spec (M + H) Melting point ° C. |
|---|---|---|---|---|---|
| 484 | Me | CH(cPr)Me | OMe | Me | |
| 485 | Me | CH(cPr)CH₂OMe | OMe | Me | |
| 486 | Me | CH(cBu)CH₂OMe | OMe | Me | |
| 487 | Me | CH(nPr)CH₂OMe | OMe | Me | |
| 488 | Me | CH(cPr)C₂H₄OMe | OMe | Me | |
| 489 | Me | CH(cBu)C₂H₄OMe | OMe | Me | |
| 490 | Me | CH(Et)C₂H₄OMe | OMe | Me | |
| 491 | Me | CHEt₂ | OMe | Br | |
| 492 | Me | CH(cPr)Et | OMe | Br | |
| 493 | Me | CH(Et)CH₂OMe | OMe | Br | |
| 494 | Me | CH(cPr)Me | OMe | Br | |
| 495 | Me | CH(cPr)CH₂OMe | OMe | Br | |
| 496 | Me | CH(cBu)CH₂OMe | OMe | Br | |
| 497 | Me | CH(nPr)CH₂OMe | OMe | Br | |
| 498 | Me | CH(cPr)C₂H₄OMe | OMe | Br | |
| 499 | Me | CH(cBu)C₂H₄OMe | OMe | Br | |
| 500 | Me | CH(Et)C₂H₄OMe | OMe | Br | |
| 501 | Cl | CH(Et)Me | OMe | Cl | 368.0927 |
| 502 | Cl | CH(Et)Me | OMe | Br | 412.0448 |
| 503 | Cl | CH(Et)Me | OMe | Me | 348.1490 |
| 504 | Cl | CH(Et)Me | Cl | Cl | 372.0428 |
| 505 | Br | CH(Et)Me | OMe | Br | 470.0084 |
| 506 | Br | CHEt₂ | OMe | Me | 406.1125 |
| 507 | Br | CHEt₂ | Cl | Cl | 430.0109 |
| 508 | Cl | CH(cPr)Et | OMe | Cl | 394.1099 |
| 509 | Cl | CH(cPr)Et | OMe | Br | 438.0570 |
| 510 | Cl | CH(cPr)Et | OMe | Me | 374.1617 |
| 511 | Cl | CH(cPr)Et | Cl | Cl | 398.0575 |
| 512 | Cl | CH(cPr)Et | Br | Br | 485.9592 |
| 514 | Cl | CH(cPr)Et | OMe | Cl | 394.1088 |
| 515 | Cl | CH(cPr)Et | OMe | Br | 438.0605 |
| 516 | Cl | CH(cPr)Et | OMe | Me | 374.1634 |
| 517 | Cl | CH(cPr)Et | Cl | Cl | 398.0602 |
| 518 | Cl | CH(cPr)Et | Br | Br | 485.9604 |
| 520 | Cl | CH(Me)CH₂OMe | Cl | Cl | 388.0358 |
| 521 | Cl | CH(Me)CH₂OMe | Br | Br | 474.9285 |
| 523 | Cl | CH(Et)CH₂OMe | OMe | Br | 442.0532 |
| 524 | Cl | CH(Et)CH₂OMe | Cl | Cl | 402.0568 |
| 525 | Br | CH(Et)CH₂OMe | OMe | Br | 486.0018 |
| 526 | Br | CH(Et)CH₂OMe | OMe | Me | 422.1097 |
| 527 | Br | CH(Et)CH₂OMe | Cl | Cl | 446.0008 |
| 529 | Cl | CH(Et)CH₂OMe | OMe | Br | 442.0516 |
| 530 | Cl | CH(Et)CH₂OMe | Cl | Cl | 402.0520 |
| 531 | Br | CH(Et)CH₂OMe | Cl | Cl | 446.0050 |
| 532 | Cl | CH(CH(Me)CH₃)₂ | OMe | Me | 390.1958 |
| 533 | Cl | CH₂(CH₂CH₂SMe) | OMe | Br | 428.9899 |
| 534 | Cl | CH₂(CH₂CH₂SMe) | OMe | Me | 365.0967 |
| 535 | Cl | CH₂(CH₂CH₂SMe) | Cl | Cl | 388.9920 |
| 538 | Cl | CH(Et)Me | Br | Cl | 415.9943 |
| 539 | Et | CHEt₂ | Cl | Cl | 380.1280 |
| 540 | Cl | CHEt₂ | Br | Cl | 430.0106 |
| 541 | —CN | CHEt₂ | Cl | Cl | 377.0910 |
| 542 | Cl | (1R)-CH(cPr)Et | Br | Cl | 442.0102 |
| 543 | Cl | (1S)-CH(cPr)Et | Br | Cl | 442.0093 |
| 544 | Cl | CH(Et)CH₂OMe | OMe | Cl | 398.1064 |
| 545 | Cl | CH(Et)CH₂OMe | OMe | Me | 378.1604 |
| 546 | Cl | CH(Et)CH₂OMe | OMe | CN | 388.1298 |
| 547 | Br | (1R)-CH(Et)CH₂OMe | Br | Br | 489.9534 |
| 548 | Cl | (1S)-CH(Et)CH₂OMe | Br | Cl | 446.0048 |

TABLE 2-continued

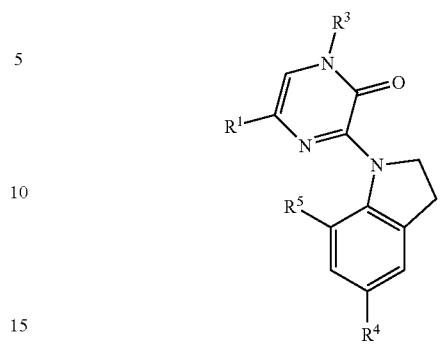

| Ex.# | R¹ | R³ | R⁴ | R⁵ | Mass Spec (M + H) Melting point ° C. |
|---|---|---|---|---|---|
| 549 | Br | CH(Et)CH₂OMe | OMe | Me | 422.1096 |
| 557 | Cl | CH(cBu)Et | OMe | Cl | 480.1270 |

TABLE 2A

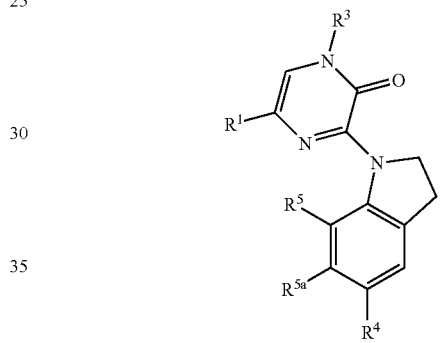

| Ex.# | R¹ | R³ | R⁴ | R⁵ | R⁵ᵃ | Mass Spec (M + H) |
|---|---|---|---|---|---|---|
| 513 | Cl | (1R)-CH(cPr)Et | OMe | Cl | F | 412.1019 |
| 519 | Cl | (1S)-CH(cPr)Et | OMe | Cl | F | 412.1001 |
| 522 | Cl | CH(Et)CH₂OMe | OMe | Cl | F | 416.0955 |
| 528 | Br | CH(Et)CH₂OMe | OMe | Cl | F | 460.0460 |

TABLE 2B

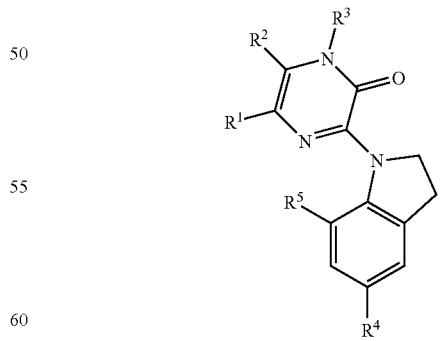

| Ex.# | R¹ | R² | R³ | R⁴ | R⁵ | Mass Spec (M + H) |
|---|---|---|---|---|---|---|
| 536 | Cl | Me | CH(Et)₂ | OMe | Cl | 396.1259 |
| 537 | Cl | Me | CH(cBu)Et | OMe | Cl | 422.1420 |

TABLE 3

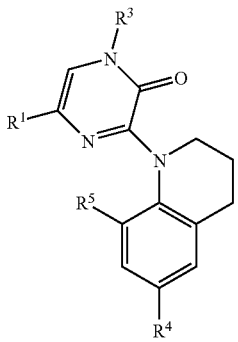

| Ex.# | R¹ | R³ | R⁴ | R⁵ | Mass Spec (M + H) |
|---|---|---|---|---|---|
| 550 | Cl | CH(Et)₂ | OMe | Br | 440.0750 |
| 551 | Cl | (1R)-CH(cPr)Et | OMe | Br | 452.0766 |
| 552 | Cl | (1S)-CH(cPr)Et | OMe | Br | 452.0734 |
| 553 | Cl | CH(Me)CH₂OMe | OMe | Br | 442.0557 |
| 554 | Br | CH(Et)CH₂OMe | OMe | Br | 500.0205 |
| 555 | Cl | CH(Et)CH₂OMe | OMe | Br | 456.0670 |

TABLE 4

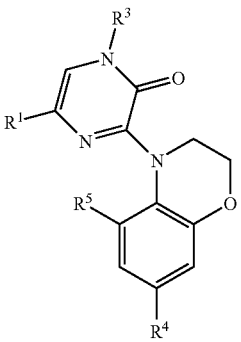

| Ex.# | R¹ | R³ | R⁴ | R⁵ | Mass Spec |
|---|---|---|---|---|---|
| 556 | Cl | (1R)-CH(cPr)Et | OMe | Br | 453.0459 |
| 558 | Cl | CH(cBu)Et | OMe | Br | 468.0665 |
| 559 | Cl | CH(cBu)Et | OMe | Cl | 424.1199 |
| 560 | Cl | (1S)-CH(cPr)Et | OMe | Br | 454.0518 |
| 561 | Cl | (1R)-CH(Et)CH₂OMe | OMe | Br | 457.0410 |
| 562 | Cl | (1S)-CH(Et)CH₂OMe | OMe | Br | 458.0457 |
| 563 | Cl | (1S)-CH(Me)CH₂OMe | OMe | Br | 444.0339 |
| 564 | Cl | CH(cBu)Et | OMe | H | 390.1595 |
| 565 | Cl | (1R)-CH(cPr)Et | OMe | H | 376.1452 |
| 566 | Br | (1R)-CH(Et)CH₂OMe | OMe | Br | 501.9992 |

Also provided herein are pharmaceutical compositions comprising compounds of this invention and a pharmaceutically acceptable carrier, which are media generally accepted in the art for the delivery of biologically active agents to animals, in particular, mammals. Pharmaceutically acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Example 1

4-(5,7-dichloro-2,3-dihydro-1H-indol-1-yl)-6-(1-ethylpropylamino)-2-methylpyrimidine Part A: A solution of 4,6-dichloro-2-methylpyrimidine (5 g, 30.70 mmol), 3-pentylamine (5.5 mL, 46.90 mmol) and diisopropylethyl amine (5.5 mL, 31.60 mmol) were heated at reflux in ethanol (40 mL) for 7 h. The reaction was partitioned between EtOAc (250 mL) and water (30 mL), and the EtOAc was washed with water, brine, dried and stripped in vacuo to give 7 g crude product, which was used in the next reaction without further purification.

Part B: A solution of 4-chloro-6-(1-ethylpropylamino)-2-methylpyrimidine (2.1 g, 10 mmol) and 5,7-dichloroindoline (2 g, 10.6 mmol) were heated at 190° C. in ethylene glycol (16 mL) for 4 h. The reaction mixture was partitioned between EtOAc (100 mL) and 0.5 N NaOH (50 mL) and the aqueous layer was extracted with EtOAc (100 mL), and the combined organic extracts were washed with water, brine, dried and stripped in vacuo. The residue was chromatographed on silica gel (30% EtOAc/hexanes, followed by 50% EtOAc/hexanes eluent) to give the product, which was crystallized from ether/hexanes (2.1 g, 57% yield).

Example 2

5-chloro-4-(5,7-dichloro-2,3-dihydro-1H-indol-1-yl)-6-(1-ethylpropylamino)-2-methylpyrimidine 4-(5,7-dichloro-2,3-dihydro-1H-indol-1-yl)-6-(1-ethylpropylamino)-2-methylpyrimidine (140 mg, 0.38 mmol) and N-chlorosuccinimide (60 mg, 0.45 mmol) were stirred in dry acetonitrile (5 mL) at 20° C. for 20 h. The reaction mixture was stripped in vacuo and the residue was chromatographed on silica gel using 20% EtOAc/hexanes to give the product, 5-chloro-4-(5,7-dichloro-2,3-dihydro-1H-indol-1-yl)-6-(1-ethylpropylamino)-2-methylpyrimidine (150 mg, 99% yield).

Example 3

5-bromo-4-(5,7-dichloro-2,3-dihydro-1H-indol-1-yl)-6-(1-ethylpropylamino)-2-methylpyrimidine 4-(5,7-dichloro-2,3-dihydro-1H-indol-1-yl)-6-(1-ethylpropylamino)-2-methylpyrimidine (1.15 g, 3.14 mmol) and pyridinium tribromide (1.16 g, 3.63 mmol) were stirred in dry dichloromethane (20 mL) at 20° C. for 16 h. The reaction mixture was quenched with saturated aqueous $Na_2S_2O_5$ (6 mL) and diluted with EtOAc (200 mL). The EtOAc was washed with water, brine, dried and stripped in vacuo. The residue was chromatographed on silica gel using 20% EtOAc/hexanes to give the product, 5-bromo-4-(5,7-dichloro-2,3-dihydro-1H-indol-1-yl)-6-(1-ethylpropylamino)-2-methylpyrimidine (1.30 g, 93% yield).

Example 4

4-(5,7-dichloro-2,3-dihydro-1H-indol-1-yl)-6-(1-ethylpropylamino)-5-iodo-2-methylpyrimidine 4-(5,7-Dichloro-2,3-dihydro-1H-indol-1-yl)-6-(1-ethylpropylamino)-2-methylpyrimidine, (365 mg, 1 mmol) was stirred in a two phase mixture of water (20 mL) and $CH_2Cl_2$ (2 mL) with $NaHCO_3$ (110 mg, 1.3 mmol) and $I_2$ (304 mg, 1.2 mmol) at 20° C. for 16 h. The reaction was quenched with saturated $Na_2S_2O_5$ (5 mL) and extracted with EtOAc (100 mL). The EtOAc was washed with brine, dried over ($MgSO_4$) and stripped in vacuo to give the title compound. The crude product can be used in the next reaction without further purification.

Example 5

5-cyano-4-(5,7-dichloro-2,3-dihydro-1H-indol-1-yl)-6-(1-ethylpropylamino)-2-methylpyrimidine 4-(5,7-Dichloro-2,3-dihydro-1H-indol-1-yl)-6-(1-ethylpropylamino)-5-iodo-2-methylpyrimidine (450 mg, 0.92 mmol) was heated at 140° C. in 5 mL DMF with CuCN (111 mg, 1.23 mmol) and NaCN (84 mg, 1.70 mmol) for 6 h. The reaction was poured into 20 mL 9:1 $NH_4Cl/NH_4OH$ and stirred for 20 min. The product was extracted with EtOAc (100 mL) and the EtOAc was washed with water (20 mL), brine, dried over ($MgSO_4$) and stripped in vacuo. The residue was chromatographed on silica gel using 20% EtOAc/hexanes as eluent to give the title compound 80 mg, mp 163–165° C.

Example 6

4-(5,7-dichloro-2,3-dihydro-1H-indol-1-yl)-6-(1-ethylpropylamino)-5-formyl-2-methylpyrimidine To a suspension of $AlCl_3$ (736 mg, 5.44 mmol) in $CHCl_3$ (5 mL) a solution of 4-(5,7-dichloro-2,3-dihydro-1H-indol-1-yl)-6-(1-ethylpropylamino)-2-methylpyrimidine (1.46 g, 4 mmol) in $CHCl_3$ was added at 0° C., followed by $Cl_2CHOMe$ (0.4 mL, 4.4 mmol). The reaction was stirred at 0° C. for 2 h and at 20° C. for 16 h. Then an additional amount of $Cl_2CHOMe$ was added (0.2 mL, 2.2 mmol) and the reaction was continued for 26 h. The mixture was poured into ice/water (50 mL) and after quenching it was basified with 1 N NaOH, extracted with EtOAc (2×100 mL each) and the combined organic extracts were washed with water, brine, dried over ($MgSO_4$) and stripped in vacuo. The residue was chromatographed on silica gel using 10% EtOAc/hexanes as eluent to give the product 4-(5,7-dichloro-2,3-dihydro-1H-indol-1-yl)-6-(1-ethylpropylamino)-5-formyl-2-methylpyrimidine (470 mg, 30% yield).

Example 7

4-(5,7-dichloro-2,3-dihydro-1H-indol-1-yl)-6-(1-ethylpropylamino)-5-hydroxymethyl-2-methylpyrimidine 4-(5,7-dichloro-2,3-dihydro-1H-indol-1-yl)-6-(1-ethylpropylamino)-5-formyl-2-methylpyrimidine, (50 mg, 0.13 mmol) was stirred with $NaBH_4$ (7 mg, 0.2 mmol) in dry ethanol (2 mL) at 0° C. for 2 h. The reaction was partitioned between EtOAc (100 mL) and water (20 mL) and the EtOAc was washed with brine, dried ($MgSO_4$) and stripped in vacuo. The residue was chromatographed on silica gel using 40% EtOAc/hexanes to give the product, 4-(5,7-dichloro-2,3-dihydro-1H-indol-1-yl)-6-(1-ethylpropylamino)-5-hydroxymethyl-2-methylpyrimidine (40 mg, 80% yield).

Example 53

4-(7-chloro-5-methoxy-2,3-dihydro-1H-indol-1-yl)-6-(1-ethylpropylamino)-2-methylpyrimidine Part A: A mixture of 7-chloro-5-methoxyindoline hydrochloride (4.45 g, 20.2 mmol) and anhydrous tetrahydrofuran (168 mL) was cooled to 0° C. while adding via syringe (1.0 M) sodium bis(trimethylsilyl)amide in tetrahydrofuran (39.0 mL, 39.0 mmol). Next was added portionwise 4,6-dichloro-2-methylpyrimidine (3.00 g, 18.4 mmol). The reaction mixture was kept cool at 0° C. for 1 hour. The bath was removed and allowed to warm to room temperature overnight. Another portion of sodium bis(trimethylsilyl)amide in tetrahydrofuran (9.2 mL, 9.2 mmol) was added and continued stirring for another 1.5 hours. One more portion of sodium bis(trimethylsilyl) amide in tetrahydrofuran (4.6 mL, 4.6 mmol) was added and stirred at room temperature for 2 hours. The reaction mixture was quenched with $H_2O$ and extracted with ethyl acetate. Combined the organics and washed with brine, dried over $MgSO_4$, filtered and concentrated. The crude product was chromatographed on silica gel using 20% ethyl acetate/hexanes as the eluent to afford a yellow solid (6.82 g). APCI-MS calcd for $C_{19}H_{25}ClN_4O$ (360.17): $(M+H)^+=361.4$, 100%; 363.5, 32%.

Part B: The product from part A (200 mg, 0.64 mmol) and 1-ethyl-propylamine (0.60 mL, 5.12 mmol) were stirred in a 80° C. oil bath over 7 days. The crude product was chromatographed on silica gel using a gradient from 40–50% ethyl acetate/hexanes as the eluent to afford the title compound (137 mg). Elemental analysis calcd for $C_{19}H_{25}ClN_4O$: C, 63.24; H, 6.98; N, 15.52. Found: C, 63.39; H, 7.06; N, 15.44.

Example 59

4-(7-chloro-5-methoxy-2,3-dihydro-1H-indol-1-yl)-5-cyano-6-(1-ethylpropylamino)-2-methylpyrimidine Part A: A mixture of 4,6-dichloro-2-methylpyrimidine (6.16 g, 37.8 mmol), 1-ethylpropyl-amine (6.6 mL, 56.7 mmol), N,N'-diisopropylamine (6.8 mL, 38.9 mmol), and ethanol (50 mL) were heated at reflux temperature for 7 hours. Water (80 mL) was added and extracted with ethyl acetate (400 mL). The organics were combined and washed with brine, dried over $MgSO_4$, filtered and concentrated to afford a white solid (8.24 g).

Part B: The product from part A (4.1 g, 19.2 mmol), 5-methoxy-7-chloro-indoline (3.7 g, 20.2 mmol) and ethylene glycol (20 mL) were heated to 190° C. for 11 hours. Aqueous 0.5 N NaOH solution (100 mL) was added and extracted with ethyl acetate. The organics were combined and washed with brine, dried over $MgSO_4$, filtered and concentrated. The crude oil was chromatographed on silica gel using a gradient from 30–50% ethyl acetate/hexanes as the eluent to afford a dark green foam. The product was rechromatographed using hexanes/ethyl acetate/methylene chloride (5:3:2 to 4:5:1) as the eluent to afford a dark green foam (3.60 g). APCI-MS calcd for $C_{19}H_{25}ClN_4O$ (360.17): $(M+H)^+=361.1$, 100%; 363.1, 39%.

Part C: The product from part B (3.60 g, 9.98 mmol) was dissolved in $CH_2Cl_2$ (4.0 mL) and $H_2O$ (14.0 mL). Next was added $NaHCO_3$ (1.09 g, 12.97 mmol) followed by iodine (2.56 g, 10.08 mmol) at 10–15° C. The reaction mixture was allowed to warm to room temperature overnight. A saturated $Na_2S_2O_5$ solution (125 mL) was added and extracted with ethyl acetate. The organics were combined and washed with brine, dried over $MgSO_4$, filtered and concentrated. The crude solid was chromatographed on silica gel using a gradient from 10–20% ethyl acetate/hexanes as the eluent to afford a white solid (2.53 g).

Part D: The product from part C (2.53 g, 5.20 mmol), CuCN (0.61 g, 6.76 mmol), NaCN (0.46 g, 9.36 mmol), and anhydrous N,N-dimethylformamide(25.0 mL) were heated in a 140° C. oil bath overnight. Water was added and extracted with ethyl acetate. The organics were combined and washed with $H_2O$, brine, dried over $MgSO_4$, filtered and concentrated. The crude solid was chromatographed on silica gel using 20% ethyl acetate/hexanes as the eluent to afford the title compound (1.91 g). mp 192–194° C. Elemental Analysis calcd for $C_{20}H_{24}ClN_5O$: C, 62.25; H, 6.278; N, 18.15. Found: C, 61.88; H, 6.18; N, 17.88.

Example 60

4-(7-chloro-5-methoxy-2,3-dihydro-1H-indol-1-yl)-6-(1-ethylpropylamino)-5-formyl-2-methylpyrimidine Part A: The product from part D, Example 59 (100 mg, 0.26 mmol) was dissolved in anhydrous diethyl ether (3.0 mL) and cooled to −78° C. A solution of 1.0 M diisobutylaluminum hydride in hexanes (0.52 mL, 0.52 mmol) added slowly via syringe to the reaction mixture. The solution was allowed to warm to room temperature over 1.5 hours. Water and 1.0 M HCl solution (3 mL) were added. Stirred the reaction mixture for 30 minutes. The aqueous was made basic with a 1.0 N NaOH solution and extracted with diethyl ether. The organics were combined and washed with brine, dried over $MgSO_4$, filtered and concentrated. The crude solid was chromatographed on silica gel using 20% ethyl acetate as the eluent to afford a yellow solid (70 mg). The solids were recrystallized from ether/methylene chloride/hexanes to afford a yellow solid (21 mg). Again the product was chromatographed on silica gel using 30% diethyl ether/hexanes as the eluent to afford the title compound (11 mg). mp 178–179° C. ESI-HRMS calcd for $C_{20}H_{26}ClN_4O_2$ $(M+H)^+$: 389.1745. Found: 389.1759.

Example 70

4-(7-chloro-5-methoxy-2,3-dihydro-1H-indol-1-yl)-6-[1-(1-methoxymethyl)propylamino]-2-methylpyrimidine The title compound was prepared by using similar procedures indicated in parts A and B of Example 59. APCI-MS calcd for $C_{19}H_{25}ClN_4O_2$ (376.17): $(M+H)^+=377.2$, 75%; 379.2, 29%.

Example 74

4-(7-chloro-5-methoxy-2,3-dihydro-1H-indol-1-yl)-5-iodo-6-[1-(1-methoxymethyl)propylamino]-2-methylpyrimidine The title compound was prepared by using similar procedures indicated in parts A, B and C of Example 59. mp 150–152° C. APCI-MS calcd for $C_{19}H_{24}ClIN_4O_2$ (502.06): $(M+H)^+=503.0$, 100.0%; 505.1, 35%.

Example 75

4-(7-chloro-5-methoxy-2,3-dihydro-1H-indol-1-yl)-5-cyano-6-[1-(1-methoxymethyl)propylamino]-2-methylpyrimidine The title compound was prepared in the similar manner to the procedure in Example 59. mp 182–183° C. Elemental Analysis calcd for $C_{20}H_{24}ClN_5O_2$: C, 59.77; H, 6.029; N, 17.43. Found: C, 59.40; H, 6.00; N, 17.13.

Example 76

4-(7-chloro-5-methoxy-2,3-dihydro-1H-indol-1-yl)-5-formyl-6-[1-(1-methoxymethyl)propylamino]-2-methylpyrimidine The title compound was prepared in the similar manner to the product in Example 60. mp 150–153° C. Elemental

Example 86

4-(7-chloro-5-methoxy-2,3-dihydro-1H-indol-1-yl)-6-[1-(1-ethyl-3-methoxy)propylamino]-2-methylpyrimidine The title compound was prepared by using similar procedures indicated in part A and B of Example 59. APCI-MS calcd for $C_{20}H_{27}ClN_4O_2$ (390.18): (M+H)$^+$=391.2, 100%; 393.2, 33%.

Example 91

4-(7-chloro-5-methoxy-2,3-dihydro-1H-indol-1-yl)-6-[1-(1-ethyl-3-methoxy)propylamino]-5-iodo-2-methylpyrimidine The product from Example 86 (1.97 g, 5.04 mmol), sodium bicarbonate (0.55 g, 6.55 mmol), water (7 mL), and methylene chloride (2 mL) were stirred and cooled to 10–15° C. Slowly added iodine (1.29 g, 5.09 mmol) portionwise. Allowed the reaction mixture to warm up slowly to room temperature. Stirred for two days. Added a solution of sodium metabisulfite and ethyl acetate. Stirred for 10 minutes. Separated the layers and extracted the water layer with ethyl acetate (2×). Combined the organics and washed with brine, dried over MgSO$_4$, filtered and concentrated. The crude product was chromatographed on silica gel using 10% ethyl acetate/hexanes as the eluent to afford the title compound (939 mg). mp 127–128° C. Elemental analysis calcd for $C_{20}H_{26}ClIN_4O_2$: C, 46.48; H, 5.07; N, 10.84. Found: C, 46.56; H, 5.02; N, 10.66.

Example 92

4-(7-chloro-5-methoxy-2,3-dihydro-1H-indol-1-yl)-5-cyano-6-[1-(1-ethyl-3-methoxy)propylamino]-2-methylpyrimidine The product from part A, Example 91 (912 mg, 1.76 mmol), copper(I) cyanide (205 mg, 2.29 mmol), sodium cyanide (155 mg, 3.17 mmol), and anhydrous dimethylforamide (11 mL) were stirred in a 140° C. oil bath overnight. The reaction mixture was partitioned between ethyl acetate and water. Extracted the aqueous layer with ethyl acetate (2×). Combined the organics and washed with brine, dried over MgSO$_4$, filtered and concentrated. The crude product was chromatographed on silica gel using 30% ethyl acetate/hexanes as the eluent to afford the title compound (156 mg). mp 137–139° C. Elemental analysis calcd for $C_{21}H_{26}ClN_5O_2$: C, 60.64; H, 6.30; N, 16.84. Found: C, 60.85; H, 6.30; N, 16.71.

The enantiomers of Example 92 were isolated using the following conditions: COLN: AD@27 C using diethylamine/ispropanol/hexanes (1/100/900) 1.5 mL/min, 260 NM. Collection #1: 39.2 mg, EE=>99%, collection #2: 36.8 mg, EE=>99% to afford the pure enantiomers: [a]$_D^{23}$ −10.8° (c 0.196, CHCl$_3$); [a]$_D^{23}$ +9.8°, (c=0.190, CHCl$_3$).

Example 309

4-(7-chloro-5-methoxy-2,3-dihydro-1H-indol-1-yl)-6-(1-methylbutylamino)-2-methylpyrimidine Part A: The product from part A, Example 53 (200 mg, 0.64 mmol) and 2-aminopentane (0.45 g, 5.12 mmol) were stirred in a 80° C. oil bath overnight. The crude product was chromatographed on silica gel using a gradient from 40–50% ethyl acetate/hexanes as the eluent to afford the title compound (187 mg). Elemental analysis calcd for $C_{19}H_{25}ClN_4O$: C, 63.24; H, 6.98; N, 15.52. Found: C, 62.92; H, 7.03; N, 15.54.

Example 310

4-(7-chloro-5-methoxy-2,3-dihydro-1H-indol-1-yl)-6-(1-methylpropylamino)-2-methylpyrimidine Part A: The product from part A, Example 53 (400 mg, 1.29 mmol), 2-butylamine (0.13 mL, 1.29 mmol) and ethanol (3 mL) were heated at reflux temperature for approximately 7 hours. The reaction mixture was concentrated. The crude product was chromatographed on silica gel using a gradient from 40–50% ethyl acetate/hexanes as the eluent to afford the title compound (309 mg). mp 102–105° C. Elemental Analysis calcd for $C_{18}H_{23}ClN_4O$: C, 62.33; H, 6.68; N, 16.15. Found: C, 62.50; H, 6.77; N, 16.04.

Example 311

4-(7-chloro-5-methoxy-2,3-dihydro-1H-indol-1-yl)-6-[1-(1-cyclobutyl)ethylamino]-2-methylpyrimidine Part A: The product from part A, Example 53 (200 mg, 0.64 mmol), 2-amino (1-methyl)cyclopropane hydrochloride (0.34 g, 2.56 mmol), N,N'-diisopropylethylamine (0.83 mL, 4.76 mmol), and anhydrous CH$_3$CN (0.5 mL) were stirred in a 80° C. oil bath over 7 days. Water was added and extracted with ethyl acetate. The organics were combined and washed with brine, dried over MgSO$_4$, filtered and concentrated. The crude product was chromatographed on silica gel to afford the title compound (0.47 mg). mp 125–128° C.

Example 401

5-Chloro-3-(5,7-dichloro-2,3-dihydro-1H-indol-1-yl)-1-(1-ethylpropyl)-2(1H)-pyrazinone

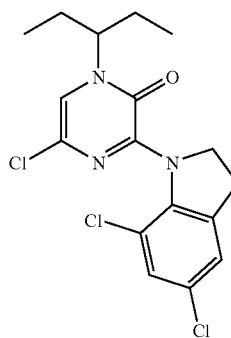

Prepared in a similar fashion as described for Example 413 using 3,5-dichloro-1-(1-ethylpropyl)-2(1H)-pyrazinone and 5,7-dichloroindoline as the starting materials. mp 168–170° C.; $^1$H NMR (300 MHz, CDCl$_3$): δ 7.18 (d, J=1.8 Hz, 1 H), 7.11 (d, J=2.2 Hz, 1 H), 6.78 (s, 1 H), 4.82–4.78 (m, 1 H), 4.35 (t, J=7.9 Hz, 2 H), 3.14 (t, J=8.1 Hz, 2 H), 1.88–1.74 (m, 2 H), 1.70–1.60 (m, 2 H), 0.88 (t, J=7.5 Hz, 6 H); HRMS (ESI) calcd for $C_{17}H_{19}N_3OCl_3$ (M+H)$^+$: 386.0594; found m/z 386.0614.

Example 402

5-Chloro-1-(1-cyclopropylpropyl)-3-(5,7-dichloro-2,3-dihydro-1H-indol-1-yl)-2(1H)-pyrazinone The title compound was prepared in a manner similar to the product of Example 413. $^1$H-NMR (CDCl$_3$) δ: 0.32 (1H, m), 0.51 (2H, m), 0.78 (1H, m), 0.94 (3H, t, J=7.4 Hz), 1.05 (1H, m), 1.86 (2H, m), 3.13 (2H, t, J=7.9 Hz), 4.06 (1H, m), 4.33 (2H, t, J=7.9 Hz), 7.00 (1H, s), 7.10 (1H, d, J=1.9 Hz), 7.17 (1H, d, J=1.8 Hz). MS (APCI+) m/z 398 (M+H)$^+$.

Example 404

5-Chloro-3-(5,7-dichloro-2,3-dihydro-1H-indol-1-yl)-1-[1-(methoxymethyl)propyl]-2(1H)-pyrazinone The title compound was prepared in a manner similar to the product of Example 413. $^1$H-NMR (CDCl$_3$) δ: 0.93 (3H, t, J=7.5 Hz), 1.83 (2H, m), 3.12 (2H, t, J=8.1 Hz), 3.35 (3H, s), 3.56 (1H, dd), 3.67 (1H, dd), 4.34 (2H, t, J=7.9 Hz), 4.93 (1H, m), 7.05 (1H, s), 7.10 (1H, d, J=1.9 Hz), 7.17 (1H, d, J=1.8 Hz). MS (APCI+) m/z 402 (M+H)$^+$.

Example 410

5-Chloro-3-(5,7-dichloro-2,3-dihydro-1H-indol-1-yl)-1-(1-ethyl-3-methoxypropyl)-2(1H)-pyrazinone

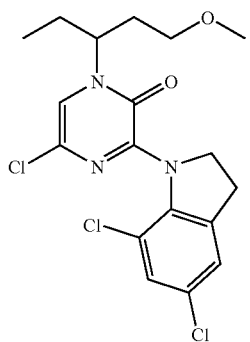

Prepared in a similar fashion as described for Example 413 using 3,5-dichloro-1-(1-ethyl-3-methoxypropyl)-2(1H)-pyrazinone and 5,7-dichloroindoline as the starting materials. mp 95–97° C.; $^1$H NMR (300 MHz, CDCl$_3$): δ 7.16 (d, J=2.2 Hz, 1 H), 7.09 (d, J=1.8 Hz, 1 H), 6.78 (s, 1 H), 4.89–4.82 (m, 1 H), 4.32 (t, J=8.1 Hz, 2 H), 3.39–3.27 (m, 2 H), 3.25 (s, 3 H), 3.11 (t, J=7.9 Hz, 2 H), 2.01–1.93 (m, 2 H), 1.84–1.72 (m, 2 H), 0.86 (t, J=7.5 Hz, 3 H); HRMS (ESI) calcd for C$_{18}$H$_{21}$N$_3$O$_2$Cl$_3$ (M+H)$^+$: 416.0699; found m/z 416.0717.

Example 413

5-Chloro-3-(7-chloro-5-methoxy-2,3-dihydro-1H-indol-1-yl)-1-[1-(methoxymethyl)propyl]-2(1H)-pyrazinone To 3,5-dichloro-1-[1-(methoxymethyl)propyl]-2(1H)-pyrazinone (1.0 g), prepared as described in Scheme 4, and 7-chloro-5-methoxyindoline hydrochloride (0.92 g), prepared as described in U.S. Pat. No. 6,245,769, stirring in anhydrous tetrahydrofuran (25 mL, 0° C.) was added sodium bis(trimethylsilyl)amide (1.0 M in THF, 11.9 mL, dropwise). The reaction mixture was allowed to come to ambient temperature and stirred 18 hours. Water was added, and the mixture was extracted with three portions of ethyl acetate. The combined ethyl acetate extracts were washed with brine, dried over MgSO$_4$, and concentrated. The crude product was chromatographed on silica gel using ethyl acetate/hexane (1:4) as eluent to afford the title compound (329 mg). mp 131–133° C. $^1$H-NMR (CDCl$_3$) δ: 0.93 (3H, t, J=7.3 Hz), 1.83 (2H, m), 3.09 (2H, t, J=7.6 Hz), 3.35 (3H, s), 3.56 (1H, dd), 3.67 (1H, dd), 3.78 (3H, s), 4.34 (2H, t, J=7.7 Hz), 4.94 (1H, m), 6.74 (2H, s), 6.99 (1H, s). MS (APCI+) m/z 398 (M+H)$^+$.

Example 420

5-Chloro-3-(7-chloro-5-methoxy-2,3-dihydro-1H-indol-1-yl)-1-(1-ethyl-3-methoxypropyl)-2(1H)-pyrazinone The title compound was prepared in a manner similar to the product of Example 413. $^1$H-NMR (CDCl$_3$) δ: 0.89 (3H, J=7.4 Hz), 1.80 (2H, m), 2.00 (2H, m), 3.10 (2H, t, J=7.7 Hz), 3.28 (3H, s), 3.34 (2H, m), 3.78 (3H, s), 4.35 (2H, t, J=7.9 Hz), 4.85 (1H, br), 6.74 (3H, s). MS (APCI+) m/z 412 (M+H)$^+$.

Example 431

5-Chloro-1-(1-ethylpropyl)-3-(5-methoxy-7-methyl-2,3-dihydro-1H-indol-1-yl)-2(1H)-pyrazinone

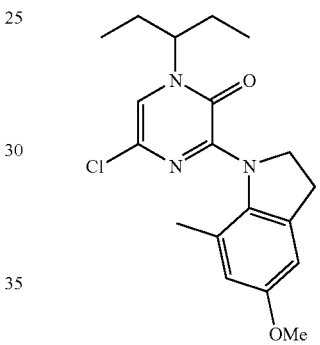

Prepared in a similar fashion as described for Example 413 using 3,5-dichloro-1-(1-ethylpropyl)-2(1H)-pyrazinone and 5-methoxy-7-methylindoline hydrochloride as the starting materials. mp 164–165° C.; $^1$H NMR (300 MHz, CDCl$_3$): δ 6.67 (s, 1 H), 6.66 (s, 1 H), 6.59 (d, J=2.2 Hz, 1 H), 4.82–4.80 (m, 1 H), 4.39 (t, J=7.9 Hz, 2 H), 3.79 (s, 3 H), 3.05 (t, J=7.7 Hz, 2 H), 2.06 (s, 3 H), 1.84–1.73 (m, 2 H), 1.70–1.59 (m, 2 H), 0.89 (t, J=7.3 Hz, 6 H); HRMS (ESI) calcd for C$_{19}$H$_{25}$N$_3$O$_2$Cl (M+H)$^+$: 362.1635; found m/z 362.1648.

Example 433

5-Chloro-3-(5-methoxy-7-methyl-2,3-dihydro-1H-indol-1-yl)-1-[1-(methoxymethyl)propyl]-2(1H)-pyrazinone The title compound was prepared in a manner similar to the product of Example 413. $^1$H-NMR (CDCl$_3$) δ: 0.94 (3H, t, J=7.5 Hz), 1.82 (2H, m), 2.06 (3H, s), 3.04 (2H, t, J=7.7 Hz), 3.36 (3H, s), 3.56 (1H, dd), 3.66 (1H, dd), 3.79 (3H, s), 4.38 (2H, t, J=7.7 Hz), 4.97 (1H, m), 6.59 (1H, s), 6.67 (1H, s), 6.92 (1H, s). MS (APCI+) m/z 378 (M+H)$^+$.

Example 440

5-Chloro-3-(5-methoxy-7-methyl-2,3-dihydro-1H-indol-1-yl)-1-(1-ethyl-3-methoxypropyl)-2(1H)-pyrazinone The title compound was prepared in a manner similar to the product of Example 413. $^1$H-NMR (CDCl$_3$) δ: 0.89 (3H, t, J=7.4 Hz), 1.80 (2H, m), 1.98 (2H, M), 2.06 (3H, s), 3.04 (2H, t, J=7.7 Hz), 3.29 (3H, s), 3.35 (2H, m), 3.79 (3H, s), 4.38 (2H, t, J=7.7 Hz), 4.89 (1H, br), 6.48 (1H, s), 6.60 (1H, S), 6.63 (1H, s). MS (APCI+) m/z 392 (M+H)+.

Example 441

3-(7-Bromo-5-methoxy-2,3-dihydro-1H-indol-1-yl)-5-chloro-1-(1-ethylpropyl)-2(1H)-pyrazinone

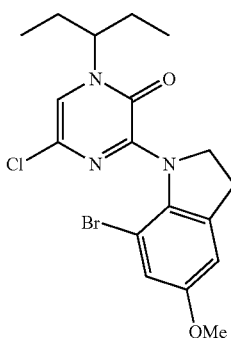

Prepared in a similar fashion as described for Example 413 using 3,5-dichloro-1-(1-ethylpropyl)-2(1H)-pyrazinone and 7-bromo-5-methoxyindoline hydrochloride as the starting materials. mp 130–132° C.; $^1$H NMR (300 MHz, CDCl$_3$): δ 6.92 (d, J=2.6 Hz, 1 H), 6.78 (d, J=2.2 Hz, 1 H), 6.73 (s, 1 H), 4.81 (brs, 1 H), 4.35 (t, J=7.7 Hz, 2 H), 3.78 (s, 3 H), 3.11 (t, J=7.7 Hz, 2 H), 1.87–1.73 (m, 2 H), 1.70–1.60 (m, 2 H), 0.89 (s, 6 H); HRMS (ESI) calcd for C$_{18}$H$_{22}$N$_3$O$_2$BrCl (M+H)+: 426.0584; found m/z 426.0606.

Example 443

5-Chloro-3-(7-bromo-5-methoxy-2,3-dihydro-1H-indol-1-yl)-1-[1-(methoxymethyl)propyl]-2(1H)-pyrazinone The title compound was prepared in a manner similar to the product of Example 413. $^1$H-NMR (CDCl$_3$) δ: 0.94 (3H, t, J=7.3 Hz), 1.82 (2H, m), 3.10 (2H, t, J=7.6 Hz), 3.35 (3H, s), 3.56 (1H, dd), 3.67 (1H, dd), 3.78 (3H, s), 4.35 (2H, t, J=7.9 Hz), 4.95 (1H, m), 6.78 (1H, d, J=2.2 Hz), 6.92 (1H, d, J=2.5 Hz), 7.00 (1H, s). MS (APCI+) m/z 442 (M+H)+.

Example 450

5-Chloro-3-(7-bromo-5-methoxy-2,3-dihydro-1H-indol-1-yl)-1-(1-ethyl-3-methoxypropyl)-2(1H)-pyrazinone The title compound was prepared in a manner similar to the product of Example 413. $^1$H-NMR (CDCl$_3$) δ: 0.89 (3H, t, J=7.4 Hz), 1.80 (2H, m), 2.00 (2H, m), 3.11 (2H, t, J=7.7 Hz), 3.28 (3H, s), 3.34 (2H, m), 3.78 (3H, s), 4.35 (2H, t, J=7.9 Hz), 4.85 (1H, br), 6.75 (1H, s), 6.78 (1H, d, J=2.2 Hz), 6.92 (1H, d, J=2.2 Hz). MS (ESI+) m/z 454 (M+H)+.

Example 451

3-(5,7-Dichloro-2,3-dihydro-1H-indol-1-yl)-1-(1-ethylpropyl)-5-methyl-2(1H)-pyrazinone

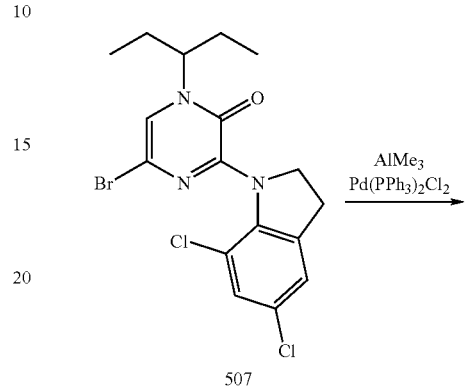

Prepared in a similar fashion as described for XXXII (Example 481, Part B) using 5-Bromo-3-(5,7-dichloro-2,3-dihydro-1H-indol-1-yl)-1-(1-ethylpropyl)-2(1H)-pyrazinone (Example 507) as the starting material. mp 137–139° C.; $^1$H NMR (300 MHz, CDCl$_3$): δ 7.14 (d, J=1.8 Hz, 1 H), 7.09 (d, J=2.2 Hz, 1 H), 6.54 (s, 1 H), 4.82 (brs, 1 H), 4.31 (t, J=8.1 Hz, 2 H), 3.14 (t, J=8.1 Hz, 2 H), 2.16 (s, 3 H), 1.83–1.74 (m, 2 H), 1.68–1.60 (m, 2 H), 0.86 (t, J=7.4 Hz, 6 H); HRMS (ESI) calcd for C$_{18}$H$_{22}$N$_3$OCl$_2$ (M+H)+: 366.1140; found m/z 366.1156.

Example 481

3-(5-Methoxy-7-methyl-2,3-dihydro-1H-indol-1-yl)-1-(1-ethylpropyl)-5-methyl-2(1H)-pyrazinone

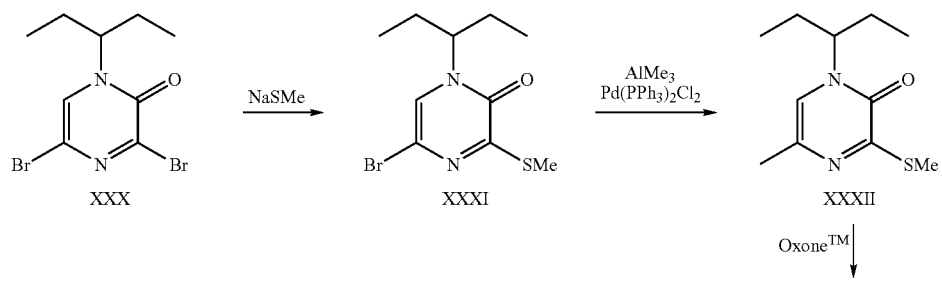

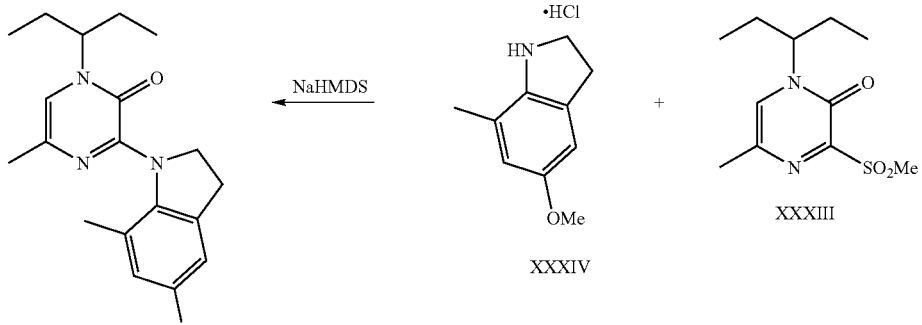

481

Part A. Preparation of 5-bromo-1-(1-ethylpropyl)-3-(methylthio)-2(1H)-pyrazinone (XXXI)

A solution of 3,5-dibromo-1-(1-ethylpropyl)-2(1H)-pyrazinone (XXX) (3.23 g, 10 mmol), prepared using the conditions described in US6159980 (Example 84, Part A), hereby incorporated by reference, and sodium thiomethoxide (701 mg, 10 mol) in THF (50 mL) was stirred at 25° C. for 72 h. The reaction mixture was diluted with water (75 mL) and ethyl acetate (75 mL). The organic phase was dried over (MgSO$_4$), filtered, and concentrated in vacuo to give crude residue. Purification by flash column chromatography (silica, ethyl acetate:hexane 1:4) gave the product XXXI (2.30 g, 82%) as a white solid.

Part B. Preparation of 1-(1-Ethylpropyl)-5-methyl-3-(methylthio)-2(1H)-pyrazinone (XXXII)

A solution of XXXI (2.0 g, 6.9 mmol) and dichlorobis(triphenylphosphine)palladium(II) (484 mg, 0.7 mmol) in THF (40 mL) was treated with trimethylaluminum (6.2 mL, 12.4 mmol, 2M/toluene) dropwise at 0° C. The reaction was refluxed for 4 h, cooled to 0° C. quenched with water (50 mL) and extracted with ethyl acetate (100 mL). The organic phase was dried (MgSO$_4$), filtered, and concentrated in vacuo to give crude residue. Purification by flash column chromatography (silica, ethyl acetate:hexane 1:1) gave the product XXXII (1.14 g, 73%) as a pale yellow solid.

Part C. Preparation of 1-(1-Ethylpropyl)-5-methyl-3-(methylsulfonyl)-2(1H)-pyrazinone (XXXIII)

A solution of XXXII (200 mg, 0.9 mmol) in THF (25 mL) was treated with Oxone™ (1.1 g, 1.8 mmol) portionwise as a solid at 25° C. The reaction mixture was stirred at 25° C. for 16 h and diluted with water (20 mL) and ethyl acetate (25 mL). The organic phase was dried (MgSO$_4$), filtered, and concentrated in vacuo to give the product XXXIII (153 mg, 67%) as a yellow oil.

Part D. Preparation of 3-(5-Methoxy-7-methyl-2,3-dihydro-1H-indol-1-yl)-1-(1-ethylpropyl)-5-methyl-2(1H)-pyrazinone (481)

Example 481 was prepared in a similar fashion as described for Example 413 using XXXIII and 5-methoxy-7-methylindoline hydrochloride as the starting materials. mp 138–140° C.; $^1$H NMR (300 MHz, CDCl$_3$): δ 6.68 (d, J=2.2 Hz, 1 H), 6.56 (d, J=2.2 Hz, 1 H), 6.44 (s, 1 H), 4.90–4.79 (brs, 1 H), 4.34 (t, J=7.9 Hz, 2 H), 3.78 (s, 3 H), 3.05 (t, J=7.9 Hz, 2 H), 2.11 (s, 3 H), 2.00 (s, 3 H), 1.82–1.71 (m, 2 H), 1.67–1.60 (m, 2 H), 0.87 (t, J=7.4 Hz, 6 H); HRMS (ESI) calcd for C$_{20}$H$_{28}$N$_3$O$_2$ (M+H)$^+$: 342.2182; found m/z 342.2196.

Example 501

5-Chloro-3-(7-chloro-5-methoxy-2,3-dihydro-1H-indol-1-yl)-1-(1-methylpropyl)-2(1H)-pyrazinone

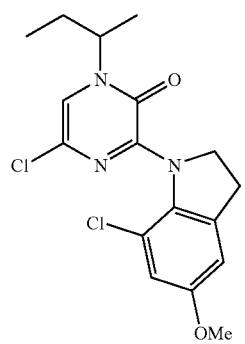

Prepared in a similar fashion as described for Example 413 using 1-sec-butyl-3,5-dichloro-2(1H)-pyrazinone and 7-chloro-5-methoxyindoline hydrochloride as the starting materials. mp 143–145° C.; $^1$H NMR (300 MHz, CDCl$_3$): δ 6.89 (s, 1 H), 6.77–6.72 (m, 2 H), 4.96–4.89 (m, 1 H), 4.34 (t, J=7.9 Hz, 2 H), 3.76 (s, 3 H), 3.07 (t, J=7.7 Hz, 2 H), 1.74–1.64 (m, 2 H), 1.33 (d, J=7.0 Hz, 3 H), 0.89 (t, J=7.6 Hz, 3 H); HRMS (ESI) calcd for C$_{17}$H$_{20}$N$_3$O$_2$Cl$_2$ (M+H)$^+$: 368.0933; found m/z 368.0927.

Example 502

3-(7-Bromo-5-methoxy-2,3-dihydro-1H-indol-1-yl)-5-chloro-1-(1-methylpropyl)-2(1H)-pyrazinone

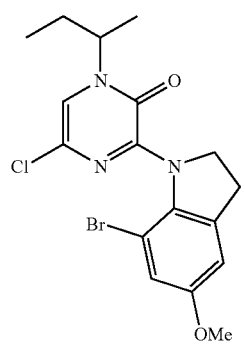

Prepared in a similar fashion as described for Example 413 using 1-sec-butyl-3,5-dichloro-2(1H)-pyrazinone and 7-bromo-5-methoxyindoline hydrochloride as the starting materials. mp 155–157° C.; $^1$H NMR (300 MHz, CDCl$_3$): δ 6.90 (d, J=2.6 Hz, 1 H), 6.78 (s, 1 H), 6.76 (d, J=2.1 Hz, 1 H), 4.99–4.87 (m, 1 H), 4.34 (t, J=7.7 Hz, 2 H), 3.76 (s, 3 H), 3.08 (t, J=7.7 Hz, 2 H), 1.74–1.65 (m, 2 H), 1.34 (d, J=7.0 Hz, 3 H), 0.89 (t, J=7.5 Hz, 3 H); HRMS (ESI) calcd for C$_{20}$H$_{22}$N$_3$O$_2$BrCl (M+H)$^+$: 412.0427; found m/z 412.0448.

Example 503

5-Chloro-3-(5-methoxy-7-methyl-2,3-dihydro-1H-indol-1-yl)-1-(1-methylpropyl)-2(1H)-pyrazinone

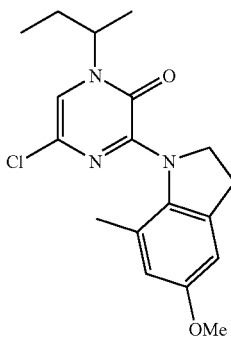

Prepared in a similar fashion as described for Example 413 using 1-sec-butyl-3,5-dichloro-2(1H)-pyrazinone and 5-methoxy-7-methylindoline hydrochloride as the starting materials. mp 176–178° C.; $^1$H NMR (300 MHz, CDCl$_3$): δ 6.70 (s, 1 H), 6.66 (d, J=2.2 Hz, 1 H), 6.57 (d, J=2.2 Hz, 1 H), 4.98–4.91 (m, 1 H), 4.38 (t, J=7.7 Hz, 2 H), 3.77 (s, 3 H), 3.02 (t, J=7.7 Hz, 2 H), 2.04 (s, 3 H), 1.74–1.64 (m, 2 H), 1.33 (d, J=6.9 Hz, 3 H), 0.90 (t, J=7.5 Hz, 3 H); HRMS (ESI) calcd for C$_{18}$H$_{23}$N$_3$O$_2$Cl (M+H)$^+$: 348.1479; found m/z 348.1490.

Example 504

5-Chloro-3-(5,7-dichloro-2,3-dihydro-1H-indol-1-yl)-2(1H)-1-(1-methylpropyl)-pyrazinone

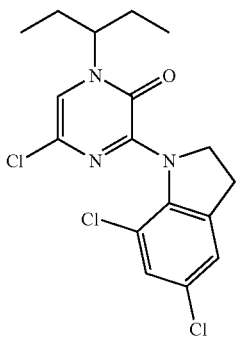

Prepared in a similar fashion as described for Example 413 using 1-sec-butyl-3,5-dichloro-2(1H)-pyrazinone and 5,7-dichloroindoline as the starting materials. mp 177–178° C.; $^1$H NMR (300 MHz, CDCl$_3$): δ 7.16 (d, J=1.9 Hz, 1 H), 7.09 (d, J=1.8 Hz, 1 H), 6.83 (s, 1 H), 4.98–4.86 (m, 1 H), 4.33 (t, J=8.1 Hz, 2 H), 3.11 (t, J=7.9 Hz, 2 H), 1.75–1.65 (m, 2 H), 1.34 (d, J=6.6 Hz, 3 H), 0.89 (t, J=7.4 Hz, 3 H); HRMS (ESI) calcd for C$_{16}$H$_{17}$N$_3$OCl$_3$ (M+H)$^+$: 372.0437; found m/z 372.0428.

Example 505

5-Bromo-3-(7-bromo-5-methoxy-2,3-dihydro-1H-indol-1-yl)-1-(1-ethylpropyl)-2(1H)-pyrazinone

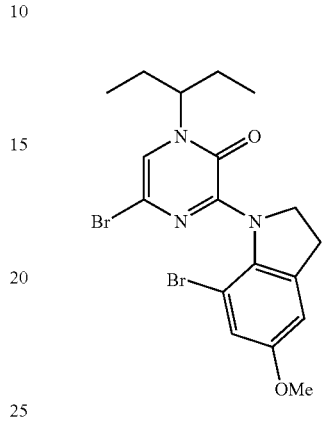

Prepared in a similar fashion as described for Example 413 using 3,5-dibromo-1-(1-ethylpropyl)-2(1H)-pyrazinone and 7-bromo-5-methoxyindoline hydrochloride as the starting materials. mp 133–135° C.; $^1$H NMR (300 MHz, CDCl$_3$): δ 6.92 (d, J=2.6 Hz, 1 H), 6.81 (s, 1 H), 6.78 (d, J=2.2 Hz, 1 H), 4.81–4.78 (m, 1 H), 4.35 (t, J=7.7 Hz, 2 H), 3.78 (s, 3 H), 3.11 (t, J=7.7 Hz, 2 H), 1.87–1.73 (m, 2 H), 1.70–1.60 (m, 2 H), 0.89 (t, J=7.3 Hz, 6 H); HRMS (ESI) calcd for C$_{18}$H$_{22}$N$_3$O$_2$Br$_2$ (M+H)$^+$: 470.0079; found m/z 470.0084.

Example 506

5-Bromo-1-(1-ethylpropyl)-3-(5-methoxy-7-methyl-2,3-dihydro-1H-indol-1-yl)-2(1H)-pyrazinone

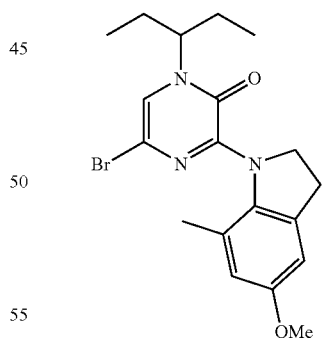

Prepared in a similar fashion as described for Example 413 using 3,5-dibromo-1-(1-ethylpropyl)-2(1H)-pyrazinone and 5-methoxy-7-methylindoline hydrochloride as the starting materials. mp 152–154° C.; $^1$H NMR (300 MHz, CDCl$_3$): δ 6.73 (s, 1 H), 6.67 (s, 1 H), 6.59 (d, J=1.9 Hz, 1 H), 4.84–4.76 (m, 1 H), 4.38 (t, J=7.7 Hz, 2 H), 3.78 (s, 3 H), 3.05 (t, J=7.7 Hz, 2 H), 2.06 (s, 3 H), 1.87–1.73 (m, 2 H), 1.70–1.59 (m, 2 H), 0.89 (t, J=7.3 Hz, 6 H); HRMS (ESI) calcd for C$_{19}$H$_{25}$N$_3$O$_2$Br (M+H)$^+$: 406.1130; found m/z 406.1125.

Example 507

5-Bromo-3-(5,7-dichloro-2,3-dihydro-1H-indol-1-yl)-1-(1-ethylpropyl)-2(1H)-pyrazinone

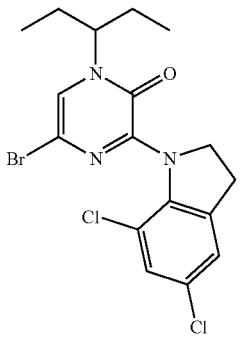

Prepared in a similar fashion as described for Example 413 using 3,5-dibromo-1-(1-ethylpropyl)-2(1H)-pyrazinone and 5,7-dichloroindoline as the starting materials. mp 158–160° C.; $^1$H NMR (300 MHz, CDCl$_3$): 7.18 (d, J=1.8 Hz, 1 H), 7.11 (d, J=2.2 Hz, 1 H), 6.85 (s, 1 H), 4.80–4.75 (m, 1 H), 4.34 (t, J=8.1 Hz, 2 H), 3.13 (t, J=8.1 Hz, 2 H), 1.88–1.74 (m, 2 H), 1.70–1.60 (m, 2 H), 0.88 (t, J=7.3 Hz, 6 H); HRMS (ESI) calcd for C$_{17}$H$_{19}$N$_3$OBrCl$_2$ (M+H)$^+$: 430.0089; found m/z 430.0109.

Example 508

5-Chloro-3-(7-chloro-5-methoxy-2,3-dihydro-1H-indol-1-yl)-1-[(1R)-1-cyclopropylpropyl]-2(1H)-pyrazinone

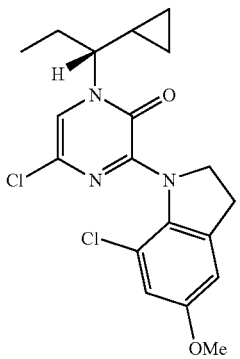

Prepared in a similar fashion as described for Example 413 using 3,5-dichloro-1-[(1R)-1-cyclopropylpropyl]-2 (1H)-pyrazinone and 7-chloro-5-methoxyindoline hydrochloride as the starting materials. mp 118–120° C.; $^1$H NMR (300 MHz, CDCl$_3$): δ 6.93 (s, 1 H), 6.71 (s, 2 H), 4.34–4.24 (m, 2 H), 4.09–4.01 (m, 1 H), 3.76 (s, 3 H), 3.08 (t, J=7.7 Hz, 2 H), 1.93–1.74 (m, 2 H), 1.06–0.98 (m, 1 H), 0.95–0.81 (m, 3 H), 0.79–0.72 (m, 1 H), 0.54–0.44 (m, 2 H), 0.34–0.22 (m, 1 H); HRMS (ESI) calcd for C$_{19}$H$_{22}$N$_3$O$_2$Cl$_2$ (M+H)$^+$: 394.1089; found m/z 394.1099.

Example 509

3-(7-Bromo-5-methoxy-2,3-dihydro-1H-indol-1-yl)-5-chloro-1-[(1R)-1-cyclopropylpropyl]-2(1H)-pyrazinone

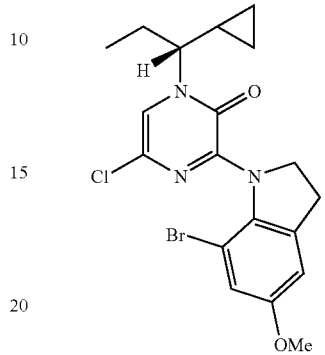

Prepared in a similar fashion as described for Example 413 using 3,5-dichloro-1-[(1R)-1-cyclopropylpropyl]-2 (1H)-pyrazinone and 7-bromo-5-methoxyindoline hydrochloride as the starting materials. mp 138–140° C.; $^1$H NMR (300 MHz, CDCl$_3$): δ 6.94 (s, 1 H), 6.89 (d, J=2.2 Hz, 1 H), 6.75 (d, J=2.5 Hz, 1 H), 4.34–4.24 (m, 2 H), 4.10–4.01 (m, 1 H), 3.76 (s, 3 H), 3.09 (t, J=7.9 Hz, 2 H), 1.91–1.74 (m, 2 H), 1.06–0.98 (m, 1 H), 0.95–0.86 (m, 3 H), 0.79–0.72 (m, 1 H), 0.53–0.44 (m, 2 H), 0.35–0.24 (m, 1 H); HRMS (CI) calcd for C$_{19}$H$_{22}$N$_3$O$_2$BrCl (M+H)$^+$: 438.0584; found m/z 438.0570.

Example 510

5-Chloro-1-[(1R)-1-cyclopropylpropyl]-3-(5-methoxy-7-methyl-2,3-dihydro-1H-indol-1-yl)-2(1H)-pyrazinone

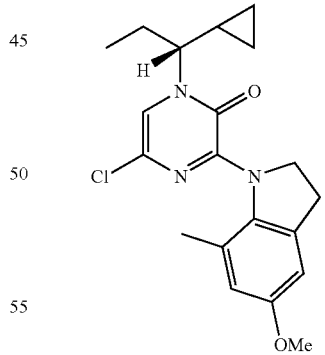

Prepared in a similar fashion as described for Example 413 using 3,5-dichloro-1-[(1R)-1-cyclopropylpropyl]-2 (1H)-pyrazinone and 5-methoxy-7-methylindoline hydrochloride as the starting materials. mp 160–162° C.; $^1$H NMR (300 MHz, CDCl$_3$): δ 6.89 (s, 1 H), 6.67 (d, J=2.2 Hz, 1 H), 6.59 (d, J=2.2 Hz, 1 H), 4.37 (t, J=7.7 Hz, 2 H), 4.29–4.04 (m, 1 H), 3.79 (s, 3 H), 3.04 (t, J=7.7 Hz, 2 H), 2.07 (s, 3 H), 1.95–1.75 (m, 2 H), 1.08–1.00 (m, 1 H), 0.95 (t, J=7.5 Hz, 3 H), 0.82–0.75 (m, 1 H), 0.57–0.47 (m, 2 H), 0.36–0.29 (m, 1 H); HRMS (ESI) calcd for $C_{20}H_{25}N_3O_2Cl$ (M+H)$^+$: 374.1635; found m/z 374.1617.

Example 511

5-Chloro-1-[(1R)-1-cyclopropylpropyl]-3-(5,7-dichloro-2,3-dihydro-1H-indol-1-yl)-2(1H)-pyrazinone

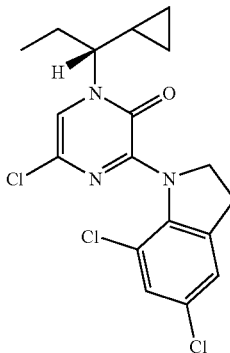

Prepared in a similar fashion as described for Example 413 using 3,5-dichloro-1-[(1R)-1-cyclopropylpropyl]-2(1H)-pyrazinone and 5,7-dichloroindoline as the starting materials. mp 166–168° C.; $^1$H NMR (300 MHz, CDCl$_3$): δ 7.15 (s, 1 H), 7.09 (s, 1 H), 6.99 (s, 1 H), 4.34–4.24 (m, 2 H), 4.08–3.99 (m, 1 H), 3.11 (t, J=8.1 Hz, 2 H), 2.12–2.05 (m, 1 H), 1.92–1.76 (m, 1 H), 1.05–1.00 (m, 1 H), 0.94–0.86 (m, 3 H), 0.80–0.71 (m, 1 H), 0.53–0.46 (m, 2 H), 0.33–0.21 (m, 1 H); HRMS (ESI) calcd for $C_{18}H_{19}N_3OCl_3$ (M+H)$^+$: 398.0594; found m/z 398.0575.

Example 512

5-Chloro-1-[(1R)-1-cyclopropylpropyl]-3-(5,7-dibromo-2,3-dihydro-1H-indol-1-yl)-2(1H)-pyrazinone

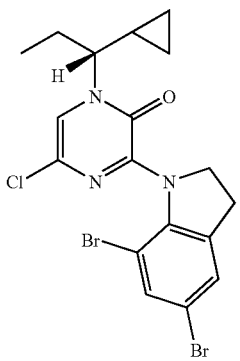

Part A: Indoline (2.2 g, 18.04 mmol), dissolved in dichloromethane (160 mL) was stirred with pyridinium tribromide (12 g, 37.6 mmol) for 16 h at 25° C. The reaction was quenched with sat NaHSO$_3$ (50 mL) and water (50 mL). The dichloromethane was separated, dried (MgSO$_4$) and stripped in vacuo. The residue was chromatographed on silica gel using 20% ethyl acetate/hexanes as eluent to give 5,7-dibromoindoline (4.2 g, 84% yield). $^1$H NMR(CDCl$_3$) δ 7.28 (m, 1H), 7.11 (s, 1H), 3.96 (s br, 1H ), 3.63 (t J=9 Hz, 1H), 3.13 (t J=9 Hz, 2H).

Part B: Prepared in a similar fashion as described for Example 413 using 3,5-dichloro-1-[(1R)-1-cyclopropylpropyl]-2(1H)-pyrazinone and 5,7-dibromoindoline as the starting materials. mp 164–165° C.; $^1$H NMR (300 MHz, CDCl$_3$): δ 7.42 (d, J=1.8 Hz, 1 H), 7.22 (d, J=1.5 Hz, 1 H), 6.96 (s, 1 H), 4.26 (t, J=8.1 Hz, 2 H), 3.99 (app. q, J=8.3 Hz, 1 H), 3.08 (t, J=7.9 Hz, 2 H), 1.94–1.69 (m, 2 H), 1.02–0.92 (m, 1 H), 0.87 (t, J=7.5 Hz, 3 H), 0.78–0.68 (m, 1 H), 0.50–0.39 (m, 2 H), 0.29–0.22 (m, 1 H); HRMS (ESI) calcd for $C_{18}H_{19}N_3OBr_2Cl$ (M+H)$^+$: 485.9583; found m/z 485.9592.

Example 513

5-Chloro-3-(7-chloro-6-fluoro-5-methoxy-2,3-dihydro-1H-indol-1-yl)-1-[(1R)-1-cyclopropylpropyl]-2(1H)-pyrazinone

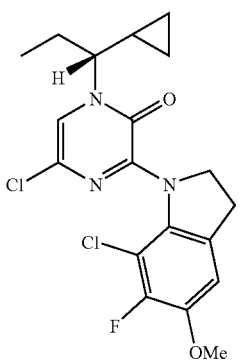

Prepared in a similar fashion as described for Example 413 using 3,5-dichloro-1-[(1R)-1-cyclopropylpropyl]-2(1H)-pyrazinone and 7-chloro-6-fluoro-5-methoxyindoline as the starting materials. mp 128–130° C.; $^1$H NMR (300 MHz, CDCl$_3$) δ 6.96 (s, 1 H), 6.79 (d, J=7.3 Hz, 1 H), 4.33 (t, J=7.9 Hz, 2 H), 4.08–4.00 (m, 1 H), 3.86 (s, 3 H), 3.08 (t, J=7.7 Hz, 2 H), 1.94–1.74 (m, 2 H), 1.07–0.97 (m, 1 H), 0.92 (t, J=7.3 Hz, 3 H), 0.80–0.73 (m, 1 H), 0.55–0.44 (m, 2 H), 0.34–0.27 (m, 1 H); HRMS (ESI) calcd for $C_{19}H_{21}N_3O_2Cl_2F$ (M+H)$^+$: 412.0995; found m/z 412.1019.

Example 514

5-Chloro-3-(7-chloro-5-methoxy-2,3-dihydro-1H-indol-1-yl)-1-[(1S)-1-cyclopropylpropyl]-2(1H)-pyrazinone

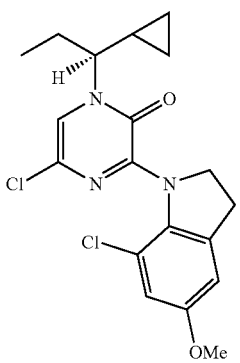

Prepared in a similar fashion as described for Example 413 using 3,5-dichloro-1-[(1S)-1-cyclopropylpropyl]-2(1H)-pyrazinone and 7-chloro-5-methoxyindoline hydrochloride as the starting materials. mp 128–130° C.; $^1$H NMR (300 MHz, CDCl$_3$): δ 6.93 (s, 1 H), 6.71 (s, 2 H), 4.34–4.24 (m, 2 H), 4.11–3.99 (m, 1 H), 3.75 (s, 3 H), 3.08 (t, J=7.9 Hz, 2 H), 1.93–1.73 (m, 2 H), 1.06–0.99 (m, 1 H), 0.92 (t, J=7.3

Hz, 3 H), 0.79–0.72 (m, 1 H), 0.54–0.43 (m, 2 H), 0.34–0.24 (m, 1 H); HRMS (ESI) calcd for $C_{19}H_{22}N_3O_2Cl_2$ (M+H)$^+$: 394.1089; found m/z 394.1088.

Example 515

3-(7-Bromo-5-methoxy-2,3-dihydro-1H-indol-1-yl)-5-chloro-1-[(1S)-1-cyclopropylpropyl]-2(1H)-pyrazinone

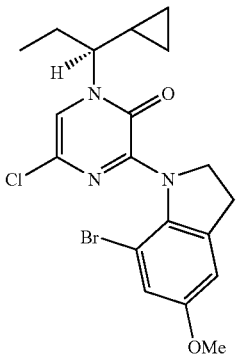

Prepared in a similar fashion as described for Example 413 using 3,5-dichloro-1-[(1S)-1-cyclopropylpropyl]-2(1H)-pyrazinone and 7-bromo-5-methoxyindoline hydrochloride as the starting materials. mp 138–140° C.; $^1$H NMR (300 MHz, CDCl$_3$): δ 6.94 (s, 1 H), 6.89 (d, J=2.2 Hz, 1 H), 6.76 (d, J=2.2 Hz, 1 H), 4.34–4.24 (m, 2 H), 4.10–4.01 (m, 1 H), 3.76 (s, 3 H), 3.09 (t, J=7.9 Hz, 2 H), 1.94–1.74 (m, 2 H), 1.06–0.98 (m, 1 H), 0.95–0.86 (m, 3 H), 0.79–0.72 (m, 1 H), 0.54–0.44 (m, 2 H), 0.35–0.22 (m, 1 H); HRMS (ESI) calcd for $C_{19}H_{22}N_3O_2BrCl$ (M+H)$^+$: 438.0584; found m/z 438.0605.

Example 516

5-Chloro-1-[(1S)-1-cyclopropylpropyl]-3-(5-methoxy-7-methyl-2,3-dihydro-1H-indol-1-yl)-2(1H)-pyrazinone

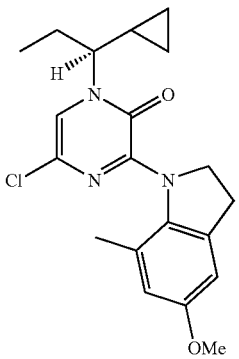

Prepared in a similar fashion as described for Example 413 using 3,5-dichloro-1-[(1S)-1-cyclopropylpropyl]-2(1H)-pyrazinone and 5-methoxy-7-methylindoline hydrochloride as the starting materials. mp 156–158° C.; $^1$H NMR (300 MHz, CDCl$_3$): δ 6.87 (s, 1 H), 6.65 (d, J=1.8 Hz, 1 H), 6.57 (d, J=2.2 Hz, 1 H), 4.35 (t, J=7.7 Hz, 2 H), 4.10–4.02 (m, 1 H), 3.77 (s, 3 H), 3.02 (t, J=7.7 Hz, 2 H), 2.05 (s, 3 H), 1.93–1.73 (m, 2 H), 1.06–0.99 (m, 1 H), 0.95–0.87 (m, 3 H), 0.80–0.73 (m, 1 H), 0.55–0.44 (m, 2 H), 0.34–0.23 (m, 1 H); HRMS (ESI) calcd for $C_{20}H_{25}N_3O_2Cl$ (M+H)$^+$: 374.1635; found m/z 374.1634.

Example 517

5-Chloro-1-[(1S)-1-cyclopropylpropyl]-3-(5,7-dichloro-2,3-dihydro-1H-indol-1-yl)-2(1H)-pyrazinone

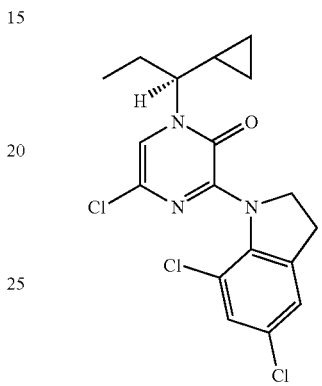

Prepared in a similar fashion as described for Example 413 using 3,5-dichloro-1-[(1S)-1-cyclopropylpropyl]-2(1H)-pyrazinone and 5,7-dichloroindoline as the starting materials. mp 157–159° C.; $^1$H NMR (300 MHz, CDCl$_3$): δ 7.15 (s, 1 H), 7.09 (s, 1 H), 6.99 (s, 1 H), 4.34–4.24 (m, 2 H), 4.08–3.99 (m, 0.5 H), 3.11 (t, J=7.9 Hz, 2 H), 2.42–2.36 (m, 0.5 H), 2.16–2.00 (m, 1 H), 1.94–1.74 (m, 1 H), 1.07–0.99 (m, 1 H), 0.94–0.86 (m, 3 H), 0.80–0.71 (m, 1 H), 0.53–0.42 (m, 2 H), 0.36–0.20 (m, 1 H); HRMS (ESI) calcd for $C_{18}H_{19}N_3OCl_3$ (M+H)$^+$: 398.0594; found m/z 398.0602.

Example 518

5-Chloro-1-[(1S)-1-cyclopropylpropyl]-3-(5,7-dibromo-2,3-dihydro-1H-indol-1-yl)-2(1H)-pyrazinone

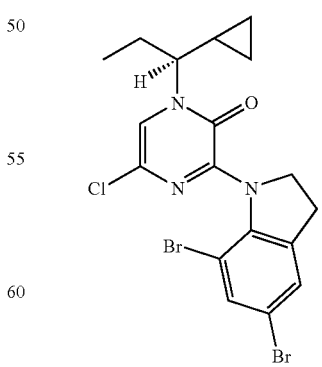

Prepared in a similar fashion as described for Example 413 using 3,5-dichloro-1-[(1S)-1-cyclopropylpropyl]-2(1H)-pyrazinone and 5,7-dibromoindoline as the starting materials. mp 165° C.; ¹H NMR (300 MHz, CDCl₃): δ 7.49 (d, J=1.8 Hz, 1 H), 7.29 (d, J=1.8 Hz, 1 H), 7.02 (s, 1 H), 4.32 (t, J=7.9 Hz, 2 H), 4.06 (app. q, J=8.0 Hz, 1 H), 3.15 (t, J=8.1 Hz, 2 H), 1.99–1.74 (m, 2 H), 1.11–0.99 (m, 1 H), 0.94 (t, J=7.5 Hz, 3 H), 0.88–0.73 (m, 1 H), 0.57–0.46 (m, 2 H), 0.39–0.27 (m, 1 H); HRMS (CI) calcd for C₁₈H₁₉N₃OBr₂Cl (M+H)⁺: 485.9583; found m/z 485.9604.

Example 519

5-Chloro-3-(7-chloro-6-fluoro-5-methoxy-2,3-dihydro-1H-indol-1-yl)-1-[(1S)-1-cyclopropylpropyl]-2(1H)-pyrazinone

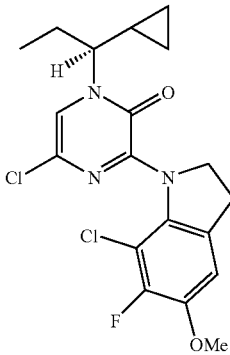

Prepared in a similar fashion as described for Example 413 using 3,5-dichloro-1-[(1S)-1-cyclopropylpropyl]-2(1H)-pyrazinone and 7-chloro-6-fluoro-5-methoxyindoline as the starting materials. mp 127–129° C.; ¹H NMR (300 MHz, CDCl₃): δ 6.96 (s, 1 H), 6.79 (d, J=7.3 Hz, 1 H), 4.33 (t, J=7.9 Hz, 2 H), 4.11–4.00 (m, 1 H), 3.86 (s, 3 H), 3.08 (t, J=7.7 Hz, 2 H), 1.94–1.74 (m, 2 H), 1.07–0.99 (m, 1 H), 0.92 (t, J=7.3 Hz, 3 H), 0.80–0.73 (m, 1 H), 0.55–0.44 (m, 2 H), 0.34–0.25 (m, 1 H); HRMS (ESI) calcd for C₁₉H₂₁N₃O₂Cl₂F (M+H)⁺: 412.0995; found m/z 412.1001.

Example 520

5-Chloro-3-(5,7-dichloro-2,3-dihydro-1H-indol-1-yl)-1-[(1R)-2-methoxy-1-methylethyl]-2(1H)-pyrazinone

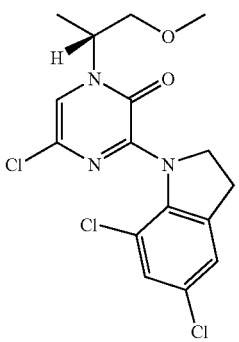

Prepared in a similar fashion as described for Example 413 using 3,5-dichloro-1-[(1R)-2-methoxy-1-methylethyl]-2(1H)-pyrazinone and 5,7-dichloroindoline as the starting materials. mp 93–95° C.; ¹H NMR (300 MHz, CDCl₃): δ 7.18 (s, 1 H), 7.11 (s, 1 H), 7.06 (s, 1 H), 4.35 (t, J=7.9 Hz, 2 H), 3.62–3.56 (m, 3 H), 3.36 (s, 3 H), 3.12 (t, J=8.1 Hz, 2 H), 0.90–0.86 (m, 3 H); HRMS (ESI) calcd for C₁₆H₁₇N₃O₂Cl₃ (M+H)⁺: 388.0386; found m/z 388.0358.

Example 521

5-Chloro-3-(5,7-dibromo-2,3-dihydro-1H-indol-1-yl)-1-[(1R)-2-methoxy-1-methylethyl]-2(1H)-pyrazinone

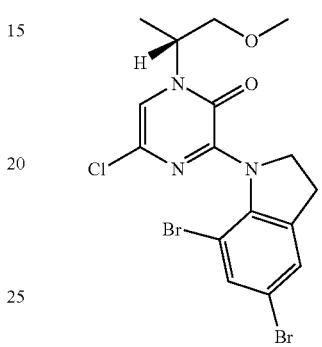

Prepared in a similar fashion as described for Example 413 using 3,5-dichloro-1-[(1R)-2-methoxy-1-methylethyl]-2(1H)-pyrazinone and 5,7-dibromoindoline as the starting materials. mp 119–120° C.; ¹H NMR (300 MHz, CDCl₃): δ 7.47 (d, J=1.8 Hz, 1 H), 7.27 (d, J=1.8 Hz, 1 H), 7.06 (s, 1 H), 5.14–5.09 (m, 1 H), 4.32 (t, J=7.9 Hz, 2 H), 3.62–3.52 (m, 2 H), 3.34 (s, 3 H), 3.11 (t, J=8.1 Hz, 2 H), 1.40 (d, J=7.0 Hz, 3 H); HRMS (CI) calcd for C₁₆H₁₆N₃O₂Br₂Cl (M+H)⁺: 474.9298; found m/z 474.9285.

Example 522

5-Chloro-3-(7-chloro-6-fluoro-5-methoxy-2,3-dihydro-1H-indol-1-yl)-1-[1-(methoxymethyl)propyl]-2(1H)-pyrazinone

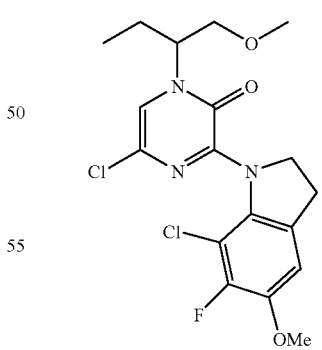

Prepared in a similar fashion as described for Example 413 using 3,5-dichloro-1-[1-(methoxymethyl)propyl]-2(1H)-pyrazinone and 7-chloro-6-fluoro-5-methoxyindoline as the starting materials. mp 140–142° C.; ¹H NMR (300 MHz, CDCl₃): δ 7.00 (s, 1 H), 6.79 (d, J=7.3 Hz, 1 H), 4.97–4.85 (m, 1 H), 4.34 (t, J=7.6 Hz, 2 H), 3.86 (s, 3 H), 3.65 (dd, J=10.6, 5.8 Hz, 1 H), 3.54 (dd, J=10.6, 3.7 Hz, 1

H), 3.33 (s, 3 H), 3.07 (t, J=7.5 Hz, 2 H), 1.90–1.72 (m, 2 H), 0.92 (t, J=7.5 Hz, 3 H); HRMS (ESI) calcd for $C_{18}H_{21}N_3O_3Cl_2F$ (M+H)$^+$: 416.0944; found m/z 416.0955.

Example 523

3-(7-Bromo-5-methoxy-2,3-dihydro-1H-indol-1-yl)-5-chloro-1-[(1R)-1-(methoxymethyl)propyl]-2(1H)-pyrazinone

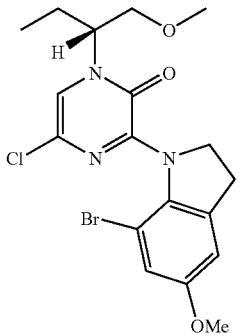

Prepared in a similar fashion as described for Example 413 using 3,5-dichloro-1-[(1R)-1-(methoxymethyl)propyl]-2(1H)-pyrazinone and 7-bromo-5-methoxyindoline hydrochloride as the starting materials. mp 102–104° C.; $^1$H NMR (300 MHz, CDCl$_3$): δ 7.00 (s, 1 H), 6.92 (d, J=2.5 Hz, 1 H), 6.78 (d, J=2.2 Hz, 1 H), 4.99–4.90 (m, 1 H), 4.35 (t, J=7.7 Hz, 2 H), 3.78 (s, 3 H), 3.67 (dd, J=10.6, 5.5 Hz, 1 H), 3.56 (dd, J=10.6, 3.7 Hz, 1 H), 3.35 (s, 3 H), 3.10 (t, J=7.9 Hz, 2 H), 1.92–1.72 (m, 2 H), 0.93 (t, J=7.3 Hz, 3 H); HRMS (CI) calcd for $C_{18}H_{22}N_3O_3BrCl$ (M+H)$^+$: 442.0533; found m/z 442.0532.

Example 524

5-Chloro-3-(5,7-dichloro-2,3-dihydro-1H-indol-1-yl)-1-[(1R)-1-(methoxymethyl)propyl]-2(1H)-pyrazinone

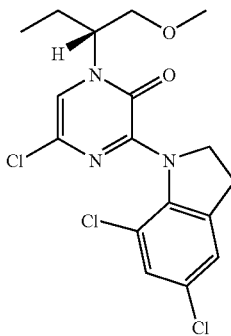

Prepared in a similar fashion as described for Example 413 using 3,5-dichloro-1-[(1R)-1-(methoxymethyl)propyl]-2(1H)-pyrazinone and 5,7-dichloroindoline as the starting materials. mp 143–146° C.; $^1$H NMR (300 MHz, CDCl$_3$): δ 7.15 (d, J=1.8 Hz, 1 H), 7.09 (d, J=1.8 Hz, 1 H), 7.03 (s, 1 H), 4.94–4.90 (m, 1 H), 4.32 (t, J=8.1 Hz, 2 H), 3.65 (dd, J=10.6, 5.5 Hz, 1 H), 3.54 (dd, J=10.7, 3.3 Hz, 1 H), 3.33 (s, 3 H), 3.10 (t, J=8.1 Hz, 2 H), 1.88–1.70 (m, 2 H), 0.91 (t, J=7.3 Hz, 3 H); HRMS (ESI) calcd for $C_{17}H_{19}N_3O_2Cl_3$ (M+H)$^+$: 402.0543; found m/z 402.0568.

Example 525

5-Bromo-3-(7-bromo-5-methoxy-2,3-dihydro-1H-indol-1-yl)-1-[(1R)-1-(methoxymethyl)propyl]-2(1H)-pyrazinone

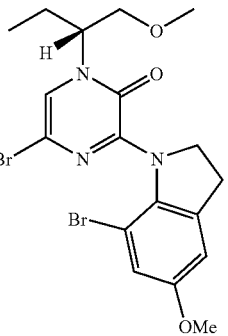

Prepared in a similar fashion as described for Example 413 using 3,5-dibromo-1-[(1R)-1-(methoxymethyl)propyl]-2(1H)-pyrazinone and 7-bromo-5-methoxyindoline hydrochloride as the starting materials. mp 122–123° C.; $^1$H NMR (300 MHz, CDCl$_3$): δ 7.07 (s, 1 H), 6.92 (d, J=2.6 Hz, 1 H), 6.77 (d, J=2.2 Hz, 1 H), 4.95–4.80 (m, 1 H), 4.34 (t, J=7.7 Hz, 2 H), 3.78 (s, 3 H), 3.66 (dd, J=10.7, 5.5 Hz, 1 H), 3.56 (dd, J=10.3, 3.3 Hz, 1 H), 3.35 (s, 3 H), 3.10 (t, J=7.7 Hz, 2 H), 1.87–1.74 (m, 2 H), 0.93 (t, J=7.4 Hz, 3 H); HRMS (ESI) calcd for $C_{18}H_{22}N_3O_3Br_2$ (M+H)$^+$: 486.0028; found m/z 486.0018.

Example 526

5-Bromo-3-(5-methoxy-7-methyl-2,3-dihydro-1H-indol-1-yl)-1-[(1R)-1-(methoxymethyl)propyl]-2(1H)-pyrazinone

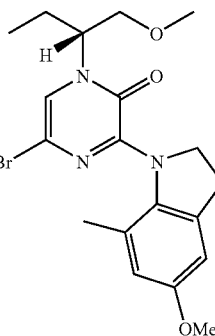

Prepared in a similar fashion as described for Example 413 using 3,5-dibromo-1-[(1R)-1-(methoxymethyl)propyl]-2(1H)-pyrazinone and 5-methoxy-7-methylindoline hydrochloride as the starting materials. mp 116–118° C.; $^1$H NMR (300 MHz, CDCl$_3$): δ 6.98 (s, 1 H), 6.67 (s, 1 H), 6.58 (d, J=2.2 Hz, 1 H), 4.97–4.95 (m, 1 H), 4.38 (t, J=7.9 Hz, 2 H), 3.79 (s, 3 H), 3.66 (dd, J=10.6, 5.9 Hz, 1 H), 3.56 (dd, J=10.6, 3.6 Hz, 1 H), 3.36 (s, 3 H), 3.04 (t, J=7.9 Hz, 2 H), 2.06 (s, 3 H), 1.92–1.72 (m, 2 H), 0.94 (t, J=7.5 Hz, 3 H); HRMS (ESI) calcd for $C_{19}H_{25}N_3O_3Br$ (M+H)$^+$: 422.1079; found m/z 422.1097.

Example 527

5-Bromo-3-(5,7-dichloro-2,3-dihydro-1H-indol-1-yl)-1-[(1R)-1-(methoxymethyl)propyl]-2(1H)-pyrazinone

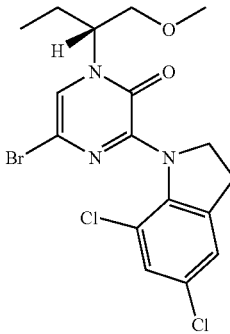

Prepared in a similar fashion as described for Example 413 using 3,5-dibromo-1-[(1R)-1-(methoxymethyl)propyl]-2(1H)-pyrazinone and 5,7-dichloroindoline as the starting materials. mp 150–152° C.; $^1$H NMR (300 MHz, CDCl$_3$): δ 7.18 (d, J=2.2 Hz, 1 H), 7.12 (s, 1 H), 7.10 (d, J=1.8 Hz, 1 H), 4.95–4.90 (m, 1 H), 4.34 (t, J=8.1 Hz, 2 H), 3.67 (dd, J=10.6, 5.8 Hz, 1 H), 3.55 (dd, J=10.6, 3.5 Hz, 1 H), 3.35 (s, 3 H), 3.12 (t, J=8.1 Hz, 2 H), 1.92–1.72 (m, 2 H), 0.93 (t, J=7.5 Hz, 3 H); HRMS (ESI) calcd for $C_{17}H_{19}N_3O_2BrCl_2$ (M+H)$^+$: 446.0038; found m/z 446.0008.

Example 528

5-Bromo-3-(7-chloro-6-fluoro-5-methoxy-2,3-dihydro-1H-indol-1-yl)-1-[(1R)-1-(methoxymethyl)propyl]-2(1H)-pyrazinone

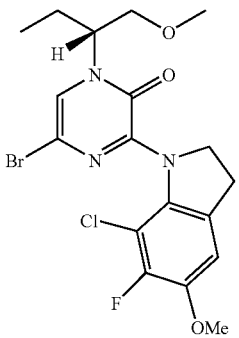

Prepared in a similar fashion as described for Example 413 using 3,5-dibromo-1-[(1R)-1-(methoxymethyl)propyl]-2(1H)-pyrazinone and 7-chloro-6-fluoro-5-methoxyindoline as the starting materials. mp 150–152° C.; $^1$H NMR (300 MHz, CDCl$_3$): δ 7.09 (s, 1 H), 6.81 (d, J=7.3 Hz, 1 H), 4.95–4.90 (m, 1 H), 4.35 (t, J=8.1 Hz, 2 H), 3.89 (s, 3 H), 3.67 (dd, J=10.6, 5.8 Hz, 1 H), 3.56 (dd, J=10.6, 3.5 Hz, 1 H), 3.36 (s, 3 H), 3.09 (t, J=8.4 Hz, 2 H), 1.96–1.77 (m, 2 H), 0.94 (t, J=7.5 Hz, 3 H); HRMS (ESI) calcd for $C_{18}H_{21}N_3O_3BrClF$ (M+H)$^+$: 460.0439; found m/z 460.0460.

Example 529

3-(7-Bromo-5-methoxy-2,3-dihydro-1H-indol-1-yl)-5-chloro-1-[(1S)-1-(methoxymethyl)propyl]-2(1H)-pyrazinone

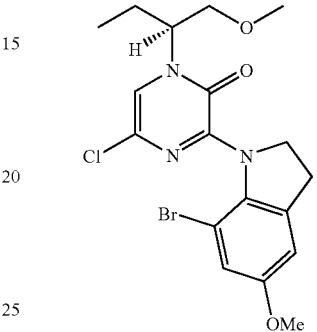

Prepared in a similar fashion as described for Example 413 using 3,5-dichloro-1-[(1S)-1-(methoxymethyl)propyl]-2(1H)-pyrazinone and 7-bromo-5-methoxyindoline hydrochloride as the starting materials. mp 100–102° C.; $^1$H NMR (300 MHz, CDCl$_3$): δ 7.00 (s, 1 H), 6.92 (d, J=2.5 Hz, 1 H), 6.78 (d, J=2.6 Hz, 1 H), 4.99–4.90 (m, 1 H), 4.35 (t, J=7.7 Hz, 2 H), 3.78 (s, 3 H), 3.67 (dd, J=10.6, 5.7 Hz, 1 H), 3.56 (dd, J=10.6, 3.5 Hz, 1 H), 3.35 (s, 3 H), 3.10 (t, J=7.7 Hz, 2 H), 1.92–1.72 (m, 2 H), 0.93 (t, J=7.3 Hz, 3 H); HRMS (ESI) calcd for $C_{18}H_{22}N_3O_3BrCl$ (M+H)$^+$: 442.0533; found m/z 442.0516.

Example 530

5-Chloro-3-(5,7-dichloro-2,3-dihydro-1H-indol-1-yl)-1-[(1S)-1-(methoxymethyl)propyl]-2(1H)-pyrazinone

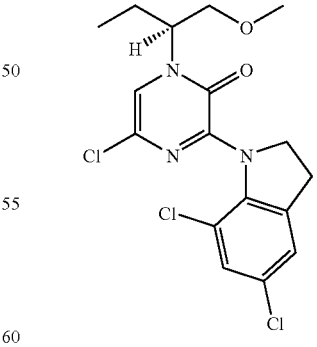

Prepared in a similar fashion as described for Example 413 using 3,5-dichloro-1-[(1S)-1-(methoxymethyl)propyl]-2(1H)-pyrazinone and 5,7-dichloroindoline as the starting materials. mp 143–146° C.; $^1$H NMR (300 MHz, CDCl$_3$): δ 7.16 (d, J=1.9 Hz, 1 H), 7.09 (d, J=1.9 Hz, 1 H), 7.03 (s, 1 H), 4.93–4.88 (m, 1 H), 4.32 (t, J=8.1 Hz, 2 H), 3.65 (dd, J=10.6, 5.5 Hz, 1 H), 3.54 (dd, J=10.6, 3.5 Hz, 1 H), 3.33 (s, 3 H), 3.11 (t, J=8.1 Hz, 2 H), 1.90–1.70 (m, 2 H), 0.91 (t, J=7.5 Hz, 3 H); HRMS (ESI) calcd for $C_{17}H_{19}N_3O_2Cl_3$ (M+H)$^+$: 402.0543; found m/z 402.0520.

Example 531

5-Bromo-3-(5,7-dichloro-2,3-dihydro-1H-indol-1-yl)-1-[(1S)-1-(methoxymethyl)propyl]-2(1H)-pyrazinone

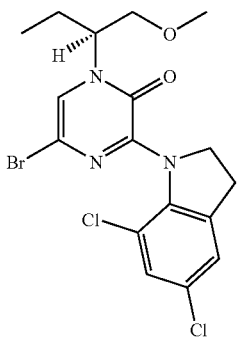

Prepared in a similar fashion as described for Example 413 using 3,5-dibromo-1-[(1S)-1-(methoxymethyl)propyl]-2(1H)-pyrazinone and 5,7-dichloroindoline as the starting materials. mp 152–154° C.; $^1$H NMR (300 MHz, CDCl$_3$): δ 7.18 (d, J=1.9 Hz, 1 H), 7.12 (s, 1 H), 7.10 (d, J=1.8 Hz, 1 H), 4.93–4.89 (m, 1 H), 4.33 (t, J=7.9 Hz, 2 H), 3.67 (dd, J=10.6, 5.7 Hz, 1 H), 3.55 (dd, J=10.6, 3.3 Hz, 1 H), 3.35 (s, 3 H), 3.12 (t, J=7.9 Hz, 2 H), 1.92–1.72 (m, 2 H), 0.93 (t, J=7.3 Hz, 3 H); HRMS (ESI) calcd for $C_{17}H_{19}N_3O_2BrCl_2$ (M+H)$^+$: 446.0038; found m/z 446.0050.

Example 532

5-Chloro-3-(5-methoxy-7-methyl-2,3-dihydro-1H-indol-1-yl)-1-[2-methyl-1-(i-methylethyl)propyl)]-2(1H)-pyrazinone

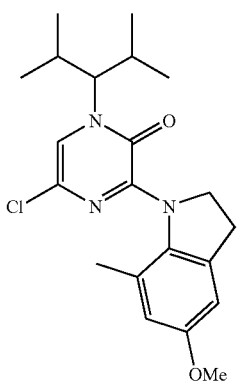

Prepared in a similar fashion as described for Example 413 using 3,5-dichloro-1-(1-isopropyl-2-methylpropyl)-2(1H)-pyrazinone and 5-methoxy-7-methylindoline hydrochloride as the starting materials. mp 94–96° C.; $^1$H NMR (300 MHz, CDCl$_3$): δ 6.70 (s, 1 H), 6.67 (s, 1 H), 6.59 (d, J=2.2 Hz, 1 H), 4.73 (t, J=7.7 Hz, 1 H), 4.35 (t, J=7.9 Hz, 2 H), 3.79 (s, 3 H), 3.05 (t, J=7.7 Hz, 2 H), 2.22–2.14 (m, 2 H), 2.05 (s, 3 H), 1.00 (d, J=7.0 Hz, 6 H), 0.90 (d, J=7.0 Hz, 6 H); HRMS (ESI) calcd for $C_{21}H_{29}N_3O_2Cl$ (M+H)$^+$: 390.1948; found m/z 390.1958.

Example 533

3-(7-Bromo-5-methoxy-2,3-dihydro-1H-indol-1-yl)-5-chloro-1-[2-(methylthio)ethyl]-2(1H)-pyrazinone

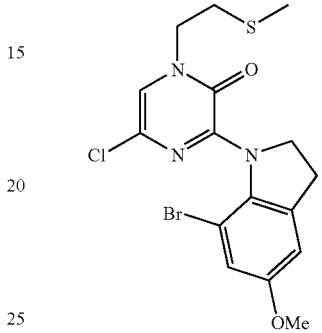

Prepared in a similar fashion as described for Example 413 using 3,5-dichloro-1-[2-(methylthio)ethyl]-2(1H)-pyrazinone and 7-bromo-5-methoxyindoline hydrochloride as the starting materials. $^1$H NMR (300 MHz, CDCl$_3$): δ 6.93 (d, J=2.5 Hz, 1 H), 6.88 (s, 1 H), 6.79 (d, J=2.5 Hz, 1 H), 4.36 (t, J=7.7 Hz, 2 H), 4.05 (t, J=7.0 Hz, 2 H), 3.78 (s, 3 H), 3.10 (t, J=7.5 Hz, 2 H), 2.90 (t, J=7.0 Hz, 2 H), 2.17 (s, 3 H); HRMS (CI) calcd for $C_{16}H_{17}N_3O_2SBrCl$ (M+): 428.9913; found m/z 428.9899.

Example 534

5-Chloro-3-(5-methoxy-7-methyl-2,3-dihydro-1H-indol-1-yl)-1-[2-(methylthio)ethyl]-2(1H)-pyrazinone

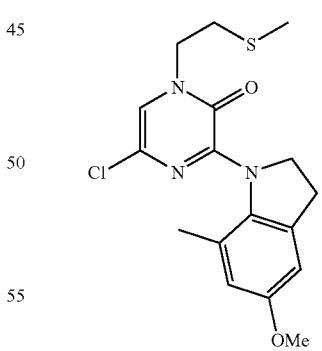

Prepared in a similar fashion as described for Example 413 using 3,5-dichloro-1-[2-(methylthio)ethyl]-2(1H)-pyrazinone and 5-methoxy-7-methylindoline hydrochloride as the starting materials. mp 111–113° C.; $^1$H NMR (300 MHz, CDCl$_3$): δ 6.80 (s, 1 H), 6.68 (d, J=2.2 Hz, 1 H), 6.59 (d, J=2.2 Hz, 1 H), 4.40 (t, J=7.7 Hz, 2 H), 4.04 (t, J=7.1 Hz, 2 H), 3.79 (s, 3 H), 3.04 (t, J=7.7 Hz, 2 H), 2.89 (t, J=7.2 Hz, 2 H), 2.18 (s, 3 H), 2.06 (s, 3 H); HRMS (CI) calcd for $C_{17}H_{20}N_3O_2SCl$ (M+): 365.0965; found m/z 365.0967.

Example 535

5-Chloro-3-(5,7-dichloro-2,3-dihydro-1H-indol-1-yl)-1-[2-(methylthio)ethyl]-2(1H)-pyrazinone

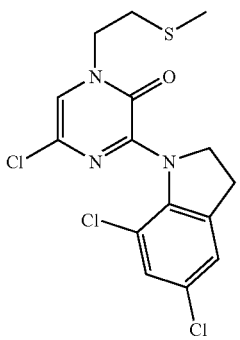

Prepared in a similar fashion as described for Example 413 using 3,5-dichloro-1-[2-(methylthio)ethyl]-2(1H)-pyrazinone and 5,7-dichloroindoline as the starting materials. mp 127–128° C.; $^1$H NMR (300 MHz, CDCl$_3$): 7.19 (d, J=1.8 Hz, 1 H), 7.12 (d, J=2.2 Hz, 1 H), 6.93 (s, 1 H), 4.36 (t, J=8.1 Hz, 2 H), 4.06 (t, J=7.0 Hz, 2 H), 3.13 (t, J=7.9 Hz, 2 H), 2.89 (t, J=7.0 Hz, 2 H), 2.16 (s, 3 H); HRMS (CI) calcd for C$_{15}$H$_{14}$N$_3$OSCl$_3$ (M+): 388.9923; found m/z 388.9920.

Example 536

5-Chloro-3-(7-chloro-5-methoxy-2,3-dihydro-1H-indol-1-yl)-1-(1-ethylpropyl)-6-methyl-2(1H)-pyrazinone

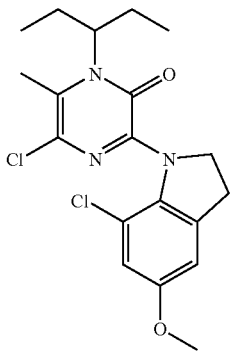

Part A: A solution of 1-ethylpropylamine (1.97 g, 22.6 mmol) in acetonitrile (50 mL) was treated with K$_2$CO$_3$ (9.3 g, 67.7 mmol) 2-bromopropionitrile (3.0 g, 22.6 mmol) and KI (4.13 g, 24.9 mmol). The mixture was heated at 55° C. for 20 h. The mixture was cooled to room temperature and was filtered through a pad of Celite. The filtrate was concentrated and the residue was purified by column chromatography on silica gel (2% MeOH in CH$_2$Cl$_2$) to afford 2-(1-ethylpropylamino)-propionitrile (1.04 g, 36% yield) as a yellow oil.

Part B: A solution of 2-(1-ethylpropylamino)-propionitrile (1.0 g, 7.92 mmol) from Part A in toluene (36 mL) was treated with oxalyl chloride (4.1 mL, 47.5 mmol) and the reaction mixture was heated at 50° C. for 20 h. The reaction mixture was cooled to room temperature and concentrated. The residue was purified by column chromatography on silica gel (10% EtOAc in hexanes→20% EtOAc in hexanes) to afford 3,5-dichloro-1-(1-ethylpropyl)-6-methyl-2(1H)-pyrazinone (696 mg, 35% yield) as a yellow amorphous solid: $^1$H NMR (CDCl$_3$) δ 4.11–4.01 (m, 1H), 2.50 (s, 3H), 2.45–2.35 (m, 2H), 1.98–1.82 (m, 2H), 0.84 (t, J=7.5 Hz, 6H); LRMS (APCI) m/z 248.9 [(M+H)$^+$, calcd for C$_9$H$_{13}$N$_2$OCl$_2$ 248.1].

Part C: A solution 3,5-dichloro-1-(1-ethylpropyl)-6-methyl-2(1H)-pyrazinone from Part B (80 mg, 0.321 mmol) and 7-chloro-5-methoxyindoline (61.9 mg, 0.337 mmol) in THF (1.6 mL) was cooled to 0° C. and was treated with sodium hexamethyldisilazide (353 μL, 0.353 mmol, 1 M in THF). The reaction mixture was allowed to warm up to room temperature and was stirred overnight. The mixture was transferred to a separatory funnel containing saturated NaHCO$_3$ and the aqueous layer was extracted with EtOAc (3×20 mL). The combined organic layers were washed with brine, dried over MgSO$_4$, filtered and concentrated. The residue was purified by column chromatography on silica gel (10% EtOAc in hexanes→40% EtOAc in hexanes) to provide the target compound (22 mg, 17% yield) as a brown oil: $^1$H NMR (CDCl$_3$) δ 6.72 (s, 2H), 4.27 (t, J=7.88 Hz, 2H), 4.00–3.95 (m, 1H), 3.77 (s, 3H), 3.09 (t, J=7.8 Hz, 2H), 2.48–2.38 (m, 2H), 2.42 (s, 3H), 1.95–1.81 (m, 2H), 0.87 (t, J=7.5 Hz, 6H); HRMS (ESI) m/z 396.1259 [(M+H)$^+$, calcd for C$_{19}$H$_{24}$N$_3$O$_2$Cl$_2$ 396.1246].

Example 537

5-Chloro-3-(7-chloro-5-methoxy-2,3-dihydro-1H-indol-1-yl)-1-(1-cyclobutylpropyl)-6-methyl-2(1H)-pyrazinone

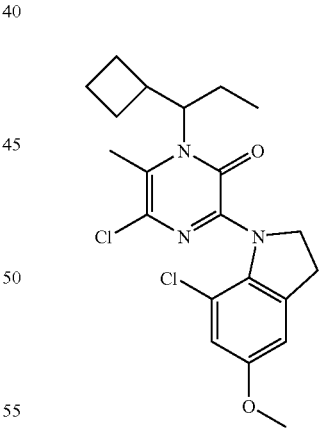

Prepared in a similar fashion as described for Example 536 using 1-(1-cyclobutylpropyl)-3,5-dichloro-6-methyl-2(1H)-pyrazinone and 5-methoxy-7-methylindoline hydrochloride as the starting materials to give a yellow amorphous solid; $^1$H NMR (300 MHz, CDCl$_3$) δ 6.73 (s, 2H), 4.28 (t, J=8.4 Hz, 2H), 4.04–3.97 (m, 1H), 3.79 (s, 3H), 3.62–3.55 (m, 1H), 3.10 (t, J=7.7 Hz, 2H), 2.50 (s, 3H), 2.42–2.35 (m, 1H), 2.22–2.10 (m, 1H), 1.90–1.50 (m, 5H), 1.58–1.50 (m, 1H), 0.86 (t, J=7.3 Hz, 3H); HRMS (ESI) m/z 422.1420 [(M+H)$^+$, calcd for C$_{21}$H$_{26}$N$_3$O$_2$Cl$_2$ 422.1402].

Example 538

3-(5-Bromo-7-chloro-2,3-dihydro-1H-indol-1-yl)-5-chloro-1-methylpropyl-2(1H)-pyrazinone

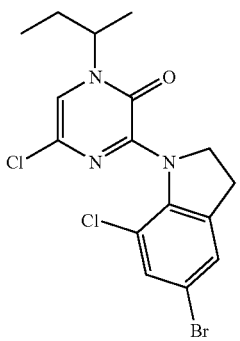

Prepared in a similar fashion as described for Example 413 using 3,5-dichloro-1-methylpropyl-2(1H)-pyrazinone and 5-bromo-7-chloroindoline as the starting materials. mp 150° C.; $^1$H NMR (300 MHz, CDCl$_3$): δ 7.32 (d, J=1.8 Hz, 1 H), 7.26 (d, J=1.9 Hz, 1 H), 6.85 (s, 1 H), 4.97–4.90 (m, 1 H), 4.34 (t, J=8.1 Hz, 2 H), 3.13 (t, J=7.9 Hz, 2 H), 1.77–1.70 (m, 2 H), 1.36 (d, J=7.0 Hz, 3 H), 0.91 (t, J=7.3 Hz, 3 H); HRMS (ESI) calcd for C$_{16}$H$_{17}$N$_3$OBrCl$_2$ (M+H)$^+$: 415.9932; Found m/z 415.9943.

Example 539

3-(5,7-Dichloro-2,3-dihydro-1H-indol-1-yl)-5-ethyl-1-(1-ethylpropyl)-2(1H)-pyrazinone

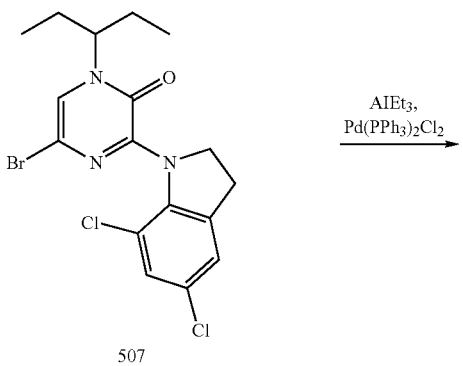

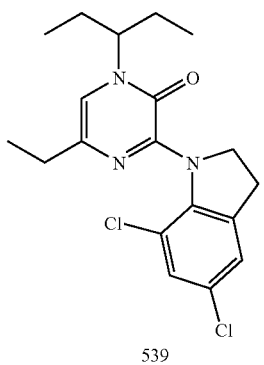

Prepared in a similar fashion as described for XXXII (Example 481, part B) using 5-bromo-3-(5,7-dichloro-2,3-dihydro-1H-indol-1-yl)-1-(1-ethylpropyl)-2(1H)-pyrazinone (Example 507) as the starting material and triethylaluminum in place of trimethylaluminum. mp 136–137° C.; $^1$H NMR (300 MHz, CDCl$_3$): δ 7.14 (d, J=1.8 Hz, 1 H), 7.09 (d, J=1.8 Hz, 1 H), 6.54 (s, 1 H), 4.90–4.79 (m, 1 H), 4.30 (t, J=8.1 Hz, 2 H), 3.14 (t, J=8.1 Hz, 2 H), 2.44 (q, J=7.4 Hz, 2 H), 1.84–1.69 (m, 2 H), 1.67–1.61 (m, 2 H), 1.18 (t, J=7.5 Hz, 3 H), 0.86 (t, J=7.3 Hz, 6H); HRMS (ESI) calcd for C$_{19}$H$_{24}$N$_3$OCl$_2$ (M+H)$^+$: 380.1296; Found m/z 380.1280.

Example 540

3-(5-Bromo-7-chloro-2,3-dihydro-1H-indol-1-yl)-5-chloro-1-(1-ethylpropyl)-2(1H)-pyrazinone

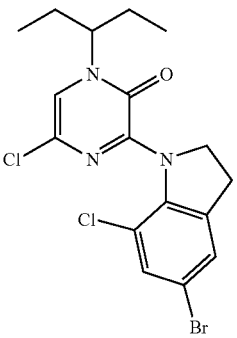

Prepared in a similar fashion as described for Example 413 using 3,5-dichloro-1-(1-ethylpropyl)-2(1H)-pyrazinone and 5-bromo-7-chloroindoline as the starting materials. mp 156–157° C.; $^1$H NMR (300 MHz, CDCl$_3$): δ 7.25 (d, J=1.8 Hz, 1 H), 7.19 (d, J=2.9 Hz, 1 H), 6.71 (s, 1 H), 4.75–4.69 (m, 1 H), 4.27 (t, J=7.9 Hz, 2 H), 3.07 (t, J=8.1 Hz, 2 H), 1.78–1.51 (m, 4 H), 0.81 (t, J=7.3 Hz, 6 H); HRMS (ESI) calcd for C$_{17}$H$_{19}$N$_3$OBrCl$_2$ (M+H)$^+$: 430.0089; Found m/z 430.0106.

Example 541

6-(5,7-Dichloro-2,3-dihydro-1H-indol-1-yl)-4-(1-ethylpropyl)-4,5-dihydro-5-oxo-2-pyrazinecarbonitrile

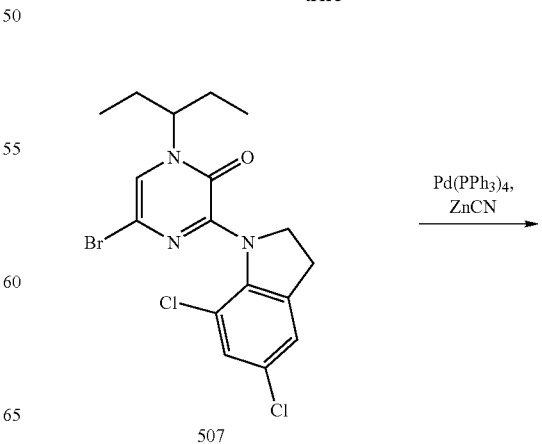

-continued

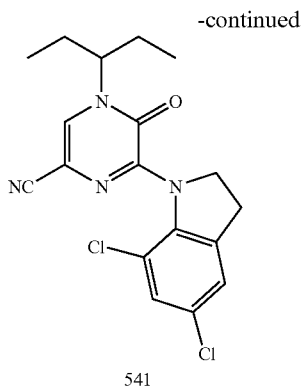

541

A solution of 5-bromo-3-(5,7-dichloro-2,3-dihydro-1H-indol-1-yl)-1-(1-ethylpropyl)-2(1H)-pyrazinone (Example 507) (100 mg, 0.23 mmol), zinc cyanide (32 mg, 0.28 mmol), and tetrakis(triphenylphosphine)palladium(0) (32 mg, 25 μmol) in dimethylforamide (3 ml) was degassed with nitrogen and heated to 175° C. in a microwave for 5 min. The reaction mixture was diluted with water (5 mL) and extracted with ethyl acetate (5 mL×2). The combined organic extracts were dried (MgSO4), filtered, and concentrated in vacuo to give a crude residue. Purification by HPLC (reverse phase C18, 95% water in acetonitrile containing 0.1% trifluroacetic acid to 5% water in acetonitrile containing 0.1% trifluroacetic acid, flow rate 18 ml/min, retention time 38.4 min) gave the product (18 mg, 21%) as a yellow solid. mp 197–199° C.; $^1$H NMR (300 MHz, CDCl$_3$): δ 7.27 (s, 1 H), 7.19 (d, J=2.2 Hz, 1 H), 7.14 (d, J=1.8 Hz, 1 H), 4.82–4.77 (m, 1 H), 4.33 (t, J=7.9 Hz, 2 H), 3.15 (t, J=7.7 Hz, 2 H), 1.92–1.78 (m, 2 H), 1.75–1.60 (m, 2 H), 0.89 (t, J=7.3 Hz, 6 H); HRMS (ESI) calcd for $C_{18}H_{19}N_4OCl_2$ (M+H)$^+$: 377.0936; Found m/z 377.0910.

Example 542

3-(5-Bromo-7-chloro-2,3-dihydro-1H-indol-1-yl)-5-chloro-1-[(1R)-1-cyclopropylpropyl]-2(1H)-pyrazinone

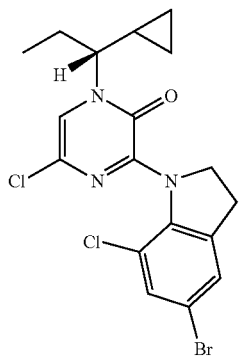

Prepared in a similar fashion as described for Example 413 using 1-[(1R)-1-cyclopropylpropyl]-3,5-dichloro-2(1H)-pyrazinone and 5-bromo-7-chloroindoline as the starting materials. mp 154–156° C.; $^1$H NMR (300 MHz, CDCl$_3$) δ 7.31 (d, J=1.9 Hz, 1 H), 7.24 (d, J=1.8 Hz, 1 H), 7.01 (s, 1 H), 4.32 (t, J=8.1 Hz, 2 H), 4.05 (app. q, J=8.2 Hz, 1 H), 3.14 (t, J=7.9 Hz, 2 H), 1.96–1.83 (m, 2 H), 1.07–1.00 (m, 1 H), 0.94 (t, J=7.3 Hz, 3 H), 0.81–0.75 (m, 1 H), 0.55–0.48 (m, 2 H), 0.35–0.28 (m, 1 H); HRMS (ESI) calcd for $C_{18}H_{19}N_3OBrCl_2$ (M+H)$^+$: 442.0089; Found m/z 442.0102.

Example 543

3-(5-Bromo-7-chloro-2,3-dihydro-1H-indol-1-yl)-5-chloro-1-[(1S)-1-cyclopropylpropyl]-2(1H)-pyrazinone

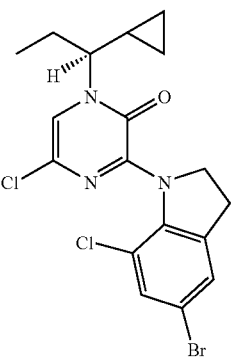

Prepared in a similar fashion as described for Example 413 using 1-[(1S)-1-cyclopropylpropyl]-3,5-dichloro-2(1H)-pyrazinone and 5-bromo-7-chloroindoline as the starting materials. mp 126–127° C.; $^1$H NMR (300 MHz, CDCl$_3$): δ 7.31 (d, J=1.9 Hz, 1 H), 7.24 (d, J=1.4 Hz, 1 H), 7.01 (s, 1 H), 4.32 (t, J=7.9 Hz, 2 H), 4.08–4.02 (m, 1 H), 3.14 (t, J=8.1 Hz, 2 H), 1.94–1.78 (m, 2 H), 1.05–1.00 (m, 1 H), 0.94 (t, J=7.3 Hz, 3 H), 0.81–0.77 (m, 1 H), 0.54–0.48 (m, 2 H), 0.34–0.30 (m, 1 H); HRMS (ESI) calcd for $C_{18}H_{19}N_3OBrCl_2$ (M+H)$^+$: 442.0089; Found m/z 442.0093.

Example 544

5-Chloro-3-(7-chloro-5-methoxy-2,3-dihydro-1H-indol-1-yl)-1-[(1R)-1-(methoxymethyl)propyl]-2(1H)-pyrazinone

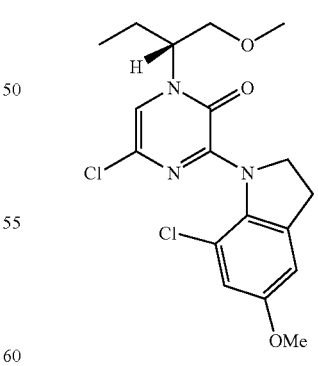

Prepared in a similar fashion as described for Example 413 using 3,5-dichloro-1-[(1R)-1-(methoxymethyl)propyl]-2(1H)-pyrazinone and 7-chloro-5-methoxyindoline hydrochloride as the starting materials. mp 126–128° C.; $^1$H NMR (300 MHz, CDCl$_3$): δ 6.99 (s, 1 H), 6.74 (s, 2 H), 5.00–4.90 (m, 1 H), 4.35 (t, J=8.0 Hz, 2 H), 3.78 (s, 3 H), 3.67 (dd, J=10.6, 5.5 Hz, 1 H), 3.56 (dd, J=10.6, 3.7 Hz, 1 H), 3.35 (s, 3 H), 3.09 (t, J=7.7 Hz, 2 H), 1.92–1.72 (m, 2 H), 0.93 (t, J=7.4 Hz, 3 H); HRMS (ESI) calcd for $C_{18}H_{22}N_3O_3Cl_2$ (M+H)$^+$: 398.1038; Found m/z 398.1064.

Example 545

5-Chloro-3-(5-methoxy-7-methyl-2,3-dihydro-1H-indol-1-yl)-1-[(1R)-1-(methoxymethyl)propyl]-2(1H)-pyrazinone

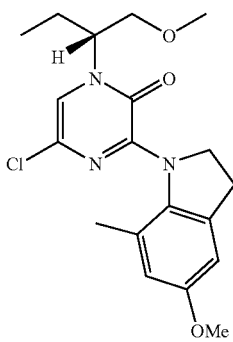

Prepared in a similar fashion as described for Example 413 using 3,5-dichloro-1-[(1R)-1-(methoxymethyl)propyl]-2(1H)-pyrazinone and 5-methoxy-7-methylindoline hydrochloride as the starting materials. mp 62–64° C.; $^1$H NMR (300 MHz, CDCl$_3$): δ 6.92 (s, 1 H), 6.67 (s, 1 H), 6.59 (d, J=2.2 Hz, 1 H), 5.02–4.92 (m, 1 H), 4.38 (t, J=7.7 Hz, 2 H), 3.79 (s, 3 H), 3.66 (dd, J=10.3, 5.5 Hz, 1 H), 3.56 (dd, J=10.6, 3.6 Hz, 1 H), 3.36 (s, 3 H), 3.04 (t, J=7.7 Hz, 2 H), 2.06 (s, 3 H), 1.90–1.70 (m, 2 H), 0.94 (t, J=7.3 Hz, 3 H); HRMS (ESI) calcd for $C_{19}H_{25}N_3O_3Cl$ (M+H)$^+$: 378.1584; Found m/z 378.1604.

Example 546

1-[6-Chloro-4-[(1R)-1-(methoxymethyl)propyl]-3,4-dihydro-3-oxopyrazinyl]-5-methoxy-2,3-dihydro-1H-indole-7-carbonitrile

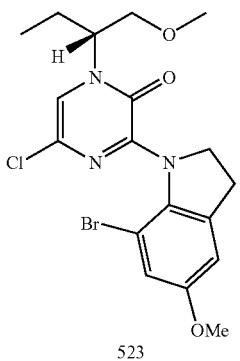
523

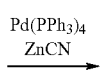
Pd(PPh$_3$)$_4$
ZnCN

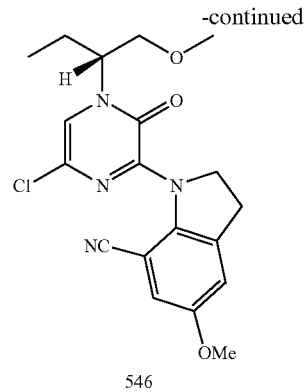
546

Prepared in a similar fashion as described for Example 541 using 3-(7-bromo-5-methoxy-2,3-dihydro-1H-indol-1-yl)-5-chloro-1-[(1R)-1-(methoxymethyl)propyl]-2(1H)-pyrazinone (Example 523) as the starting material. mp 141–142° C.; $^1$H NMR (300 MHz, CDCl$_3$): δ 7.11 (s, 1 H), 6.99 (d, J=2.6 Hz, 1 H), 6.87 (d, J=2.6 Hz, 1 H), 5.00–4.90 (m, 1 H), 4.41 (t, J=8.1 Hz, 2 H), 3.79 (s, 3 H), 3.68 (dd, J=10.7, 5.2 Hz, 1 H), 3.59 (dd, J=10.6, 3.3 Hz, 1 H), 3.35 (s, 3 H), 3.11 (t, J=8.1 Hz, 2 H), 1.95–1.75 (m, 2 H), 0.95 (t, J=7.3 Hz, 3 H); HRMS (CI) calcd for $C_{19}H_{21}N_4O_3Cl$ (M+H)$^+$: 388.1302; Found m/z 388.1298.

Example 547

5-Bromo-3-(5-bromo-7-chloro-2,3-dihydro-1H-indol-1-yl)-1-[(1R)-1-(methoxymethyl)propyl]-2(1H)-pyrazinone

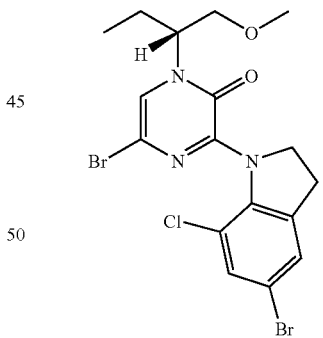

Prepared in a similar fashion as described for Example 413 using 3,5-dibromo-1-[(1R)-1-(methoxymethyl)propyl]-2(1H)-pyrazinone and 5-bromo-7-chloroindoline as the starting materials. mp 118° C.; $^1$H NMR (300 MHz, CDCl$_3$): δ 7.31 (s, 1 H), 7.24 (s, 1 H), 7.13 (s, 1 H), 4.98–4.90 (m, 1 H), 4.32 (t, J=7.9 Hz, 2 H), 3.66 (dd, J=10.7, 5.9 Hz, 1 H), 3.55 (dd, J=10.6, 3.3 Hz, 1 H), 3.35 (s, 3 H), 3.13 (t, J=7.9 Hz, 2 H), 1.85–1.74 (m, 2 H), 0.93 (t, J=7.3 Hz, 3 H); HRMS (ESI) calcd for $C_{17}H_{19}N_3O_2Br_2Cl$ (M+H)$^+$: 489.0543; Found m/z 489.9534.

Example 548

3-(5-Bromo-7-chloro-2,3-dihydro-1H-indol-1-yl)-5-chloro-1-[(1S)-1-(methoxymethyl)propyl]-2(1H)-pyrazinone

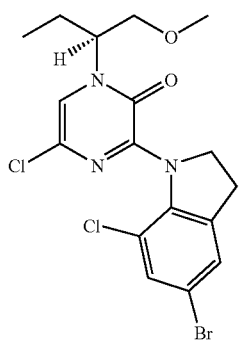

Prepared in a similar fashion as described for Example 413 using 3,5-dichloro-1-[(1S)-1-(methoxymethyl)propyl]-2(1H)-pyrazinone and 5-bromo-7-chloroindoline as the starting materials. mp 121–122° C.; $^1$H NMR (300 MHz, CDCl$_3$): δ 7.24 (s, 1 H), 7.18 (s, 1 H), 6.99 (s, 1 H), 4.90–4.80 (m, 1 H), 4.26 (t, J=8.1 Hz, 2 H), 3.60 (dd, J=10.2, 5.5 Hz, 1 H), 3.49 (dd, J=10.6, 3.3 Hz, 1 H), 3.28 (s, 3 H), 3.06 (t, J=8.1 Hz, 2 H), 1.83–1.65 (m, 2 H), 0.86 (t, J=7.4 Hz, 3 H); HRMS (ESI) calcd for C$_{17}$H$_{19}$N$_3$O$_2$BrCl$_2$ (M+H)$^+$: 446.0038; Found m/z 446.0048.

Example 549

5-Bromo-3-(5-methoxy-7-methyl-2,3-dihydro-1H-indol-1-yl)-1-[(1S)-1-(methoxymethyl)propyl]-2(1H)-pyrazinone

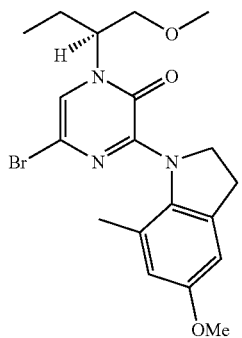

Prepared in a similar fashion as described for Example 413 using 3,5-dibromo-1-[(1S)-1-(methoxymethyl)propyl]-2(1H)-pyrazinone and 5-methoxy-7-methylindoline hydrochloride as the starting materials. mp 115–117° C.; $^1$H NMR (300 MHz, CDCl$_3$): δ 6.98 (s, 1 H), 6.66 (m, 1 H), 6.58 (d, J=2.2 Hz, 1 H), 5.00–4.90 (m, 1 H), 4.38 (t, J=8.1 Hz, 2 H), 3.79 (s, 3 H), 3.66 (dd, J=10.2, 5.5 Hz, 1 H), 3.56 (dd, J=10.6, 3.7 Hz, 1 H), 3.36 (s, 3 H), 3.04 (t, J=7.7 Hz, 2 H), 2.06 (s, 3 H), 1.92–1.70 (m, 2 H), 0.94 (t, J=7.4 Hz, 3 H); HRMS (ESI) calcd for C$_{19}$H$_{25}$N$_3$O$_3$Br (M+H)$^+$: 422.1079; Found m/z 422.1096.

Example 550

3-(8-Bromo-6-methoxy-1,2,3,4-tetrahydroquinoline)-5-chloro-1-(1-ethylpropyl)-2(1H)-pyrazinone

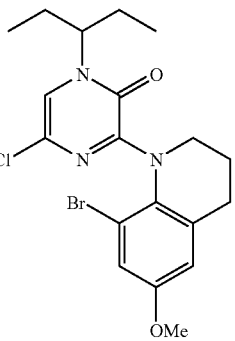

Part A: A solution of 6-methoxy-1,2,3,4-tetrahydroquinoline (6.19 g, 37.9 mmol) in CH$_2$Cl$_2$ (76 mL) was treated with pyridinium tribromide (25.42 g, 79.7 mmol). The reaction mixture was stirred at room temperature for 2 h. The reaction was quenched with sat NaHSO$_3$ (50 mL) and water (50 mL). The dichloromethane was separated, dried (Na$_2$SO$_4$) and concentrated. The residue was chromatographed on silica gel using 20% ethyl acetate/hexanes as eluent to give 8-bromo-6-methoxy-1,2,3,4-tetrahydroquinoline (2.93 g, 32% yield): $^1$H NMR (300 MHz, CDCl$_3$): δ 6.88 (s 1 H), 6.55 (s, 1 H), 3.71 (s, 3 H), 3.37–3.33 (t, J=6.6, 2 H), 2.78–2.74 (t, 2 H), 1.97–1.89 (m, 2 H); LRMS (AP+) for (M+H)$^+$: for C$_{10}$H$_{12}$NOBr Calculated: 241.1 found : 241.0.

Part B: Prepared in a similar fashion as described for Example 413 using 3,5-dichloro-1-(1-ethylpropyl)-2(1H)-pyrazinone and 8-bromo-6-methoxy-1,2,3,4-tetrahydroquinoline as the starting materials. mp 125–126° C.; HRMS (ESI) calcd for C$_{19}$H$_{24}$N$_3$O$_2$BrCl (M+H)$^+$: 440.0740; Found m/z 440.0750.

Example 551

3-(8-Bromo-6-methoxy-1,2,3,4-tetrahydroquinoline)-5-chloro-1-[(1R)-1-cyclopropylpropyl]-2(1H)-pyrazinone

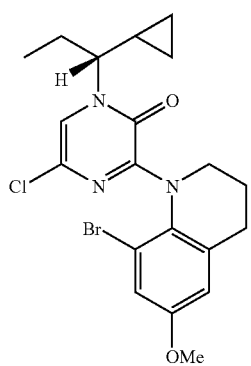

Prepared in a similar fashion as described for Example 413 using 3,5-dichloro-1-[(1R)-1-cyclopropylpropyl]-2(1H)-pyrazinone and 8-bromo-6-methoxy-1,2,3,4-tetrahydroquinoline as the starting materials. mp 127–129° C.; HRMS (ESI) calcd for $C_{20}H_{24}N_3O_2BrCl$ (M+H)$^+$: 452.0740; Found m/z 452.0766.

Example 552

3-(8-Bromo-6-methoxy-1,2,3,4-tetrahydroquinoline)-5-chloro-1-[(1S)-1-cyclopropylpropyl]-2(1H)-pyrazinone

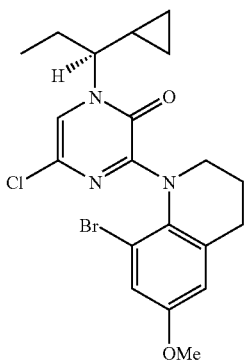

Prepared in a similar fashion as described for Example 413 using 3,5-dichloro-1-[(1S)-1-cyclopropylpropyl]-2(1H)-pyrazinone and 8-bromo-6-methoxy-1,2,3,4-tetrahydroquinoline as the starting materials. mp 118–119° C.; HRMS (ESI) calcd for $C_{20}H_{24}N_3O_2BrCl$ (M+H)$^+$: 452.0740; Found m/z 452.0734.

Example 553

3-(8-Bromo-6-methoxy-1,2,3,4-tetrahydroquinoline)-5-chloro-1-[(1R)-2-methoxy-1-methylethyl]-2(1H)-pyrazinone

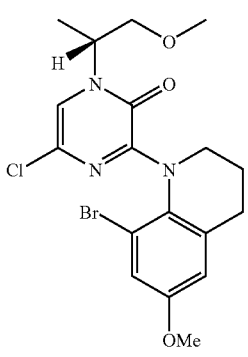

Prepared in a similar fashion as described for Example 413 using 3,5-dichloro-1-[(1R)-2-methoxy-1-methylethyl]-2(1H)-pyrazinone and 8-bromo-6-methoxy-1,2,3,4-tetrahydroquinoline as the starting materials. mp 146° C.; HRMS (ESI) calcd for $C_{18}H_{22}N_3O_3BrCl$ (M+H)$^+$: 442.0533; Found m/z 442.0557.

Example 554

5-Bromo-3-(8-bromo-6-methoxy-1,2,3,4-tetrahydroquinoline)-1-[(1R)-1-(methoxymethyl)propyl]-2(1H)-pyrazinone

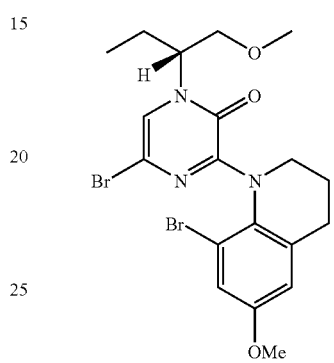

Prepared in a similar fashion as described for Example 413 using 3,5-dibromo-1-[(1R)-1-(methoxymethyl)propyl]-2(1H)-pyrazinone and 8-bromo-6-methoxy-1,2,3,4-tetrahydroquinoline as the starting materials. mp 102–103° C.; HRMS (ESI) calcd for $C_{19}H_{24}N_3O_3Br_2$ (M+H)$^+$: 500.0185; Found m/z 500.0205.

Example 555

3-(8-Bromo-6-methoxy-1,2,3,4-tetrahydroquinoline)-5-chloro-1-[(1S)-1-(methoxymethyl)propyl]-2(1H)-pyrazinone

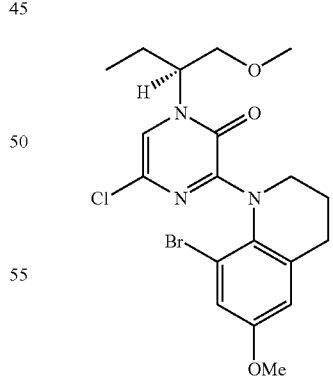

Prepared in a similar fashion as described for Example 413 using 3,5-dichloro-1-[(1S)-1-(methoxymethyl)propyl]-2(1H)-pyrazinone and 8-bromo-6-methoxy-1,2,3,4-tetrahydroquinoline as the starting materials. mp 93–94° C.; HRMS (ESI) calcd for $C_{19}H_{24}N_3O_3BrCl$ (M+H)$^+$: 456.0690; Found m/z 456.0670.

Example 556

3-(5-Bromo-7-methoxy-2,3-dihydro-4H-1,4-benzoxazin-4-yl)-5-chloro-1-[(1R)-1-cyclopropylpropyl]-2(1H)-pyrazinone

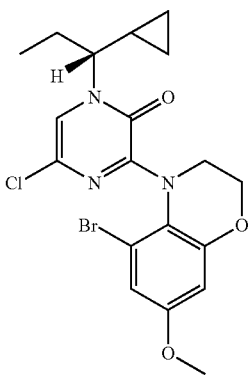

Synthesis of internmediate
5-Bromo-7-methoxy-3,4-dihydro-2H-1,4-benzoxazine

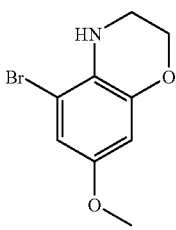

Part A: 5-Fluoro-2-nitrophenol (5.00 g, 31.8 mmol) and methanol (120 mL) were combined and the mixture was treated with sodium methoxide (4.6 mL, 190.8 mmol, 25% w/w solution in MeOH). The reaction mixture was heated at 60° C. for 40 h. The mixture was transferred to a separatory funnel containing cold 1 N HCl and the aqueous layer was extracted with EtOAc (3×). The combined organic layers were washed with brine, dried over MgSO$_4$, filtered and concentrated to afford 5-methoxy-2-nitrophenol (5.0 g, 93% yield) as a yellow solid: mp 93.0–94.0° C., $^1$H NMR (300 MHz, CDCl$_3$): δ 11.05 (s, 1H), 8.03 (d, J=10.3 Hz, 1H), 6.55–6.51 (m, 2H), 3.89 (s, 3H).

Part B: The product from Part A (3.0 g, 17.7 mmol) was dissolved in methanol (120 mL). The reaction vessel was evacuated and flushed with nitrogen and 10% Pd/C (600 mg) was added. The mixture was placed under an H$_2$ atmosphere on the Parr shaker for 1 h. The catalyst was removed by filtration through a pad of Celite and the filtrate was concentrated to give 2-amino-5-methoxyphenol (2.52 g, 100% yield) as a brown solid which was used directly in the next step without further purification: $^1$H NMR (300 MHz, CDCl$_3$): δ 6.78 (d, J=8.4 Hz, 1H), 6.44 (d, J=2.9 Hz, 1H), 6.35 (dd, J=8.4, 2.9 Hz, 1H), 3.73 (s, 3H).

Part C: To a vigorously stirred solution of the product from Part B (12.34 g, 88.69 mmol) in dry acetone (355 mL) was added K$_2$CO$_3$ (9.00 g, 68.70 mmol) followed by the addition of 1,2-dibromoethane (2.50 mL, 28.75 mmol). Three additional portions of K$_2$CO$_3$ (9.00 g, 68.70 mmol) and 1,2-dibromoethane (2.50 mL, 28.75 mmol) were added at 30 min intervals. The reaction mixture was then heated at reflux overnight. The reaction mixture was then cooled to room temperature and filtered through a pad of Celite. The filtrate was concentrated and purified by column chromatography on silica gel (10% EtOAc. 40% EtOAc in hexanes) to furnish 7-methoxy-3,4-dihydro-2H-1,4-benzoxazine (4.60 g, 31% yield) as a yellow oil and recovered starting material (2.5 g, 20% recovery): $^1$H NMR (300 MHz, CDCl$_3$): δ 6.55 (d, J=8.5 Hz, 1H), 6.42–6.35 (m, 2H), 4.25–4.21 (m, 2H), 3.72 (s, 3H), 3.38–3.35 (m, 2H); LRMS (APCI) m/z 166.0 [(M+H)$^+$, calcd for C$_9$H$_{12}$NO$_2$ 166.2].

Part D: A mixture of the product from Part C (4.60 g, 27.85 mmol) and pyridinium tribromide (9.80 g, 30.63 mmol) in CH$_2$Cl$_2$ (280 mL) was stirred at room temperature for 6.5 h. The reaction mixture was quenched with saturated aqueous Na$_2$SO$_3$. The aqueous layer was extracted with CH$_2$Cl$_2$ (3×). The combined organic layers were washed with H$_2$O, brine, dried over MgSO$_4$, filtered and concentrated. The residue was purified by column chromatography on silica gel (10% EtOAc. 30% EtOAc in hexanes) to afford 5-bromo-7-methoxy-3,4-dihydro-2H-1,4-benzoxazine (1.34 g, 20% yield) as a pale yellow oil: $^1$H NMR (300 MHz, CDCl$_3$): δ 6.65 (d, J=3.0 Hz, 1H), 6.40 (d, J=2.9 Hz, 1H), 4.25–4.22 (m, 2H), 3.71 (s, 3H), 3.46–3.42 (m, 2H).

Synthesis of Example 556

3,5-dichloro-1-[(1R)-1-cyclopropylpropyl]-2(1H)-pyrazinone (67.9 mg, 0.275 mmol) and 5-bromo-7-methoxy-3,4-dihydro-2H-1,4-benzoxazine (67 mg, 0.275 mmol) were combined in THF (1.4 mL). The mixture was cooled to 0° C. and was treated with NaHMDS (302 μL, 0.302 mmol, 1 M in THF). The cooling bath was removed and the reaction mixture was stirred at room temperature overnight. The reaction mixture was poured into a separatory funnel containing saturated NaHCO$_3$ and the aqueous layer was extracted with EtOAc (3×20 mL). The combined organic layers were washed with brine, dried over MgSO$_4$, filtered and concentrated. The crude product was purified by column chromatography on silica gel (10% EtOAc→30% EtOAc in hexanes) to afford a brown oil. $^1$H NMR (300 MHz, CDCl$_3$): δ 6.73 (d, J=1.5 Hz, 1H), 6.70 (s, 1H), 6.45 (d, J=1.3 Hz, 1H), 4.31–4.00 (m, 5H), 3.75 (s, 3H), 1.89–1.74 (m, 2H), 1.05–1.02 (m, 1H), 0.93 (t, J=7.3 Hz, 3H), 0.90–0.75 (m, 1H), 0.52–0.49 (m, 2H), 0.35–0.25 (m, 1H); HRMS (ESI) m/z 453.0459 [M+, calcd for C$_{19}$H$_{21}$N$_3$O$_3$BrCl 453.0455].

Example 557

5-Chloro-3-(7-chloro-5-methoxy-2,3-dihydro-1H-indol-1-yl)-1-(1-cyclobutylpropyl)-2(1H)-pyrazinone

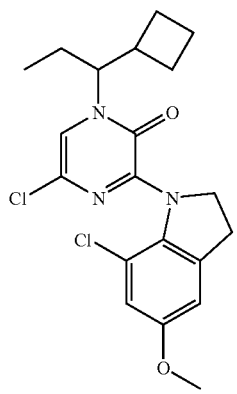

Prepared in a similar fashion as described for Example 413 using 3,5-dichloro-1-(1-cyclobutylpropyl)-2(1H)-pyrazinone and 7-chloro-5-methoxyindoline hydrochloride as the starting materials to give a yellow oil. $^1$H NMR (300

MHz, CDCl$_3$): δ 6.74 (s, 2H), 6.67 (s, 1H), 4.90–4.80 (m, 1H), 4.34 (t, J=7.9 Hz, 2H), 3.78 (s, 3H), 3.10 (t, J=7.7 Hz, 2H), 2.60–2.50 (m, 1H), 2.18–2.12 (m, 1H), 1.90–1.70 (m, 6H), 1.55–1.43 (m, 1H), 0.84 (t, J=7.5 Hz, 3H); HRMS (ESI) m/z 408.1270 [(M+H)$^+$, calcd for C$_{20}$H$_{24}$N$_3$O$_2$Cl$_2$ 408.1246].

Example 558

3-(5-Bromo-7-methoxy-2,3-dihydro-4H-1,4-benzoxazin-4-yl)-5-chloro-1-(1-cyclobutylpropyl)-2(1H)-pyrazinone

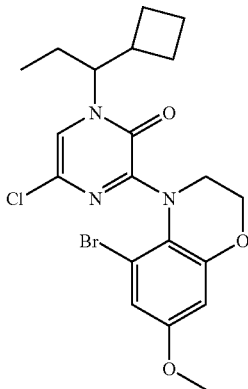

Prepared in a similar fashion as described for Example 556 using 3,5-dichloro-1-(1-cyclobutylpropyl)-2(1H)-pyrazinone and 5-bromo-7-methoxy-3,4-dihydro-2H-1,4-benzoxazine as the starting materials to give a brown oil. $^1$H NMR (300 MHz, CDCl$_3$): δ 6.73 (d, J=2.9 Hz, 1H), 6.72 (s, 1H), 6.45 (d, J=2.6 Hz, 1H), 4.90–4.85 (m, 1H), 4.50–3.88 (m, 4H), 3.76 (s, 3H), 2.58–2.50 (m, 1H), 2.18–2.13 (m, 1H), 1.85–1.65 (m, 6H), 1.50–1.40 (m, 1H), 0.83 (t, J=7.4 Hz, 3H), HRMS (ESI) m/z 468.0665 [M+, calcd for C$_{20}$H$_{24}$N$_3$O$_3$BrCl 468.0690].

Example 559

3-(5-Bromo-7-methoxy-2,3-dihydro-4H-1,4-benzoxazin-4-yl)-5-chloro-1-(1-cyclobutylpropyl)-2(1H)-pyrazinone

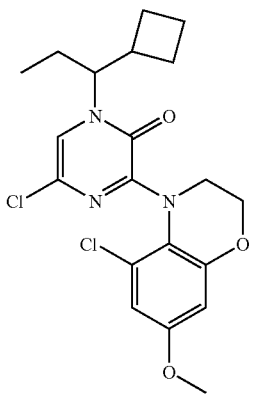

Prepared in a similar fashion as described for Example 556 using 3,5-dichloro-1-(1-cyclobutylpropyl)-2(1H)-pyrazinone and 5-chloro-7-methoxy-3,4-dihydro-2H-1,4-benzoxazine as the starting materials to give a yellow oil. $^1$H NMR (300 MHz, CDCl$_3$): δ 6.70 (s, 1H), 6.55 (d, J=2.9 Hz, 1H), 6.41 (d, J=2.6 Hz, 1H), 4.88 (s br, 1H), 4.40–4.00 (m, 4H), 3.76 (s, 3H), 2.60–2.45 (m, 1H), 2.18–2.12 (m, 1H), 1.96–1.60 (m, 6H), 1.56–1.36 (m, 1H), 0.83 (t, J=7.6 Hz, 3H); HRMS (ESI) m/z 424.1199 [(M+H)$^+$, calcd for C$_{20}$H$_{24}$N$_3$O$_3$Cl$_2$ 424.1195].

Example 560

3-(5-Bromo-7-methoxy-2,3-dihydro-4H-1,4-benzoxazin-4-yl)-5-chloro-1-[(1S)-1-cyclopropylpropyl]-2(1H)-pyrazinone

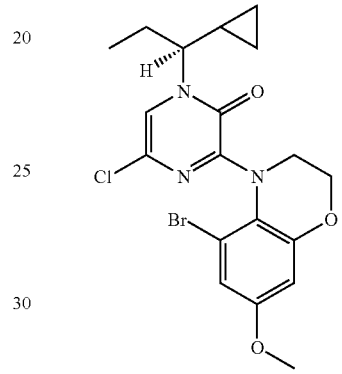

Prepared in a similar fashion as described for Example 556 using 3,5-dichloro-1-[(1S)-1-cyclopropylpropyl]-2 (1H)-pyrazinone and 5-bromo-7-methoxy-3,4-dihydro-2H-1,4-benzoxazine as the starting materials to give an oil. $^1$H NMR (300 MHz, CDCl$_3$): δ 7.03 (s, 1H), 6.73 (d, J=2.9 Hz, 1H), 6.45 (d, J=2.9 Hz, 1H), 4.44–3.89 (m, 5H), 3.75 (s, 3H), 1.96–1.70 (m, 2H), 1.12–1.00 (m, 1H), 0.92 (t, J=7.3 Hz, 3H), 0.92 (t, J=7.3 Hz, 3H), 0.84–0.72 (m, 1H), 0.56–0.44 (m, 2H), 0.35–0.25 (m, 1H); HRMS (ESI) m/z 454.0518 [(M+H)$^+$, calcd for C$_{19}$H$_{22}$N$_3$O$_3$BrCl 454.0533].

Example 561

3-(5-Bromo-7-methoxy-2,3-dihydro-4H-1,4-benzoxazin-4-yl)-5-chloro-1-[(1R)-(1-methoxymethyl)propyl]-2(1H)-pyrazinone

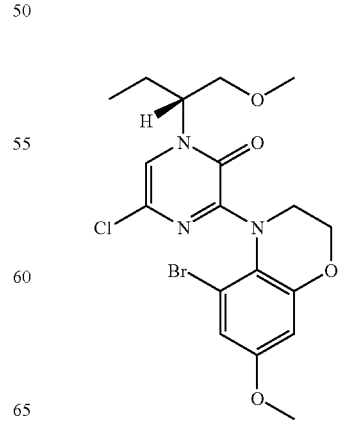

Prepared in a similar fashion as described for Example 556 using 3,5-dichloro-1-[(1R)-1-(methoxymethyl)propyl]-2(1H)-pyrazinone and 5-bromo-7-methoxy-3,4-dihydro-2H-1,4-benzoxazine as the starting materials to give an oil. $^1$H NMR (300 MHz, CDCl$_3$): δ 7.05 (s, 1H), 6.73 (d, J=2.5 Hz, 1H), 6.45 (d, J=2.5 Hz, 1H), 5.09–4.86 (m, 1H), 4.50–3.84 (m, 4H), 3.76 (s, 3H), 3.70–3.52 (m, 2H), 3.34 (s, 3H), 1.92–0.76 (m, 5H); HRMS (ESI) m/z 457.0410 [M+, calcd for C$_{18}$H$_{21}$N$_3$O$_4$BrCl 457.0404].

Example 562

3-(5-Bromo-7-methoxy-2,3-dihydro-4H-1,4-benzoxazin-4-yl)-5-chloro-1-[(1S)-(1-methoxymethyl)propyl]-2(1H)-pyrazinone

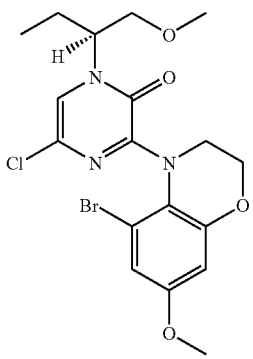

Prepared in a similar fashion as described for Example 556 using 3,5-dichloro-1-[(1S)-1-(methoxymethyl)propyl]-2(1H)-pyrazinone and 5-bromo-7-methoxy-3,4-dihydro-2H-1,4-benzoxazine as the starting materials to give an oil. $^1$H NMR (300 MHz, CDCl$_3$): δ 7.05 (s, 1H), 6.73 (d, J=2.9 Hz, 1H), 6.45 (d, J=2.9 Hz, 1H), 5.08–4.86 (m, 1H), 4.52–3.84 (m, 4H), 3.76 (m, 3H), 3.68–3.52 (m, 2H), 3.34 (m, 3H), 2.00–0.80 (m, 5H); HRMS (ESI) m/z 458.0457 [(M+H)$^+$, calcd for C$_{18}$H$_{22}$N$_3$O$_4$BrCl 458.0482].

Example 563

3-(5-Bromo-7-methoxy-2,3-dihydro-4H-1,4-benzoxazin-4-yl)-5-chloro-1-[(1S)-2-methoxy-1-methylethyl]-2(1H)-pyrazinone

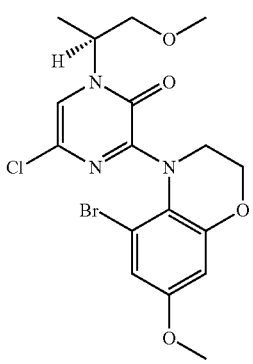

Prepared in a similar fashion as described for Example 556 using 3,5-dichloro-1-[(1S)-2-methoxy-1-methylethyl]-2 (1H)-pyrazinone and 5-bromo-7-methoxy-3,4-dihydro-2H-1,4-benzoxazine as the starting materials to give an oil. $^1$H NMR (300 MHz, CDCl$_3$): δ 7.06 (s, 1H), 6.74 (d, J=3.0 Hz, 1H), 6.45 (d, J=2.5 Hz, 1H), 5.24–5.10 (m, 1H), 4.52–3.86 (m, 4H), 3.76 (s, 3H), 3.57 (d, J=3.7 Hz, 2H), 3.35 (s, 3H), 1.41 (d, J=6.9 Hz, 3H); HRMS (ESI) m/z 444.0339 [(M+H)$^+$, calcd for C$_{17}$H$_{20}$N$_3$O$_4$BrCl 444.0326].

Example 564

5-chloro-1-(1-cyclobutylpropyl)-3-(7-methoxy-2,3-dihydro-4H-1,4-benzoxazin-4-yl)-2(1H)-pyrazinone

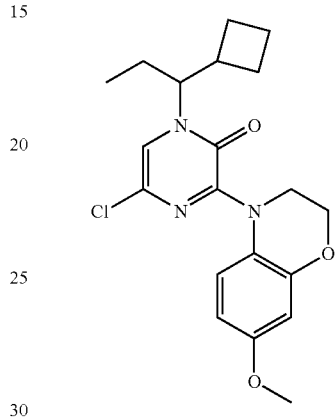

Prepared in a similar fashion as described for Example aaa using 3,5-dichloro-1-(1-cyclobutylpropyl)-2(1H)-pyrazinone and 7-methoxy-3,4-dihydro-2H-1,4-benzoxazine as the starting materials to give an oil. $^1$H NMR (300 MHz, CDCl$_3$) δ 6.91 (d, J=9.5 Hz, 1H), 6.69 (s, 1H), 6.46–6.41 (m, 2H), 4.92–4.82 (m, 1H), 4.34–4.31 (m, 2H), 4.20–4.16 (m, 2H), 3.76 (s, 3H), 2.64–2.50 (m, 1H), 2.24–2.12 (m, 1H), 1.96–1.40 (m, 7H), 0.84 (t, J=7.5 Hz, 3H); HRMS (ESI) m/z 390.1595 [(M+H)$^+$, calcd for C$_{20}$H$_{25}$N$_3$O$_3$Cl 390.1584].

Example 565

5-chloro-1-[(1R)-1-cyclopropylpropyl]-3-(7-methoxy-2,3-dihydro-4H-1,4-benzoxazin-4-yl)-2(1H)-pyrazinone

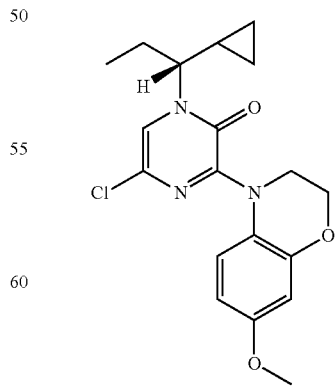

Prepared in a similar fashion as described for Example 556 using 3,5-dichloro-1-[(1R)-1-cyclopropylpropyl]-2

(1H)-pyrazinone and 7-methoxy-3,4-dihydro-2H-1,4-benzoxazine as the starting materials to give an oil. $^1$H NMR (300 MHz, CDCl$_3$): δ 6.98 (s, 1H), 6.94 (d, J=9.6 Hz, 1H), 6.44–6.41 (m, 2H), 4.33–4.30 (m, 2H), 4.18–4.08 (m, 3H), 3.75 (s, 3H), 1.92–1.78 (m, 2H), 1.10–1.00 (m, 1H), 0.95 (t, J=7.3 Hz, 3H), 0.81–0.77 (m, 1H), 0.60–0.48 (m, 2H), 0.38–0.20 (m, 1H); HRMS (ESI) m/z 376.1452 [(M+H)$^+$, calcd for C$_{19}$H$_{23}$N$_3$O$_3$Cl 376.1428].

Example 566

3-(5-Bromo-7-methoxy-2,3-dihydro-4H-1,4-benzoxazin-4-yl)-5-bromo-1-[(1R)-1-(methoxymethyl)propyl]-2(1H)-pyrazinone

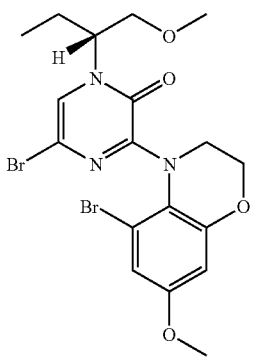

Prepared in a similar fashion as described for Example 556 using 3,5-dibromo-1-[(1R)-1-(methoxymethyl)propyl]-2(1H)-pyrazinone and 5-bromo-7-methoxy-3,4-dihydro-2H-1,4-benzoxazine as the starting materials to give an oil. $^1$H NMR (300 MHz, CDCl$_3$): δ 7.14 (s, 1H), 6.75 (d, J=2.5 Hz, 1H), 6.46 (d, J=2.5 Hz, 1H), 5.08–4.86 (m, 1H), 4.50–3.88 (m, 4H), 3.77 (s, 3H), 3.70–3.52 (m, 2H), 3.36 (s, 3H), 1.92–1.70 (m, 2H), 0.93 (t, J=7.5 Hz, 3H); HRMS (ESI) m/z 501.9992 [(M+H)$^+$, calcd for C$_{18}$H$_{22}$N$_3$O$_4$Br$_2$ 501.9977].

UTILITY

CRF-R1 Receptor Binding Assay for the Evaluation of Biological Activity.

The following is a description of the isolation of cell membranes containing cloned human CRF-R1 receptors for use in a standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately 1×10$^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl$_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from 10$^{-10}$–10$^{-5}$ M), 100 μl of $^{125}$I-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980), which provides Ki values for inhibition which are then used to assess biological activity.

A compound is considered to be active if it has a K$_i$ value of less than about 10000 nM for the inhibition of CRF. Preferred compounds have a K$_i$ value of less than about 1000 nM for the inhibition of CRF. More preferred compounds have a K$_i$ value of less than about 100 nM for the inhibition of CRF.

Compounds of the present invention have demonstrated a K$_i$ value of less than about 10000 nM for the inhibition of CRF in the CRF-R1 Receptor Binding Assay for the Evaluation of Biological Activity.

Alternate CRF-R1 Receptor Binding Assay for the Evaluation of Biological Activity.

The following is a description of the isolation of cell membranes containing cloned human CRF-R1 receptors for use in a standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 uM hygromycin. Cells surviving 4 weeks of selection in hygromycin were pooled, adapted to growth in suspension and used to generate membranes for the binding assay described below.

HEK 293 EBNA-1 cells (HEK 293E, Invitrogen, Calif.), were transfected with a vector encoding the human CRF-R1 gene using a standard calcium phosphate protocol. The vector sequence included the oriP origin of replication, which permits episomal maintenance in cells expressing the EBNA-1 gene, and the gene for hygromycin resistance. Following transfection, cells were pooled and plated into a medium containing hygromycin for the selection of cells expressing CRF-R1. After isolation, the cell pool CL0138 was assessed in radioligand binding and functional-based assays. These cells are maintained in Dulbecco's Modified Eagle medium (DMEM) containing 10% v/v fetal bovine serum (FBS), 2 mM L-glutamine and 400 µg/mL hygromycin. Cell pellets prepared from this cell line were used in $CRF_1$ competition binding assays. Individual aliquots containing approximately $1 \times 10^8$ of the suspended cells were then centrifuged to form a pellet, frozen and stored at $-80°$ C.

A frozen pellet described above containing 293EBNA cells transfected with hCRFR1 receptors or the rat frontal cortex tissue dissected from frozen rat brains was prepared as the source of membranes expressing CRF1 receptors used in binding assays. Tissue or pellets of whole cells were thawed on ice and homogenized in tissue buffer (containing 50 mM HEPES, 10 mM $MgCl_2$, 2 mM EGTA, and 1 µg/mL each of aprotonin, leupeptin, and pepstatin, pH 7.0@23° C.) using a Brinkman Polytron (PT-10, setting 6 for 10 seconds). The homogenate was centrifuged at 48,000×g for 12 min and the resulting pellet was washed by a single re-suspension and centrifugation step. Membranes from rat frontal cortex were prepared similarly except for the inclusion of an additional wash/centrifugation cycle. The final pellet was suspended in tissue buffer, and protein concentrations were determined using the bicinchoninic acid (BCA) assay (Pierce, Rockford, Ill.) with bovine serum albumin as standard.

Equilibrium competition binding experiments were performed using a modification of the methods described previously to determine binding affinities of compounds at $CRF_1$ receptors (Arvantis et al., 1999; Rominger et al., 1998). All small molecule ligands were initially prepared in 100% DMSO at a concentration of $10^{-2}$ M and diluted in assay buffer that was identical to the tissue buffer except for the inclusion of 0.15 mM bacitracin and 0.1% w/v ovalbumin. Competition assays were conducted in disposable polypropylene 96-well plates in a total volume of 300 µL. The reaction was initiated by the addition of 50 µL competing compounds in 12 concentrations (final concentrations ranging from $10^{-11}$ to $10^{-5}$ M), 100 µL assay buffer containing the radioligand [$^{125}$I]ovine CRF (final concentration 150 pM), and 150 µL membrane homogenate (containing 5-10 µg protein). The reaction mixtures were incubated to equilibrium for 2 h at 23° C. Specific binding was defined in the presence of 10 µM DMP 696 or SC241 for $CRF_1$ receptors. Competition binding assays were terminated by rapid filtration over GF/C glass-fibers (pre-soaked in 0.3% v/v polyethyleneimine) using a 96-well cell harvester followed by two-three washes with 0.3 mL cold wash buffer (PBS, pH 7.0, containing 0.01% Triton X-100). The filter was dried, and counted in a gamma counter or a 96-well Packard Top Counter at 80% efficiency. The $CRF_1$ competition binding to membranes from rat frontal cortex were performed similarly except for the radioligand concentration of [$^{125}$I]ovine CRF (final concentration approximately 200 pM) and membrane protein (40-65 µg/well) used in the binding.

The inhibiton of [$^{125}$I]ovine CRF binding to cell membranes by increasing concentrations of test drugs are analyzed by fitting data through the competition equation in the iterative nonlinear regression curve-fitting programs Prism (GraphPad Prism, San Diego, Calif.) to determine binding affinities ($IC_{50}$'s or Ki's) of ligands for $CRF_1$ receptors. A compound is considered to be active if it has a $K_i$ value of less than about 10000 nM for the inhibition of [$^{125}$I]ovine CRF binding.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6}$m) and 0.8 mg original wet weight tissue (approximately 40-60 mg protein). Reactions are initiated by the addition of 1 mM ATP/[$^{32}$P]ATP (approximately 2-4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I) or (II):

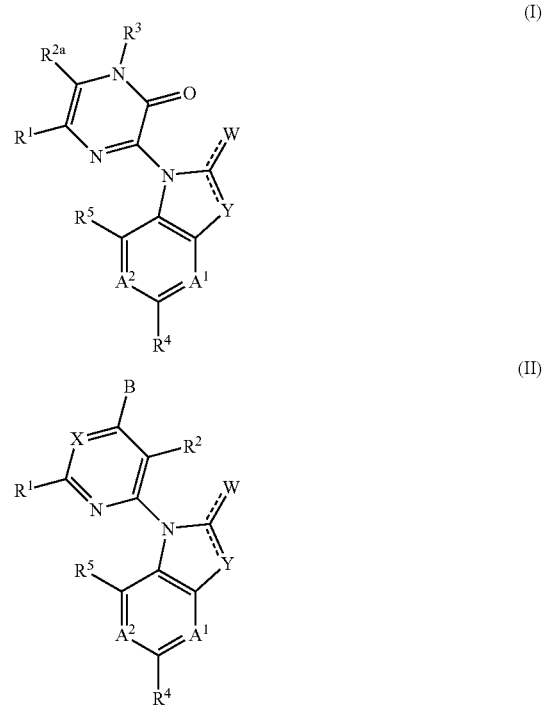

or a pharmaceutically acceptable salt form thereof, wherein:
X is N or $CR^1$;
provided that when X is N, $R^1$ can not be either —$NR^9R^{10}$ or —$NR^9COR^9$;
W is =O, =S, —H or (—H, —H);
Y is —C(=O)—, —$C(R^Y)_2$—, or —CH=;
$R^Y$ is independently, at each occurrence, selected from H, methyl, ethyl, and $C_1$–$C_2$ haloalkyl;
B is $R^3$, $NHR^3$, $NR^3R^1$, $OR^3$, or $SO_nR^3$;
$R^1$ is independently, at each occurrence, selected from H, halogen, —CN, $C_1$–$C_4$ haloalkyl, —$NR^9R^{10}$, —$NR^9COR^9$, —$COR^{10}$, —$OR^{10}$, SH, —$S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;
wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, —$NR^9R^{10}$, —$NR^9COR^9$, —$COR^{10}$, —$OR^{10}$, SH or —$S(O)_nR^{12}$;
$R^2$ is H, halogen, CN, $C_1$–$C_4$ haloalkyl, —$NR^9R^{10}$, $NR^9COR^9$, —$COR^{10}$, —$OR^{10}$, SH, —$S(O)_nR^{12}$, $C_1$–$C_4$ alkyl, $C_3$–$C_6$ cycloalkyl, or $C_4$–$C_8$ cycloalkylalkyl;
wherein each $C_1$–$C_4$ alkyl, $C_3$–$C_6$ cycloalkyl, or $C_4$–$C_8$ cycloalkylalkyl is optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;
$R^{2a}$ is H, F, Cl, Br, —CN, —OH, methyl, ethyl, propyl, cyclopropyl, cyclobutyl, methoxy, ethoxy, propoxy, $C_1$–$C_3$ alkoxy, cyclopropyloxy-, —$OCF_3$, —$CF_3$, —$CO_2CH_3$, —$CO_2CH_2CH_3$, —$C(O)CH_3$, —$C(O)CH_2CH_3$, —$CH_2OH$, —$CH_2OCH_3$, —$CH_2OCH_2CH_3$, —C(O)NH$_2$, —C(O)N(H)CH$_3$, —C(O)N(H)CH$_2$CH$_3$, —C(O)N(CH$_3$)$_2$, —C(O)N(CH$_3$)CH$_2$CH$_3$, —C(O)N(CH$_2$CH$_3$)$_2$, —S(O)$_2$N(CH$_3$)$_2$, —S(O)$_2$N(CH$_3$)CH$_2$CH$_3$, —S(O)$_2$N(CH$_2$CH$_3$)$_2$, —S(O)$_2$CH$_3$, —S(O)$_2$CH$_2$CH$_3$, —NH$_2$, —N(H)CH$_3$, —N(H)CH$_2$CH$_3$, —N(CH$_3$)$_2$, —N(CH$_3$)CH$_2$CH$_3$, —N(CH$_2$CH$_3$)$_2$, or —N(H)CF$_3$;

R$^3$ is C$_1$–C$_{10}$ alkyl, C$_3$–C$_{10}$ alkenyl, C$_3$–C$_{10}$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, or C$_6$–C$_{10}$ cycloalkenylalkyl;

wherein one carbon in any cycloalkyl ring may be replaced with O, S or NR$^9$; and wherein each C$_1$–C$_{10}$ alkyl, C$_3$–C$_{10}$ alkenyl, C$_3$–C$_8$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, or C$_6$–C$_{10}$ cycloalkenylalkyl is optionally substituted with 1, 2 or 3 substituents independently selected at each occurrence from C$_1$–C$_6$ alkyl, C$_2$–C$_6$ alkenyl, C$_2$–C$_{10}$ alkynyl, C$_3$–C$_6$ cycloalkyl, halogen, C$_1$–C$_4$ haloalkyl, cyano, —OR$^7$, SH, —S(O)$_n$R$^{11}$, —COR$^6$, —NHR$^6$SO$_2$R$^8$, —OC(O)NR$^6$R$^7$, —N$_3$, —OC(O)OR$^7$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, —CO$_2$H, aryl, heteroaryl and heterocyclyl;

alternatively, R$^3$ is —OR$^{3a}$, —NR$^{3a}$R$^{3b}$, —NHR$^{3a}$, —SO$_n$R$^{3a}$, —SO$_2$NHR$^{3a}$, —SO$_2$NR$^{3a}$R$^{3b}$, —COR$^{3a}$, —CONHR$^{3a}$, or —CONR$^{3a}$R$^{3b}$;

R$^{3a}$ and R$^{3b}$ are independently selected from C$_1$–C$_{10}$ alkyl, C$_2$–C$_{10}$ alkenyl, C$_2$–C$_{10}$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, and C$_6$–C$_{10}$ cycloalkenylalkyl;

wherein one carbon in any cycloalkyl may be replaced with O, S or NR$^9$; and wherein each C$_1$–C$_{10}$ alkyl, C$_2$–C$_{10}$ alkenyl, C$_2$–C$_{10}$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, and C$_6$–C$_{10}$ cycloalkenylalkyl is optionally substituted with 1 to 3 substituents independently selected at each occurrence from C$_1$–C$_6$ alkyl, C$_2$–C$_6$ alkenyl, C$_2$–C$_{10}$ alkynyl, C$_3$–C$_6$ cycloalkyl, halogen, C$_1$–C$_4$ haloalkyl, cyano, —OR$^7$, —SH, —S(O)$_n$R$^{11}$, —COR$^6$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —NHR$^6$SO$_2$R$^8$, —OC(O)NR$^6$R$^7$, —N$_3$, —OC(O)OR$^7$, —CONR$^6$R$^7$, —CO$_2$H, aryl, heteroaryl and heterocyclyl;

R$^4$ is independently selected in each occurrence from —H, —OR$^{10}$, —COR$^9$, —CO$_2$R$^8$, —CONR$^9$R$^{10}$, —CN, —NR$^9$R$^{10}$, —S(O)$_n$R$^{12}$, —S(O)$_2$NR$^9$R$^{10}$, —NO$_2$, halogen, C$_1$–C$_6$ alkyl, C$_1$–C$_4$ haloalkyl, C$_1$–C$_6$ haloalkoxy, C$_3$–C$_6$ cycloalkyl, C$_2$–C$_6$ alkenyl, C$_2$–C$_6$ alkynyl, aryl and heteroaryl;

wherein C$_1$–C$_6$ alkyl, C$_1$–C$_4$ haloalkyl, C$_3$–C$_6$ cycloalkyl, C$_2$–C$_6$ alkenyl, and C$_2$–C$_6$ alkynyl, are optionally substituted with —OR$^{10}$, —COR$^9$, —CO$_2$R$^8$, —CONR$^9$R$^{10}$, —CN, —NR$^9$R$^{10}$, —S(O)$_n$R$^{12}$, or halogen;

A$^1$ is CR$^5$;

A$^2$ is CR$^5$;

R$^5$ is independently selected at each occurrence from —H, C$_1$–C$_{10}$ alkyl, C$_1$–C$_4$ haloalkyl, C$_1$–C$_4$ haloalkoxy, C$_2$–C$_{10}$ alkenyl, C$_2$–C$_{10}$ alkynyl, C$_3$–C$_6$ cycloalkyl, C$_4$–C$_{12}$ cycloalkylalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —CO(NOR$^9$)R$^{11}$, —CO$_2$R$^8$, —S(O)$_2$NR$^9$R$^{10}$, and —S(O)$_n$R$^{11}$;

wherein C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are optionally substituted with 1 to 3 substituents independently selected at each occurrence from C$_1$–C$_4$ alkyl, C$_2$–C$_4$ alkenyl, C$_2$–C$_4$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, —NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, and —S(O)$_n$R$^{11}$;

alternatively, two R$^5$ groups on adjacent atoms can form a 5–7 membered fused ring, partially saturated or unsaturated, optionally containing 1–2 —O— or —SO$_n$— or 1–3 N heteroatoms provided the ring does not contain any S—S, O—O, S—O or N—S bonds;

said 5–7 membered fused ring optionally substituted with C$_1$–C$_4$ alkyl, C$_2$–C$_6$ alkenyl, C$_2$–C$_6$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$;

R$^6$ and R$^7$ are independently at each occurrence H, C$_1$–C$_6$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, C$_5$–C$_{12}$ bis(alkoxy)alkyl, aryl, aryl(C$_1$–C$_4$ alkyl)-, heteroaryl or heteroaryl(C$_1$–C$_4$ alkyl);

alternatively NR$^6$R$^7$ is piperidine, pyrrolidine, piperazine, N-methylpiperazine, morpholine or thiomorpholine;

R$^8$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl)-, heteroaryl or heteroaryl(C$_1$–C$_4$ alkyl);

R$^9$ and R$^{10}$ are independently at each occurrence selected from H, C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_2$–C$_6$ alkoxyalkyl, and C$_4$–C$_7$ cycloalkylalkyl;

R$^{11}$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl)-, heteroaryl, heteroaryl(C$_1$–C$_4$ alkyl), or —NR$^6$R$^7$;

R$^{12}$ is independently at each occurrence C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, or C$_4$–C$_7$ cycloalkylalkyl;

aryl is phenyl or naphthyl, each optionally substituted with 1 to 5 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{30}$, SH, —S(O)$_n$R$^{32}$, —COR$^{32}$, —CO$_2$R$^{32}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{32}$, —NR$^{29}$R$^{30}$, and —CONR$^{29}$R$^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2;

with the proviso that when the compound is of Formula II, X is N, W is (—H, —H), Y is CH$_2$, A$^1$ is CH, A$^2$ is CH, R$^4$ is H, R$^5$ is H, and R$^1$ is OR$^{10}$, then when R$^{10}$ is Me and R$^2$ is CHO, B is other than OMe, and when R$^{10}$ is $C_4$–$C_6$ alkynyl and R$^2$ is H, B is other than Me; and with the proviso that when the compound is of Formula II, X is N, W is —H, Y is CH═, R$^1$ is Me, A$^1$ is CH, R$^2$ is H, R$^4$ is H, R$^6$ is H, and R$^{10}$ is H, then when A$^2$ is CH, B is other than NHMe, and when A$^2$ is COMe, B is other than NH$_2$.

2. A compound of claim 1 of Formula (I):

or a pharmaceutically acceptable salt form thereof, wherein:

W is (—H, —H);

Y is —CH$_2$—, —CH(CH$_3$)—, or —C(CH$_3$)$_2$—;

R$^1$ is H, halogen, —CN, $C_1$–$C_2$ haloalkyl, —OR$^{10}$, $C_1$–$C_4$ alkyl, $C_2$–$C_4$ alkenyl, $C_2$–$C_4$ alkynyl, $C_3$–$C_4$ cycloalkyl, and $C_4$–$C_6$ cycloalkylalkyl;

wherein each $C_1$–$C_4$ alkyl, $C_2$–$C_4$ alkenyl, or $C_2$–$C_4$ alkynyl, is each optionally substituted with F, Cl, Br, CN, —OH, —CH$_3$, —OCH$_3$, —CF$_3$, or —OCF$_3$;

R$^{2a}$ is H, F, Cl, Br, —CN, —OH, —CH$_3$, —OCH$_3$, —CF$_3$, or —OCF$_3$;

R$^3$ is $C_1$–$C_8$ alkyl, $C_3$–$C_8$ alkenyl, $C_3$–$C_8$ alkynyl, $C_3$–$C_6$ cycloalkyl, $C_4$–$C_{10}$ cycloalkylalkyl, $C_2$–$C_{10}$ alkoxyalkyl, $C_5$–$C_6$ cycloalkenyl, or $C_6$–$C_{10}$ cycloalkenylalkyl;

wherein each $C_1$–$C_8$ alkyl, $C_3$–$C_8$ alkenyl, $C_3$–$C_8$ alkynyl, $C_3$–$C_6$ cycloalkyl, $C_4$–$C_{10}$ cycloalkylalkyl, $C_2$–$C_{10}$ alkoxyalkyl, $C_5$–$C_6$ cycloalkenyl, or $C_6$–$C_{10}$ cycloalkenylalkyl is optionally substituted with 1, 2 or 3 substituents independently selected at each occurrence from methyl, ethyl, cyclopropyl, cyclobutyl, F, Cl, Br, —CF$_3$, cyano, —OR$^7$, —S(O)$_n$R$^{11}$, —COR$^6$, —NHR$^6$SO$_2$R$^8$, —OC(O)NR$^6$R$^7$, —N$_3$, —OC(O)OR$^7$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, and —CO$_2$H;

alternatively, R$^3$ is —S(O)R$^{3a}$, —S(O)$_2$R$^{3a}$, —COR$^{3a}$, —CONHR$^{3a}$, or —CONR$^{3a}$R$^{3b}$;

R$^{3a}$ and R$^{3b}$ are independently selected from $C_1$–$C_8$ alkyl, $C_3$–$C_8$ alkenyl, $C_3$–$C_8$ alkynyl, $C_3$–$C_6$ cycloalkyl, $C_4$–$C_{10}$ cycloalkylalkyl, $C_2$–$C_{10}$ alkoxyalkyl, $C_5$–$C_6$ cycloalkenyl, or $C_6$–$C_{10}$ cycloalkenylalkyl;

wherein each $C_1$–$C_8$ alkyl, $C_3$–$C_8$ alkenyl, $C_3$–$C_8$ alkynyl, $C_3$–$C_6$ cycloalkyl, $C_4$–$C_{10}$ cycloalkylalkyl, $C_2$–$C_{10}$ alkoxyalkyl, $C_5$–$C_6$ cycloalkenyl, or $C_6$–$C_{10}$ cycloalkenylalkyl is optionally substituted with 1, 2 or 3 substituents independently selected at each occurrence from methyl, ethyl, methoxy, ethoxy, methyl-S—, ethyl-S—, cyclopropyl, cyclubutyl, F, Cl, —CF$_3$, and —OCF$_3$:

R$^4$ is —H, —OR$^{10}$, —COR$^9$, —CO$_2$R$^8$, —CONR$^9$R$^{10}$, —CN, —NR$^9$R$^{10}$, —S(O)$_n$R$^{12}$, —S(O)$_2$NR$^9$R$^{10}$, —NO$_2$, halogen, $C_1$–$C_4$ alkyl, $C_1$–$C_4$ haloalkyl, $C_1$–$C_4$ haloalkoxy, $C_3$–$C_6$ cycloalkyl, $C_2$–$C_4$ alkenyl, or $C_2$–$C_4$ alkynyl;

wherein $C_1$–$C_4$ alkyl, $C_1$–$C_4$ haloalkyl, $C_3$–$C_6$ cycloalkyl, $C_2$–$C_4$ alkenyl, or $C_2$–$C_4$ alkynyl, are optionally substituted with —OR$^{10}$, —COR$^9$, —CO$_2$R$^8$, —CONR$^9$R$^{10}$, —CN, —NR$^9$R$^{10}$, —S(O)$_n$R$^{12}$, or halogen;

A$^1$ is CR$^5$;

A$^2$ is CR$^5$;

R$^5$ is independently selected at each occurrence from —H, $C_1$–$C_6$ alkyl, $C_1$–$C_4$ haloalkyl, $C_1$–$C_4$ haloalkoxy, $C_2$–$C_6$ alkenyl, $C_2$–$C_6$ alkynyl, $C_3$–$C_6$ cycloalkyl, $C_4$–$C_{10}$ cycloalkylalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —CO(NOR$^9$)R$^{11}$, —CO$_2$R$^8$, —S(O)$_2$NR$^9$R$^{10}$, and —S(O)$_n$R$^{11}$;

wherein $C_1$–$C_6$ alkyl, $C_2$–$C_6$ alkenyl, $C_2$–$C_6$ alkynyl, $C_3$–$C_6$ cycloalkyl and $C_4$–$C_{10}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —NO$_2$, halogen, —CN, —NR$^6$R$^7$, —NR$^6$COR$^7$, NR$^6$CO$_2$R$^8$, —COR$^6$—OR$^7$, —CONR$^6$R$^7$, —CO$_2$R$^8$, —CO(NOR$^9$)R$^{11}$, and —S(O)$_n$R$^{11}$;

R$^6$ and R$^7$ are independently at each occurrence H, methyl, ethyl, propyl, or butyl;

R$^8$ is independently at each occurrence methyl, ethyl, propyl, or butyl;

R$^9$ and R$^{10}$ are independently at each occurrence selected from H, methyl, ethyl, propyl, or butyl;

R$^{11}$ is independently at each occurrence H, methyl, ethyl, propyl, butyl, or —NR$^6$R$^7$;

R$^{12}$ is independently at each occurrence methyl, ethyl, propyl, or butyl; and n is 0, 1, or 2.

3. A compound of claim 2 of Formula (I-b):

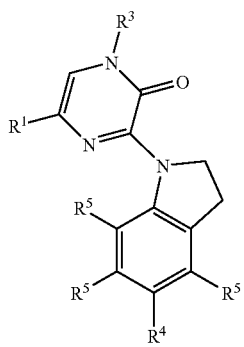

(I-b)

or a pharmaceutically acceptable salt form thereof, wherein:
R$^1$ is H, halogen, —CN, C$_1$–C$_2$ haloalkyl, —OR$^{10}$, or C$_1$–C$_3$ alkyl;
R$^3$ is C$_1$–C$_6$ alkyl, C$_3$–C$_6$ alkenyl, C$_3$–C$_6$ alkynyl, C$_3$–C$_6$ cycloalkyl, C$_4$–C$_7$ cycloalkylalkyl, C$_2$–C$_6$ alkoxyalkyl, C$_5$–C$_6$ cycloalkenyl, or C$_6$–C$_7$ cycloalkenylalkyl;
wherein each C$_1$–C$_6$ alkyl, C$_3$–C$_6$ alkenyl, C$_3$–C$_6$ alkynyl, C$_3$–C$_6$ cycloalkyl, C$_4$–C$_7$ cycloalkylalkyl, C$_2$–C$_6$ alkoxyalkyl, C$_5$–C$_6$ cycloalkenyl, or C$_6$–C$_7$ cycloalkenylalkyl is optionally substituted with 1 or 2 substituents independently selected at each occurrence from methyl, ethyl, methoxy, ethoxy, methyl-S—, ethyl-S—, cyclopropyl, cyclobutyl, F, Cl, —CF$_3$ and —OCF$_3$;
R$^4$ is —H, —OR$^{10}$, —CN, —NR$^9$R$^{10}$, —S(O)$_2$NR$^9$R$^{10}$, —NO$_2$, halogen, C$_1$–C$_4$ alkyl, C$_1$–C$_4$ haloalkyl, C$_1$–C$_4$ haloalkoxy, C$_2$–C$_4$ alkenyl, C$_2$–C$_4$ alkynyl, —SR$^{12}$, —S(O)R$^{12}$, or —S(O)$_2$R$^{12}$;
R$^5$ is independently at each occurrence —H, C$_1$–C$_4$ alkyl, C$_1$–C$_4$ haloalkyl, C$_1$–C$_4$ haloalkoxy, C$_2$–C$_4$ alkenyl, C$_2$–C$_4$ alkynyl, C$_3$–C$_4$ cycloalkyl, C$_4$–C$_5$ cycloalkylalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —S(O)$_2$NR$^9$R$^{10}$, —CO$_2$R$^8$, —SCH$_3$, —SCH$_2$CH$_3$, —S(O)R$^{11}$, or —S(O)$_2$R$^{11}$;
R$^6$ and R$^7$ are independently at each occurrence H, methyl, or ethyl;
R$^8$ is independently at each occurrence methyl or ethyl;
R$^9$ and R$^{10}$ are independently at each occurrence selected from H, methyl, or ethyl;
R$^{11}$ is independently at each occurrence methyl, ethyl, or —NR$^6$R$^7$; and
R$^{12}$ is independently at each occurrence methyl or ethyl.

4. A compound of claim 3 of Formula (I-c):

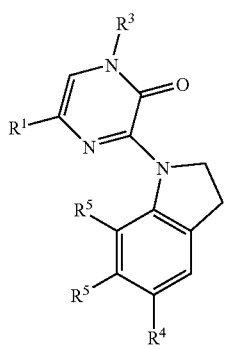

(I-c)

or a pharmaceutically acceptable salt form thereof, wherein:
R$^1$ is H, F, Cl, Br, —CN, methyl, ethyl, methoxy, or C$_1$–C$_2$ haloalkyl;
R$^3$ is C$_1$–C$_6$ alkyl optionally substituted with 1 or 2 substituents independently selected at each occurrence from methyl, ethyl, methoxy, ethoxy, methyl-S—, ethyl-S—, cyclopropyl, cyclobutyl, and —CF$_3$;
R$^4$ is —H, F, Cl, Br, —CN, methyl, ethyl, propyl, butyl, methoxy, ethoxy, propoxy, C$_1$–C$_2$ haloalkyl, or C$_1$–C$_2$ haloalkoxy; and
R$^5$ is independently at each occurrence —H, F, Cl, Br, —CN, methyl, ethyl, propyl, butyl, methoxy, ethoxy, propoxy, C$_1$–C$_2$ haloalkyl, or C$_1$–C$_2$ haloalkoxy.

5. A compound of claim 4 of Formula (I-c):

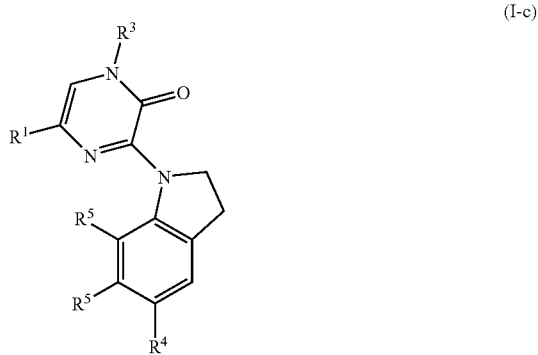

(I-c)

or a pharmaceutically acceptable salt form thereof, wherein:
R$^1$ is H, F, Cl, Br, methyl, ethyl, —CN, or —CF$_3$;
R$^3$ is butyl-, pentyl-, hexyl-, heptyl-, methoxy-ethyl-, methoxy-propyl-, methoxy-butyl-, methoxy-pentyl-, methoxy-hexyl-, methylthio-ethyl-, methylthio-propyl-, methylthio-butyl-, methylthio-pentyl-, methylthio-hexyl-, 1-cyclopropyl-propyl-, 1-cyclopropyl-butyl-, 1-cyclopropyl-pentyl-, 1-cyclobutyl-propyl-, 1-cyclobutyl-butyl-, 1-cyclobutyl-pentyl, 1-cyclopropyl-1-(CF$_3$)-methyl-, 1-cyclopropyl-2-(CF$_3$)-ethyl-, 1-cyclopropyl-3-(CF$_3$)-propyl-, 1-cyclobutyl-1-(CF$_3$)-methyl-, 1-cyclobutyl-2-(CF$_3$)-ethyl-, or 1-cyclobutyl-3-(CF$_3$)-propyl-;
R$^4$ is H, methyl-, ethyl-, methoxy-, ethoxy-, isopropoxy-, n-propoxy-, F, Cl, Br, —CF$_3$, —OCF$_3$, —OCHF$_2$, —CN; and
R$^5$ is independently at each occurrence, —H, methyl, ethyl, methoxy, ethoxy, F, Cl, Br, or —CF$_3$.

6. A compound of claim 2 selected from:
5-Chloro-3-(5,7-dichloro-2,3-dihydro-1H-indol-1-yl)-1-(1-ethylpropyl)-2(1H)-pyrazinone;
5-Chloro-3-(5,7-dichloro-2,3-dihydro-1H-indol-1-yl)-1-(1-ethyl-3-methoxypropyl)-2(1H)-pyrazinone;
5-Chloro-1-(1-ethylpropyl)-3-(5-methoxy-7-methyl-2,3-dihydro-1H-indol-1-yl)-2(1H)-pyrazinone;
3-(7-Bromo-5-methoxy-2,3-dihydro-1H-indol-1-yl)-5-chloro-1-(1-ethylpropyl)-2(1H)-pyrazinone;
3-(5,7-Dichloro-2,3-dihydro-1H-indol-1-yl)-1-(1-ethylpropyl)-5-methyl-2(1H)-pyrazinone;
3-(5-Methoxy-7-methyl-2,3-dihydro-1H-indol-1-yl)-1-(1-ethylpropyl)-5-methyl-2(1H)-pyrazinone;
5-Chloro-3-(7-chloro-5-methoxy-2,3-dihydro-1H-indol-1-yl)-1-(1-methylpropyl)-2(1H)-pyrazinone;

-3-(7-Bromo-5-methoxy-2,3-dihydro-1H-indol-1-yl)-5-chloro-1-(1-methylpropyl)-2(1H)-pyrazinone;
5-Chloro-3-(5-methoxy-7-methyl-2,3-dihydro-1H-indol-1-yl)-1-(1-methylpropyl)-2(1H)-pyrazinone;
5-Chloro-3-(5,7-dichloro-2,3-dihydro-1H-indol-1-yl)-1-(1-methylpropyl)-2(1H)-pyrazinone;
5-Bromo-3-(7-bromo-5-methoxy-2,3-dihydro-1H-indol-1-yl)-1-(1-ethylpropyl)-2(1H)-pyrazinone;
5-Bromo-1-(1-ethylpropyl)-3-(5-methoxy-7-methyl-2,3-dihydro-1H-indol-1-yl)-2(1H)-pyrazinone;
5-Bromo-3-(5,7-dichloro-2,3-dihydro-1H-indol-1-yl)-1-(1-ethylpropyl)-2(1H)-pyrazinone;
5-Chloro-3-(7-chloro-5-methoxy-2,3-dihydro-1H-indol-1-yl)-1-[(1R)-1-cyclopropylpropyl]-2(1H)-pyrazinone;
3-(7-Bromo-5-methoxy-2,3-dihydro-1H-indol-1-yl)-5-chloro-1-[(1R)-1-cyclopropylpropyl]-2(1H)-pyrazinone;
5-Chloro-1-[(1R)-1-cyclopropylpropyl]-3-(5-methoxy-7-methyl-2,3-dihydro-1H-indol-1-yl)-2(1H)-pyrazinone;
5-Chloro-1-[(1R)-1-cyclopropylpropyl]-3-(5,7-dichloro-2,3-dihydro-1H-indol-1-yl)-2(1H)-pyrazinone;
5-Chloro-1-[(1R)-1-cyclopropylpropyl]-3-(5,7-dibromo-2,3-dihydro-1H-indol-1-yl)-2(1H)-pyrazinone;
5-Chloro-3-(7-chloro-6-fluoro-5-methoxy-2,3-dihydro-1H-indol-1-yl)-1-[(1R)-1-cyclopropylpropyl]-2(1H)-pyrazinone;
5-Chloro-3-(7-chloro-5-methoxy-2,3-dihydro-1H-indol-1-yl)-1-[(1S)-1-cyclopropylpropyl]-2(1H)-pyrazinone;
3-(7-Bromo-5-methoxy-2,3-dihydro-1H-indol-1-yl)-5-chloro-1-[(1S)-1-cyclopropylpropyl]-2(1H)-pyrazinone;
5-Chloro-1-[(1S)-1-cyclopropylpropyl]-3-(5-methoxy-7-methyl-2,3-dihydro-1H-indol-1-yl)-2(1H)-pyrazinone;
5-Chloro-1-[(1S)-1-cyclopropylpropyl]-3-(5,7-dichloro-2,3-dihydro-1H-indol-1-yl)-2(1H)-pyrazinone;
5-Chloro-1-[(1S)-1-cyclopropylpropyl]-3-(5,7-dibromo-2,3-dihydro-1H-indol-1-yl)-2(1H)-pyrazinone;
5-Chloro-3-(7-chloro-6-fluoro-5-methoxy-2,3-dihydro-1H-indol-1-yl)-1-[(1S)-1-cyclopropylpropyl]-2(1H)-pyrazinone;
5-Chloro-3-(5,7-dichloro-2,3-dihydro-1H-indol-1-yl)-1-[(1R)-2-methoxy-1-methylethyl]-2(1H)-pyrazinone;
5-Chloro-3-(5,7-dibromo-2,3-dihydro-1H-indol-1-yl)-1-[(1R)-2-methoxy-1-methylethyl]-2(1H)-pyrazinone;
5-Chloro-3-(7-chloro-6-fluoro-5-methoxy-2,3-dihydro-1H-indol-1-yl)-1-[1-(methoxymethyl)propyl]-2(1H)-pyrazinone;
3-(7-Bromo-5-methoxy-2,3-dihydro-1H-indol-1-yl)-5-chloro-1-[(1R)-1-(methoxymethyl)propyl]-2(1H)-pyrazinone;
5-Chloro-3-(5,7-dichloro-2,3-dihydro-1H-indol-1-yl)-1-[(1R)-1-(methoxymethyl)propyl]-2(1H)-pyrazinone;
5-Bromo-3-(7-bromo-5-methoxy-2,3-dihydro-1H-indol-1-yl)-1-[(1R)-1-(methoxymethyl)propyl]-2(1H)-pyrazinone;
5-Bromo-3-(5-methoxy-7-methyl-2,3-dihydro-1H-indol-1-yl)-1-[(1R)-1-(methoxymethyl)propyl]-2(1H)-pyrazinone;
5-Bromo-3-(5,7-dichloro-2,3-dihydro-1H-indol-1-yl)-1-[(1R)-1-(methoxymethyl)propyl]-2(1H)-pyrazinone;
5-Bromo-3-(7-chloro-6-fluoro-5-methoxy-2,3-dihydro-1H-indol-1-yl)-1-[(1R)-1-(methoxymethyl)propyl]-2(1H)-pyrazinone;
3-(7-Bromo-5-methoxy-2,3-dihydro-1H-indol-1-yl)-5-chloro-1-[(1S)-1-(methoxymethyl)propyl]-2(1H)-pyrazinone;
5-Chloro-3-(5,7-dichloro-2,3-dihydro-1H-indol-1-yl)-1-[(1S)-1-(methoxymethyl)propyl]-2(1H)-pyrazinone;
5-Bromo-3-(5,7-dichloro-2,3-dihydro-1H-indol-1-yl)-1-[(1S)-1-(methoxymethyl)propyl]-2(1H)-pyrazinone;
5-Chloro-3-(5-methoxy-7-methyl-2,3-dihydro-1H-indol-1-yl)-1-[2-methyl-1-(1-methylethyl)propyl]-2(1H)-pyrazinone;
3-(7-Bromo-5-methoxy-2,3-dihydro-1H-indol-1-yl)-5-chloro-1-[2-(methylthio)ethyl]-2(1H)-pyrazinone;
5-Chloro-3-(5-methoxy-7-methyl-2,3-dihydro-1H-indol-1-yl)-1-[2-(methylthio)ethyl]-2(1H)-pyrazinone;
5-Chloro-3-(5,7-dichloro-2,3-dihydro-1H-indol-1-yl)-1-[2-(methylthio)ethyl]-2(1H)-pyrazinone;
5-Chloro-3-(7-chloro-5-methoxy-2,3-dihydro-1H-indol-1-yl)-1-(1-ethylpropyl)-6-methyl-2(1H)-pyrazinone;
5-Chloro-3-(7-chloro-5-methoxy-2,3-dihydro-1H-indol-1-yl)-1-(1-cyclobutylpropyl)-6-methyl-2(1H)-pyrazinone;
3-(5-Bromo-7-chloro-2,3-dihydro-1H-indol-1-yl)-5-chloro-1-methylpropyl-2(1H)-pyrazinone;
3-(5,7-Dichloro-2,3-dihydro-1H-indol-1-yl)-5-ethyl-1-(1-ethylpropyl)-2(1H)-pyrazinone;
3-(5-Bromo-7-chloro-2,3-dihydro-1H-indol-1-yl)-5-chloro-1-(1-ethylpropyl)-2(1H)-pyrazinone;
6-(5,7-Dichloro-2,3-dihydro-1H-indol-1-yl)-4-(1-ethylpropyl)-4,5-dihydro-5-oxo-2-pyrazinecarbonitrile;
3-(5-Bromo-7-chloro-2,3-dihydro-1H-indol-1-yl)-5-chloro-1-[(1R)-1-cyclopropylpropyl]-2(1H)-pyrazinone;
3-(5-Bromo-7-chloro-2,3-dihydro-1H-indol-1-yl)-5-chloro-1-[(1S)-1-cyclopropylpropyl]-2(1H)-pyrazinone;
5-Chloro-3-(7-chloro-5-methoxy-2,3-dihydro-1H-indol-1-yl)-1-[(1R)-1-(methoxymethyl)propyl]-2(1H)-pyrazinone;
5-Chloro-3-(5-methoxy-7-methyl-2,3-dihydro-1H-indol-1-yl)-1-[(1R)-1-(methoxymethyl)propyl]-2(1H)-pyrazinone;
1-[6-Chloro-4-[(1R)-1-(methoxymethyl)propyl]-3,4-dihydro-3-oxopyrazinyl]-5-methoxy-2,3-dihydro-1H-indole-7-carbonitrile;
5-Bromo-3-(5-bromo-7-chloro-2,3-dihydro-1H-indol-1-yl)-1-[(1R)-1-(methoxymethyl)propyl]-2(1H)-pyrazinone;
3-(5-Bromo-7-chloro-2,3-dihydro-1H-indol-1-yl)-5-chloro-1-[(1S)-1-(methoxymethyl)propyl]-2(1H)-pyrazinone; and
5-Chloro-3-(7-chloro-5-methoxy-2,3-dihydro-1H-indol-1-yl)-1-(1-cyclobutylpropyl)-2(1H)-pyrazinone.

7. A compound of claim 1 of Formula (I-a) or (II):

-continued

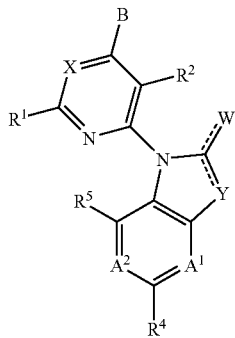

(II)

or a pharmaceutically acceptable salt form thereof, wherein:

X is N or $CR^1$;

provided that when X is N, $R^1$ can not be either $—NR^9R^{10}$ or $—NR^9COR^9$;

W is O, S, H or (—H, —H);

Y is CO, $CH_2$, or CH;

B is $R^3$, $NHR^3$, $NR^3R^1$, $OR^3$, or $SO_nR^3$;

$R^1$ is independently, at each occurrence, selected from H, halogen, —CN, $C_1$–$C_4$ haloalkyl, $—NR^9R^{10}$, $—NR^9COR^9$, $—COR^{10}$, $—OR^{10}$, SH, $—S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;

wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, $—NR^9R^{10}$, $—NR^9COR^9$, $—COR^{10}$, $—OR^{10}$, SH or $—S(O)_nR^{12}$;

$R^2$ is H, halogen, CN, $C_1$–$C_4$ haloalkyl, $—NR^9R^{10}$, $NR^9COR^9$, $—COR^{10}$, $—OR^{10}$, SH, $—S(O)_nR^{12}$, $C_1$–$C_4$ alkyl, $C_3$–$C_6$ cycloalkyl, or $C_4$–$C_8$ cycloalkylalkyl;

wherein each $C_1$–$C_4$ alkyl, $C_3$–$C_6$ cycloalkyl, or $C_4$–$C_8$ cycloalkylalkyl is optionally substituted with halogen, —CN, $C_1$–$C_4$ haloalkyl, $—NR^9R^{10}$, $—NR^9COR^9$, $—COR^{10}$, $—OR^{10}$, SH or $—S(O)_nR^{12}$;

$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;

wherein one carbon in any cycloalkyl ring may be replaced with O, S or $NR^9$; and wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, $—OR^7$, SH, $—S(O)_nR^{11}$, $—COR^6$, $—NHR^6SO_2R^8$, $—OC(O)NR^6R^7$, $—N_3$, $—OC(O)OR^7$, $—CO_2R^8$, $—OC(O)R^6$, $—NR^7COR^6$, $—N(COR^6)_2$, $—NR^7CONR^6R^7$, $—NR^7CO_2R^8$, $—NR^6R^7$, $—CONR^6R^7$, $—CO_2H$, aryl, heteroaryl and heterocyclyl;

alternatively, $R^3$ is $—OR^{3a}$, $—NR^{3a}R^{3b}$, $—NHR^{3a}$, $—SO_nR^{3a}$, $—SO_2NHR^{3a}$, $—SO_2NR^{3a}R^{3b}$, $—COR^{3a}$, $—CONHR^{3a}$, or $—CONR^{3a}R^{3b}$;

$R^{3a}$ and $R^{3b}$ are independently selected from $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl;

wherein one carbon in any cycloalkyl may be replaced with O, S or $NR^9$; and wherein each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_6$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, $—OR^7$, —SH, $—S(O)_nR^{11}$, $—COR^6$, $—CO_2R^8$, $—OC(O)R^6$, $—NR^7COR^6$, $—N(COR^6)_2$, $—NR^7CONR^6R^7$, $—NR^7CO_2R^8$, $—NR^6R^7$, $—NHR^6SO_2R^8$, $—OC(O)NR^6R^7$, $—N_3$, $—OC(O)OR^7$, $—CONR^6R^7$, $—CO_2H$, aryl, heteroaryl and heterocyclyl;

$R^4$ is independently selected in each occurrence from —H, $—OR^{10}$, $—COR^9$, $—CO_2R^8$, $—CONR^9R^{10}$, —CN, $—NR^9R^{10}$, $—S(O)_nR^{12}$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with $—OR^{10}$, $—COR^9$, $—CO_2R^8$, $—CONR^9R^{10}$, —CN, $—NR^9R^{10}$, $—S(O)_nR^{12}$, or halogen;

$A^1$ is $CR^5$;

$A^2$ is $CR^5$;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, $—NO_2$, halogen, —CN, $—NR^6R^7$, $—NR^6COR^7$, $—NR^6CO_2R^8$, $—COR^6$—$OR^7$, $—CONR^6R^7$, $—CO(NOR^9)R^{11}$, $—CO_2R^8$, or $—S(O)_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, $—NO_2$, halogen, —CN, $—NR^6R^7$, $—NR^6COR^7$, $NR^6CO_2R^8$, $—COR^6$—$OR^7$, $—CONR^6R^7$, $—CO_2R^8$, $—CO(NOR^9)R^7$, or $—S(O)_nR^{11}$;

alternatively, two $R^5$ groups on adjacent atoms can form a 5–7 membered fused ring, partially saturated or unsaturated, optionally containing 1–2 —O— or $—SO_n—$ or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, $—NO_2$, halogen, —CN, $—NR^6R^7$, $NR^6COR^7$, $NR^6CO_2R^8$, $—COR^6$—$OR^7$, $—CONR^6R^7$, $—CO_2R^8$, $—CO(NOR^9)R^7$, or $—S(O)_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl ($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

121

R¹¹ is independently at each occurrence C₁–C₄ alkyl, C₁–C₄ haloalkyl, C₃–C₆ cycloalkyl, C₄–C₁₂ cycloalkylalkyl, aryl, aryl(C₁–C₄ alkyl)-, heteroaryl, heteroaryl(C₁–C₄ alkyl), or —NR⁶R⁷;

R¹² is independently at each occurrence C₁–C₄ alkyl, C₁–C₄ haloalkyl, C₃–C₆ alkenyl, C₃–C₆ alkynyl, C₃–C₆ cycloalkyl, or C₄–C₇ cycloalkylalkyl;

aryl is phenyl or naphthyl, each optionally substituted with 1 to 5 substituents independently selected at each occurrence from C₁–C₆ alkyl, C₃–C₆ cycloalkyl, C₄–C₇ cycloalkylalkyl, C₂–C₆ alkenyl, C₂–C₆ alkynyl, halogen, C₁–C₄ haloalkyl, cyano, —OR³⁰, —SH, —S(O)ₙR³², —COR³², —CO₂R²⁸, —OC(O)R³², —NR²⁹COR²⁹, —N(COR³²)₂, —NR²⁹CONR²⁹R³⁰, —NR²⁹CO₂R²⁸, —NR²⁹R³⁰, and —CONR²⁹R³⁰;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from C₁–C₆ alkyl, C₃–C₆ cycloalkyl, C₄–C₇ cycloalkylalkyl, C₂–C₆ alkenyl, C₂–C₆ alkynyl, halogen, C₁–C₄ haloalkyl, cyano, —OR³⁰, —SH, —S(O)ₙR³², —COR³², —CO₂R²⁸, —OC(O)R³², —NR²⁹COR²⁹, —N(COR³²)₂, —NR²⁹CONR²⁹R³⁰, —NR²⁹CO₂R²⁸, —NR²⁹R³⁰, and —CONR²⁹R³⁰;

heterocyclyl is saturated or partially saturated heteroaryl, optionally substituted with 1 to 3 substituents independently selected at each occurrence from C₁–C₆ alkyl, C₃–C₆ cycloalkyl, C₄–C₇ cycloalkylalkyl, C₂–C₆ alkenyl, C₂–C₆ alkynyl, halogen, C₁–C₄ haloalkyl, cyano, —OR³⁰, SH, —S(O)ₙR³², —COR³², —CO₂R³², —OC(O)R³², —NR²⁹COR²⁹, —N(COR³²)₂, —NR²⁹CONR²⁹R³⁰, —NR²⁹CO₂R³², —NR²⁹R³⁰, and —CONR²⁹R³⁰;

R²⁸ is independently at each occurrence C₁–C₄ alkyl, C₁–C₄ haloalkyl, C₃–C₆ cycloalkyl, C₄–C₁₂ cycloalkylalkyl, phenyl, or phenyl(C₁–C₄ alkyl)-;

R²⁹ and R³⁰ are independently at each occurrence selected from H, C₁–C₄ alkyl, C₁–C₄ haloalkyl, C₃–C₆ alkenyl, C₃–C₆ alkynyl, C₃–C₆ cycloalkyl, C₂–C₆ alkoxyalkyl, and C₄–C₇ cycloalkylalkyl;

R³² is independently at each occurrence C₁–C₄ alkyl, C₁–C₄ haloalkyl, C₃–C₆ alkenyl, C₃–C₆ alkynyl, C₃–C₆ cycloalkyl, or C₄–C₇ cycloalkylalkyl; and n is 0, 1, or 2.

8. A compound of claim 7 of Formula (I-a):

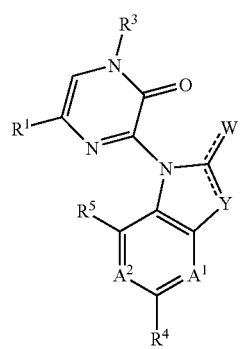

(I-a)

122 wherein:
W is (—H, —H);
Y is CH₂;
R¹ is independently, at each occurrence, selected from H, halogen, —CN, C₁–C₄ haloalkyl, —NR⁹R¹⁰, —NR⁹COR⁹, —COR¹⁰, —OR¹⁰, SH, —S(O)ₙR¹², C₁–C₆ alkyl, C₂–C₆ alkenyl, C₂–C₆ alkynyl, C₃–C₆ cycloalkyl, and C₄–C₈ cycloalkylalkyl;

wherein each C₁–C₆ alkyl, C₂–C₆ alkenyl, C₂–C₆ alkynyl, C₃–C₆ cycloalkyl, or C₄–C₈ cycloalkylalkyl is each optionally substituted with halogen, CN, C₁–C₄ haloalkyl, —NR⁹R¹⁰, —NR⁹COR⁹, —COR¹⁰, —OR¹⁰, SH or —S(O)ₙR¹²;

R² is H, halogen, CN, C₁–C₄ haloalkyl, —NR⁹R¹⁰, NR⁹COR⁹, —COR¹⁰, —OR¹⁰, SH, —S(O)ₙR¹², C₁–C₄ alkyl, C₃–C₆ cycloalkyl, or C₄–C₇ cycloalkylalkyl;

wherein each C₁–C₄ alkyl, C₃–C₆ cycloalkyl, or C₄–C₇ cycloalkylalkyl is optionally substituted with halogen, —CN, C₁–C₄ haloalkyl, —NR⁹R¹⁰, —NR⁹COR⁹, —COR¹⁰, —OR¹⁰, SH or —S(O)ₙR¹²;

R³ is C₁–C₁₀ alkyl, C₃–C₁₀ alkenyl, C₃–C₁₀ alkynyl, C₃–C₈ cycloalkyl, C₄–C₁₂ cycloalkylalkyl, C₂–C₁₀ alkoxyalkyl, C₅–C₁₀ cycloalkenyl, or C₆–C₁₀ cycloalkenylalkyl;

wherein one carbon in any cycloalkyl ring may be replaced with O, S or NR⁹; and wherein each C₁–C₁₀ alkyl, C₃–C₁₀ alkenyl, C₃–C₈ alkynyl, C₃–C₈ cycloalkyl, C₄–C₁₂ cycloalkylalkyl, C₂–C₁₀ alkoxyalkyl, C₅–C₁₀ cycloalkenyl, or C₆–C₁₀ cycloalkenylalkyl is optionally substituted with 1, 2 or 3 substituents independently selected at each occurrence from C₁–C₆ alkyl, C₂–C₆ alkenyl, C₂–C₁₀ alkynyl, C₃–C₆ cycloalkyl, halogen, C₁–C₄ haloalkyl, cyano, —OR⁷, SH, —S(O)ₙR¹¹, —COR⁶, —NHR⁶SO₂R⁸, —OC(O)NR⁶R⁷, —N₃, —OC(O)OR⁷, —CO₂R⁸, —OC(O)R⁶, —NR⁷COR⁶, —N(COR⁶)₂, —NR⁷CONR⁶R⁷, —NR⁷CO₂R⁸, —NR⁶R⁷, —CONR⁶R⁷, —CO₂H, aryl, heteroaryl and heterocyclyl;

alternatively, R³ is —OR³ᵃ, —NR³ᵃR³ᵇ, —NHR³ᵃ, SOₙR³ᵃ, —SO₂NHR³ᵃ, —SO₂NR³ᵃR³ᵇ, —COR³ᵃ, —CONHR³ᵃ, or —CONR³ᵃR³ᵇ;

R³ᵃ and R³ᵇ are independently selected from C₁–C₁₀ alkyl, C₂–C₁₀ alkenyl, C₂–C₁₀ alkynyl, C₃–C₈ cycloalkyl, C₄–C₁₂ cycloalkylalkyl, C₂–C₁₀ alkoxyalkyl, C₅–C₁₀ cycloalkenyl, and C₆–C₁₀ cycloalkenylalkyl;

wherein one carbon in any cycloalkyl may be replaced with O, S or NR⁹; and wherein each C₁–C₁₀ alkyl, C₂–C₁₀ alkenyl, C₂–C₁₀ alkynyl, C₃–C₈ cycloalkyl, C₄–C₁₂ cycloalkylalkyl, C₂–C₁₀ alkoxyalkyl, C₅–C₁₀ cycloalkenyl, and C₆–C₁₀ cycloalkenylalkyl is optionally substituted with 1 to 3 substituents independently selected at each occurrence from C₁–C₆ alkyl, C₂–C₆ alkenyl, C₂–C₁₀ alkynyl, C₃–C₆ cycloalkyl, halogen, C₁–C₄ haloalkyl, cyano, —OR⁷, —SH, —S(O)ₙR¹¹, —COR⁶, —CO₂R⁸, —OC(O)R⁶, —NR⁷COR⁶, —N(COR⁶)₂, —NR⁷CONR⁶R⁷, —NR⁷CO₂R⁸, —NR⁶R⁷, —NHR⁶SO₂R⁸, —OC(O)NR⁶R⁷, —N₃, —OC(O)OR⁷, —CONR⁶R⁷, —CO₂H, aryl, heteroaryl and heterocyclyl;

R⁴ is independently selected in each occurrence from —H, —OR¹⁰, —COR⁹, —CO₂R⁸, —CONR⁹R¹⁰, —CN, —NR⁹R¹⁰, —S(O)ₙR¹², halogen, C₁–C₆ alkyl, C₁–C₄ haloalkyl, C₁–C₆ haloalkoxy, C₃–C₆ cycloalkyl, C₂–C₆ alkenyl, C₂–C₆ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2R^8$, —$CONR^9R^{10}$, —CN, —$NR^9R^{10}$, —$S(O)_nR^{12}$, or halogen;

$A^1$ is CH;

$A^2$ is CH;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —CO(NOR$^9$)$R^{11}$, —$CO_2R^8$, or —S(O)$_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —CO(NOR$^9$)$R^7$, or —S(O)$_nR^{11}$;

alternatively, two $R^5$ groups on adjacent atoms can form a 5–7 membered fused ring, partially saturated or unsaturated, optionally containing 1–2 —O— or —SO$_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$, —$COR^6$—$OR^7$, —$CONR^6R^7$, —$CO_2R^8$, —CO(NOR$^9$)$R^7$, or —S(O)$_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S(O)$_nR^{32}$, —$COR^{32}$, —$CO_2R^{28}$, —OC(O)$R^{32}$, —$NR^{29}COR^{29}$, —N(COR$^{32}$)$_2$, —$NR^{29}CONR^{29}R^{30}$, —$NR^{29}CO_2R^{28}$, —$NR^{29}R^{30}$, and —$CONR^{29}R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S(O)$_nR^{32}$, —$COR^{32}$, —$CO_2R^{28}$, —OC(O)$R^{32}$, —$NR^{29}COR^{29}$, —N(COR$^{32}$)$_2$, —$NR^{29}CONR^{29}R^{30}$, —$NR^{29}CO_2R^{28}$, —$NR^{29}R^{30}$, and —$CONR^{29}R^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, SH, —S(O)$_nR^{32}$, —$COR^{32}$, —$CO_2R^{32}$, —OC(O)$R^{32}$, —$NR^{29}COR^{29}$, —N(COR$^{32}$)$_2$, —$NR^{29}CONR^{29}R^{30}$, —$NR^{29}CO_2R^{32}$, —$NR^{29}R^{30}$, and —$CONR^{29}R^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

9. A compound of claim 8 of Formula (I-a) wherein:

W is (—H, —H);

Y is $CH_2$;

$R^1$ is a halogen;

$R^3$ is $C_1$–$C_{10}$ alkyl, $C_3$–$C_8$ cycloalkyl, $C_4$–$C_{12}$ cycloalkylalkyl, or $C_2$–$C_{10}$ alkoxyalkyl;

wherein one carbon in any cycloalkyl ring may be replaced with O, S or $NR^9$;

$R^4$ and $R^5$ are independently selected at each occurrence from —$OR^{10}$, halogen, $C_1$–$C_6$ alkyl, and $C_1$–$C_6$ haloalkoxy;

$A^1$ is CH;

$A^2$ is CH;

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl.

10. A compound of claim 9 of Formula (I-a) wherein:

W is (—H, —H);

Y is $CH_2$;

$R^1$ is a halogen;

$R^3$ is $C_1$–$C_{10}$ alkyl, $C_3$–$C_8$ cycloalkyl, $C_4$–$C_{12}$ cycloalkylalkyl, or $C_2$–$C_{10}$ alkoxyalkyl;

$R^4$ and $R^5$ are independently selected in each occurrence from —$OR^{10}$, halogen, $C_1$–$C_6$ alkyl, and $C_1$–$C_6$ haloalkoxy;

$A^1$ is CH;

$A^2$ is CH; and $R^{10}$ is independently at each occurrence selected from $C_1$–$C_4$ alkyl.

11. A compound of claim 10 selected from:

5-Chloro-1-(1-cyclopropylpropyl)-3-(5,7-dichloro-2,3-dihydro-1H-indol-1-yl)-2(1H)-pyrazinone;

5-Chloro-3-(5,7-dichloro-2,3-dihydro-1H-indol-1-yl)-1-[1-(methoxymethyl)propyl]-2(1H)-pyrazinone;

5-Chloro-3-(7-chloro-5-methoxy-2,3-dihydro-1H-indol-1-yl)-1-[1-(methoxymethyl)propyl]-2(1H)-pyrazinone;

5-Chloro-3-(7-chloro-5-methoxy-2,3-dihydro-1H-indol-1-yl)-1-(1-ethyl-3-methoxypropyl)-2(1H)-pyrazinone;

5-Chloro-3-(5-methoxy-7-methyl-2,3-dihydro-1H-indol-1-yl)-1-[1-(methoxymethyl)propyl]-2(1H)-pyrazinone;

5-Chloro-3-(7-bromo-5-methoxy-2,3-dihydro-1H-indol-1-yl)-1-[1-(methoxymethyl)propyl]-2(1H)-pyrazinone; and 5-Chloro-3-(7-bromo-5-methoxy-2,3-dihydro-1H-indol-1-yl)-1-(1-ethyl-3-methoxypropyl)-2(1H)-pyrazinone.

12. A compound of claim 7 of Formula (II)

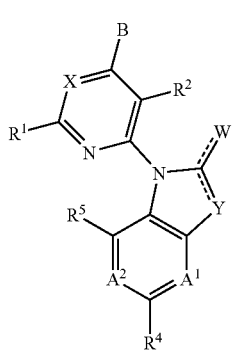

(II)

wherein:

X is N;

W is (—H, —H);

Y is $CH_2$;

B is $NHR^3$;

$R^1$ is independently, at each occurrence, selected from H, halogen, —CN, $C_1$–$C_4$ haloalkyl, —$NR^9R^{10}$, —$NR^9COR^9$, —$COR^{10}$, —$OR^{10}$, SH, —$S(O)_nR^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;

wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, —$NR^9R^{10}$, —$NR^9COR^9$, —$COR^{10}$, —$OR^{10}$, SH or —$S(O)_nR^{12}$;

$R^2$ is H, halogen, CN, $C_1$–$C_4$ haloalkyl, —$COR^{10}$, —$OR^{10}$, SH, —$S(O)_nR^{12}$, $C_1$–$C_4$ alkyl, $C_3$–$C_6$ cycloalkyl, or $C_4$–$C_7$ cycloalkylalkyl;

wherein each $C_1$–$C_4$ alkyl, $C_3$–$C_6$ cycloalkyl, or $C_4$–$C_7$ cycloalkylalkyl is optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;

$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;

wherein one carbon in any cycloalkyl ring may be replaced with O, S or $NR^9$; and wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_nR^{11}$, —$COR^6$, —$NHR^6SO_2R^8$, —$OC(O)NR^6R^7$, —$N_3$, —$OC(O)OR^7$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$CO_2H$, aryl, heteroaryl and heterocyclyl;

$R^4$ is independently selected in each occurrence from —H, —$OR^{10}$, —$COR^9$, —$CO_2R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_1$–$C_6$ haloalkoxy, $C_3$–$C_6$ cycloalkyl, $C_2$–$C_6$ alkenyl, $C_2$–$C_6$ alkynyl, aryl and heteroaryl;

wherein $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl, are optionally substituted with —$OR^{10}$, —$COR^9$, —$CO_2R^8$, —$CONR^9R^{10}$, —CN, —$NR^9R^{10}$, —$S(O)_nR^{12}$, or halogen;

$A^1$ are CH;

$A^2$ are CH;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO(NOR^9)R^{11}$, —$CO_2R^8$, or —$S(O)_nR^{11}$;

wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

alternatively, two $R^5$ groups on adjacent atoms can form a 5–7 membered fused ring, partially saturated or unsaturated, optionally containing 1–2 —O— or —$SO_n$— or 1–3 N heteroatoms provided the ring does not contain any S—S, O—O, S—O or N—S bonds;

said 5–7 membered fused ring optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$;

$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl or heteroaryl($C_1$–$C_4$ alkyl);

alternatively $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl, heteroaryl($C_1$–$C_4$ alkyl), or —$NR^6R^7$;

$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;

aryl is phenyl or naphthyl, each optionally substituted with 1 to 5 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —S(O)$_n R^{32}$ —$COR^{32}$, —$CO_2R^{28}$, —$OC(O)R^{32}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, —SH, —$S(O)_n R^{32}$, —$COR^{32}$, —$CO_2R^{28}$, —$OC(O)R^{32}$, —$NR^{29}COR^{29}$, —$N(COR^{32})_2$, —$NR^{29}CONR^{29}R^{30}$, —$NR^{29}CO_2R^{28}$, —$NR^{29}R^{30}$, and —$CONR^{29}R^{30}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{30}$, SH, —$S(O)_n R^{32}$, —$COR^{32}$, —$CO_2R^{32}$, —$OC(O)R^{32}$, —$NR^{29}COR^{29}$, —$N(COR^{32})_2$, —$NR^{29}CONR^{29}R^{30}$, —$NR^{29}CO_2R^{32}$, —$NR^{29}R^{30}$, and —$CONR^{29}R^{30}$;

$R^{28}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, phenyl, or phenyl($C_1$–$C_4$ alkyl)-;

$R^{29}$ and $R^{30}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, and $C_4$–$C_7$ cycloalkylalkyl;

$R^{32}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl; and n is 0, 1, or 2.

13. A compound of claim 12 wherein:
X is N;
W is (—H, —H);
Y is $CH_2$;
B is $NHR^3$;
$R^1$ is $C_1$–$C_6$ alkyl;
$R^2$ is H, halogen, CN, or —$COR^{10}$;
$R^4$ and $R^5$ are independently selected in each occurrence —$OR^{10}$, halogen, or $C_1$–$C_6$ haloalkoxy;
$A^1$ and $A^2$ are CH; and
$R^{10}$ is H.

14. A compound of claim 13 selected from:
4-(5,7-dichloro-2,3-dihydro-1H-indol-1-yl)-6-(1-ethylpropylamino)-2-methylpyrimidine;
5-chloro-4-(5,7-dichloro-2,3-dihydro-1H-indol-1-yl)-6-(1-ethylpropylamino)-2-methylpyrimidine;
5-bromo-4-(5,7-dichloro-2,3-dihydro-1H-indol-1-yl)-6-(1-ethylpropylamino)-2-methylpyrimidine;
4-(5,7-dichloro-2,3-dihydro-1H-indol-1-yl)-6-(1-ethylpropylamino)-5-iodo-2-methylpyrimidine;
5-cyano-4-(5,7-dichloro-2,3-dihydro-1H-indol-1-yl)-6-(1-ethylpropylamino)-2-methylpyrimidine;
4-(5,7-dichloro-2,3-dihydro-1H-indol-1-yl)-6-(1-ethylpropylamino)-5-formyl-2-methylpyrimidine;
4-(5,7-dichloro-2,3-dihydro-1H-indol-1-yl)-6-(1-ethylpropylamino)-5-hydroxymethyl-2-methylpyrimidine;
4-(7-chloro-5-methoxy-2,3-dihydro-1H-indol-1-yl)-6-(1-ethylpropylamino)-2-methylpyrimidine;
4-(7-chloro-5-methoxy-2,3-dihydro-1H-indol-1-yl)-5-cyano-6-(1-ethylpropylamino)-2-methylpyrimidine;
4-(7-chloro-5-methoxy-2,3-dihydro-1H-indol-1-yl)-6-(1-ethylpropylamino)-5-formyl-2-methylpyrimidine;
4-(7-chloro-5-methoxy-2,3-dihydro-1H-indol-1-yl)-6-[1-(1-ethyl-3-methoxy)propylamino]-2-methylpyrimidine;
4-(7-chloro-5-methoxy-2,3-dihydro-1H-indol-1-yl)-6-[1-(1-ethyl-3-methoxy)propylamino]-5-iodo-2-methylpyrimidine;
4-(7-chloro-5-methoxy-2,3-dihydro-1H-indol-1-yl)-5-cyano-6-[1-(1-ethyl-3-methoxy)propylamino]-2-methylpyrimidine;
4-(7-chloro-5-methoxy-2,3-dihydro-1H-indol-1-yl)-6-[1-(1-methoxymethyl)propylamino]-2-methylpyrimidine;
4-(7-chloro-5-methoxy-2,3-dihydro-1H-indol-1-yl)-5-iodo-6-[1-(1-methoxymethyl)propylamino]-2-methylpyrimidine;
4-(7-chloro-5-methoxy-2,3-dihydro-1H-indol-1-yl)-5-cyano-6-[1-(1-methoxymethyl)propylamino]-2-methylpyrimidine;
4-(7-chloro-5-methoxy-2,3-dihydro-1H-indol-1-yl)-5-formyl-6-[1-(1-methoxymethyl)propylamino]-2-methylpyrimidine;
4-(7-chloro-5-methoxy-2,3-dihydro-1H-indol-1-yl)-6-(1-methylbutylamino)-2-methylpyrimidine;
4-(7-chloro-5-methoxy-2,3-dihydro-1H-indol-1-yl)-6-(1-methylpropylamino)-2-methylpyrimidine; and
4-(7-chloro-5-methoxy-2,3-dihydro-1H-indol-1-yl)-6-[1-(1-cyclobutyl)ethylamino]-2-methylpyrimidine.

15. A compound of claim 7 wherein:
X is $CR^1$;
W is (—H, —H);
Y is $CH_2$;
B is $NHR^3$;
$R^1$ is independently, at each occurrence, selected from H, halogen, —CN, $C_1$–$C_4$ haloalkyl, —$NR^9R^{10}$, —$NR^9COR^9$, —$COR^{10}$, —$OR^{10}$, SH, —$S(O)_n R^{12}$, $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl;
wherein each $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl is each optionally substituted with halogen, CN, $C_1$–$C_4$ haloalkyl, —$NR^9R^{10}$, —$NR^9COR^9$, —$COR^{10}$, —$OR^{10}$, SH or —$S(O)_n R^{12}$;
$R^2$ is H, halogen, CN, $C_1$–$C_4$ haloalkyl, —$COR^{10}$, —$OR^{10}$, SH, —$S(O)_n R^{12}$, $C_1$–$C_4$ alkyl, $C_3$–$C_6$ cycloalkyl, or $C_4$–$C_7$ cycloalkylalkyl;
wherein each $C_1$–$C_4$ alkyl, $C_3$–$C_6$ cycloalkyl, or $C_4$–$C_7$ cycloalkylalkyl is optionally substituted with halogen, —CN, $C_1$–$C_4$ haloalkyl, —$NR^9R^1$, —$NR^9COR^9$, —$COR^{10}$, —$OR^{10}$, SH or —$S(O)_n R^{12}$;
$R^3$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl;
wherein one carbon in any cycloalkyl ring may be replaced with O, S or $NR^9$; and
wherein each $C_1$–$C_{10}$ alkyl, $C_3$–$C_{10}$ alkenyl, $C_3$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_6$–$C_{10}$ cycloalkenylalkyl is optionally substituted with 1, 2 or 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_n R^{11}$, —$COR^6$, —$NHR^6SO_2R^8$, —$OC(O)NR^6R^7$, —$N_3$, —$OC(O)OR^7$, —$CO_2R^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, —CO$_2$H, aryl, heteroaryl and heterocyclyl;

R$^4$ is independently selected in each occurrence from —H, —OR$^{10}$, —COR$^9$, —CO$_2$R$^8$, —CONR$^9$R$^{10}$, —CN, —NR$^9$R$^{10}$, —S(O)$_n$R$^{12}$, halogen, C$_1$–C$_6$ alkyl, C$_1$–C$_4$ haloalkyl, C$_1$–C$_6$ haloalkoxy, C$_3$–C$_6$ cycloalkyl, C$_2$–C$_6$ alkenyl, C$_2$–C$_6$ alkynyl, aryl and heteroaryl;

wherein C$_1$–C$_6$ alkyl, C$_1$–C$_4$ haloalkyl, C$_3$–C$_6$ cycloalkyl, C$_2$–C$_6$ alkenyl, and C$_2$–C$_6$ alkynyl, are optionally substituted with —OR$^{10}$, —COR$^9$, —CO$_2$R$^8$, —CONR$^9$R$^{10}$, —CN, —NR$^9$R$^{10}$, —S(O)$_n$R$^{12}$, or halogen;

A$^1$ are CH;

A$^2$ are CH;

R$^5$ is independently at each occurrence —H, C$_1$–C$_{10}$ alkyl, C$_1$–C$_4$ haloalkyl, C$_1$–C$_4$ haloalkoxy, C$_2$–C$_{10}$ alkenyl, C$_2$–C$_{10}$ alkynyl, C$_3$–C$_6$ cycloalkyl, C$_4$–C$_{12}$ cycloalkylalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —CO(NOR$^9$)R$^{11}$, —CO$_2$R$^8$, or —S(O)$_n$R$^{11}$;

wherein C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are optionally substituted with 1 to 3 substituents independently selected at each occurrence from C$_1$–C$_4$ alkyl, C$_2$–C$_4$ alkenyl, C$_2$–C$_4$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, —NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$;

alternatively, two R$^5$ groups on adjacent atoms can form a 5–7 membered fused ring, partially saturated or unsaturated, optionally containing 1–2 —O— or —SO$_n$— or 1–3 N heteroatoms provided the ring does not contain any S—S, O—O, S—O or N—S bonds;

said 5–7 membered fused ring optionally substituted with C$_1$–C$_4$ alkyl, C$_2$–C$_6$ alkenyl, C$_2$–C$_6$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$;

R$^6$ and R$^7$ are independently at each occurrence H, C$_1$–C$_6$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, C$_5$–C$_{12}$ bis(alkoxy)alkyl, aryl, aryl(C$_1$–C$_4$ alkyl)-, heteroaryl or heteroaryl(C$_1$–C$_4$ alkyl);

alternatively NR$^6$R$^7$ is piperidine, pyrrolidine, piperazine, N-methylpiperazine, morpholine or thiomorpholine;

R$^8$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl)-, heteroaryl or heteroaryl (C$_1$–C$_4$ alkyl);

R$^9$ and R$^{10}$ are independently at each occurrence selected from H, C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_2$–C$_6$ alkoxyalkyl, and C$_4$–C$_7$ cycloalkylalkyl;

R$^{11}$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl)-, heteroaryl, heteroaryl (C$_1$–C$_4$ alkyl), or —NR$^6$R$^7$;

R$^{12}$ is independently at each occurrence C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, or C$_4$–C$_7$ cycloalkylalkyl;

aryl is phenyl or naphthyl, each optionally substituted with 1 to 5 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{30}$, —SH, —S(O)$_n$R$^{32}$, —COR$^{32}$, —CO$_2$R$^{28}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{28}$, —NR$^{29}$R$^{30}$, and —CONR$^{29}$R$^{30}$;

heterocyclyl is saturated or partially saturated heteroaryl, optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{30}$, SH, —S(O)$_n$R$^{32}$, —COR$^{32}$, —CO$_2$R$^{32}$, —OC(O)R$^{32}$, —NR$^{29}$COR$^{29}$, —N(COR$^{32}$)$_2$, —NR$^{29}$CONR$^{29}$R$^{30}$, —NR$^{29}$CO$_2$R$^{32}$, —NR$^{29}$R$^{30}$, and —CONR$^{29}$R$^{30}$;

R$^{28}$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, phenyl, or phenyl(C$_1$–C$_4$ alkyl)-;

R$^{29}$ and R$^{30}$ are independently at each occurrence selected from H, C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_2$–C$_6$ alkoxyalkyl, and C$_4$–C$_7$ cycloalkylalkyl;

R$^{32}$ is independently at each occurrence C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, or C$_4$–C$_7$ cycloalkylalkyl; and n is 0, 1, or 2.

16. A pharmaceutical composition comprising a compound according to claim 1 and a pharmaceutically acceptable carrier.

* * * * *